(12) United States Patent
Galas et al.

(10) Patent No.: US 8,748,101 B2
(45) Date of Patent: Jun. 10, 2014

(54) METHODS, COMPOSITIONS, AND DEVICES UTILIZING MICRORNA TO DETERMINE PHYSIOLOGICAL CONDITIONS

(75) Inventors: David Galas, Seattle, WA (US); Richard Evan Gelinas, Seattle, WA (US); Clay Braden Marsh, Columbus, OH (US); Melissa Garnet Piper, Dublin, OH (US); Kai Wang, Bellevue, OH (US); Shile Zhang, Seattle, WA (US)

(73) Assignees: Battle Memorial Institute, Columbus, OH (US); Institute for Systems Biology, Seattle, WA (US); The Ohio State University Research Foundation, Columbus, OH (US)

( * ) Notice: Subject to any disclaimer, the term of this patent is extended or adjusted under 35 U.S.C. 154(b) by 490 days.

(21) Appl. No.: 12/615,969

(22) Filed: Nov. 10, 2009

(65) Prior Publication Data
US 2010/0216139 A1    Aug. 26, 2010

Related U.S. Application Data

(60) Provisional application No. 61/112,985, filed on Nov. 10, 2008.

(51) Int. Cl.
*C12Q 1/68* (2006.01)
(52) U.S. Cl.
USPC ........................................ 435/6.12; 435/6.11
(58) Field of Classification Search
None
See application file for complete search history.

(56) References Cited

U.S. PATENT DOCUMENTS

| | | |
|---|---|---|
| 2005/0123952 A1 | 6/2005 | Griffey et al. |
| 2006/0019286 A1 | 1/2006 | Horvitz et al. |
| 2006/0292616 A1 | 12/2006 | Neely et al. |
| 2007/0054287 A1 | 3/2007 | Bloch |
| 2007/0259350 A1 | 11/2007 | Bentwich et al. |
| 2007/0299030 A1 | 12/2007 | Dmitrovsky et al. |
| 2008/0254473 A1 | 10/2008 | Chen et al. |

FOREIGN PATENT DOCUMENTS

| | | |
|---|---|---|
| WO | WO 2007/103808 | 9/2007 |
| WO | WO 2008/073915 | 6/2008 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Bottoni et al., "Identification of Differentially Expressed MicroRNAs by Microarray: A Possible Role for MicroRNA Genes in Pituitary Adenomas," Journal of Cellular Physiology 210:370-377 (2007).
Dahiya et al., "MicroRNA Expression and Identification of Putative miRNA Targets in Ovarian Cancer," PLoS One, Jun. 2008, vol. 3, Issue 6, e2436, pp. 1-11.
Jiang et al., "Association of MicroRNA in Hepatocellular Carcinomas with Hepatitis Infection, Cirrhosis, and Patient Survival," Clin Cancer Res 2008;14(2) Jan. 15, 2008, pp. 419-427.
Lee et al., "Expression profiling identifies microRNA signature in pancreatic cancer," Int. J. Cancer: 120, 1046-1054 (2006).
Li et al., "Diagnostic and prognostic implications of microRNAs in human hepatocellular carcinoma," Int. J. Cancer: 123, 1616-1622 (2008).
Lui et al., "Patterns of Known and Novel Small RNAs in Human Cervical Cancer," Cancer Res 2007; 67:(13). Jul. 1, 2007, pp. 6031-6043.
Moschos et ai., "Expression profiling in vivo demonstrates rapid changes in lung microRNA levels following lipopolysaccharide-induced inflammation but not in the anti-inflammatory action of glucocorticoids," BMC Genomics 2007, 8:240, pp. 1-12.
Porkka et al., "MicroRNA Expression Profiling in Prostate Cancer," Cancer Res 2007; 67:(13). Jul. 1, 2007, pp. 6130-6135.
Ross et al., "MiRNA: The New Gene Silencer," Am J Clin Pathol. 2007;128(5):830-836.
Schepeler et al., "Diagnostic and Prognostic MicroRNAs in Stage II Colon Cancer," Cancer Res 2008; 68:(15). Aug. 1, 2008, pp. 6416-6424.
Volinia et al., "A microRNA expression signature of human solid tumors defines cancer gene targets," PNAS. Feb. 14, 2006, vol. 103, No. 7, pp. 2257-2261.
Wong et al., "MicroRNA-223 Is Commonly Repressed in Hepatocellular Carcinoma and Potentiates Expression of Stathmin1," Gastroenterology 2008;135:257-269.
Reduced expression of the let-7 microRNAs in human lung cancers in association with shortened postoperative survival, Cancer Research, American Association for Cancer Research, Baltimore, MD, vol. 64, Jun. 1, 2014, pp. 3753-3756, ISSN: 0008-5472, Takamizawa J. et al. Characterization of microRNAs in serum: a novel class of biomarkers for diagnosis of cancer and other diseases; Chen, et al. Cell Research—Xibao Yanjiu, Nature Publishing Group, GB, CN, vol. 18, No. 10. Oct. 1, 2008, ISSN: 1001-0602, pp. 997-1006.
Integrating the micrornome into the study of lung disease; Nana-Sinkam S.P. et al. Am J. Respir. Crit. Care Med. vol. 179, Sep. 11, 2008, pp. 4-10.
International Search Report and Written Opinion mailed Jun. 7, 2010.

* cited by examiner

*Primary Examiner* — James Martinell
(74) *Attorney, Agent, or Firm* — Richard M. Klein; Fay Sharpe LLP

(57) ABSTRACT

Methods, compositions, and devices are disclosed which use microRNA to detect, predict, treat, and monitor physiological conditions such as disease or injury. microRNA are isolated and their differential expression is measured to provide diagnostic information. This information may then be utilized for evaluation and/or treatment purposes.

7 Claims, 16 Drawing Sheets
(16 of 16 Drawing Sheet(s) Filed in Color)

METHODS, COMPOSITIONS, AND DEVICES UTILIZING MICRORNA TO DETERMINE PHYSIOLOGICAL CONDITIONS

This application claims priority to U.S. Provisional Patent Application Ser. No. 61/112,985, filed Nov. 10, 2008. That provisional application is hereby fully incorporated by reference in its entirety.

BACKGROUND

Disclosed herein are various methods, compositions, and devices utilizing microRNA, such as microRNA-based markers, to detect, predict, treat, or monitor various physiological or pathological conditions.

The ideal diagnostic marker has to fulfill certain key requirements including being specific, sensitive, robust, and non-invasive. Current disease diagnoses are primarily based on two different but complementary approaches—physical imaging and biomolecular profiling. Both approaches currently suffer from a lack of specificity and early detection capability. Tissue-specific blood biomarkers can increase the specificity to selected organs. However, the levels of these tissue-specific biomarkers are usually low in blood. In addition, the difficulty of developing suitable capture agents for proteins makes the identification and development of new molecular diagnostic markers difficult.

It would be desirable to provide new methods, compositions, and devices for diagnosing physiological and pathological conditions.

BRIEF DESCRIPTION

The present disclosure relates, in different embodiments, to the use of the levels of microRNA sequences (miRNA) in body fluids to establish correlations with the body's pathophysiological conditions. Exemplary body fluids include, but are not limited to, serum, plasma, saliva, urine, tears, amniotic fluid, sweat, cerebrospinal fluid, seminal fluid (semen), lung mucus (e.g. from bronchial lavage), pleural fluid, peritoneal fluid, colostrums, and breast milk. These levels can then provide diagnostic and/or predictive information with regard to important issues of health and disease.

Disclosed are methods of using microRNA sequences to detect a physiological condition. The methods comprise: isolating microRNA sequences from a biological sample; generating a microRNA profile from the isolated microRNA sequences, the profile including the levels of expressed microRNA sequences in the biological sample; comparing the microRNA profile with a reference to identify differentially expressed microRNA sequences; and detecting the physiological condition based on the identity or the levels of the differentially expressed microRNA sequences.

The biological sample may be a biopsy material, tissue, or body fluid. In embodiments, the biological sample comprises a body fluid selected from the group consisting of serum, plasma, lymph, saliva, urine, tears, sweat, semen, synovial fluid, cervical mucus, amniotic fluid, cerebrospinal fluid, and breast milk.

The microRNA sequences may be isolated by extracting the biological sample with an organic solvent to obtain an aqueous phase containing the microRNA sequences; and purifying the aqueous phase through a silica membrane to isolate the microRNA sequences.

The microRNA profile can be generated using hybridization to identify a microRNA sequences; or by using a quantitative polymerase chain reaction to identify the level of a microRNA sequences.

The reference can be a table of the levels of expressed microRNA sequences in a normal person, or a reference sample.

The biological sample may be from a microbe, such as a virus, bacterium, fungus, protozoan, or parasite.

The isolated microRNA sequences may be specific to a biological pathway, a cell type, or a tissue.

The physiological condition may be a disease, injury, or infection.

Also disclosed are methods of using microRNA sequences to detect or predict a physiological condition. These methods also comprise: generating a microRNA profile from a biological sample, the profile including the levels of expressed microRNA sequences in the biological sample; and comparing the microRNA profile with a reference to identify differentially expressed microRNA sequences. The physiological condition could then be detected or predicted based on the identity or the levels of the differentially expressed microRNA sequences. Alternatively, the physiological condition can be identified, and a treatment can then be administered based on the identity of the physiological condition.

Further disclosed are methods of using microRNA sequences to monitor a physiological condition, comprising: generating a first microRNA profile from a first biological sample of a patient; administering a treatment to the patient; generating a second microRNA profile from a second biological sample of the patient; comparing the second microRNA profile with the first microRNA profile to identify differentially expressed microRNA sequences; and identifying a change in the physiological condition based on the identity or the amounts of the differentially expressed microRNA sequences.

Additionally disclosed are methods of using microRNA sequences to treat a physiological condition. The methods comprise: identifying at least one microRNA sequence based on the physiological condition; and manipulating the level of the at least one microRNA sequence to treat the physiological condition. Manipulating the level of the at least one microRNA sequence may comprise: constructing a specific DNA or RNA sequence related to the at least one microRNA sequence; and delivering the specific DNA or RNA sequence to a targeted cell, tissue, or organ.

Also disclosed are methods of using microRNA sequences to detect, predict, or treat a physiological condition. The methods comprise: generating a microRNA profile from a biological sample; identifying at least one differentially expressed microRNA sequence by comparing the microRNA profile to a reference; and detecting, predicting, or treating the physiological condition based on the identity or the levels of the at least one differentially expressed microRNA sequence. In alternative embodiments, at least two differentially expressed microRNA sequences are identified.

Other methods of detecting or predicting a physiological condition comprise generating a microRNA profile from a biological sample, wherein the microRNA profile comprises at least one specific microRNA sequence; and comparing the microRNA profile to a reference to provide information useful for detecting or predicting the physiological condition. In alternative embodiments, the microRNA profile comprises at least two specific microRNA sequences.

A differentially expressed microRNA sequence can be identified by comparing the amount of a particular microRNA sequence in the microRNA profile with the amount of that particular microRNA sequence in the reference. A differentially expressed microRNA sequence is identified when the ratio of the amount in the microRNA profile to the amount in the reference is at least 1.5, or at least 3.

When the physiological condition is related to liver disease or liver injury, in some embodiments, the microRNA profile or the specific microRNA sequence(s) may comprise at least one microRNA sequence selected from the group consisting of mmu-miR-122, mmu-miR-486, mmu-miR-125b-5p, mmu-let-7d*, mmu-miR-101a, mmu-miR-101b, mmu-miR-1224, mmu-miR-124, mmu-miR-125a-3p, mmu-miR-125a-5p, mmu-miR-127, mmu-miR-130a, mmu-miR-133a, mmu-miR-133b, mmu-miR-135a*, mmu-miR-141, mmu-miR-193, mmu-miR-193b, mmu-miR-199a-5p, mmu-miR-199b*, mmu-miR-200c, mmu-miR-202-3p, mmu-miR-205, mmu-miR-22, mmu-miR-23b, mmu-miR-26a, mmu-miR-27b, mmu-miR-291a-5p, mmu-miR-294*, mmu-miR-29b, mmu-miR-30a, mmu-miR-30c-1*, mmu-miR-30e, mmu-miR-320, mmu-miR-327, mmu-miR-339-3p, mmu-miR-342-3p, mmu-miR-370, mmu-miR-375, mmu-miR-451, mmu-miR-466f-3p, mmu-miR-483, mmu-miR-494, mmu-miR-574-5p, mmu-miR-652, mmu-miR-671-5p, mmu-miR-685, mmu-miR-710, mmu-miR-711, mmu-miR-712, mmu-miR-714, mmu-miR-720, mmu-miR-721, mmu-miR-877, mmu-miR-877*, mmu-miR-882, mmu-miR-93, mmu-miR-99a, and human orthologs thereof.

In other embodiments where the physiological condition is related to liver disease or liver injury, the microRNA profile or the specific microRNA sequence may comprise at least one microRNA sequence selected from the group consisting of mmu-miR-122, mmu-miR-486, mmu-miR-125b-5p, mmu-let-7d*, mmu-miR-101a, mmu-miR-101b, mmu-miR-1224, mmu-miR-124, mmu-miR-125a-3p, mmu-miR-125a-5p, mmu-miR-133a, mmu-miR-133b, mmu-miR-135a*, mmu-miR-193, mmu-miR-193b, mmu-miR-199a-5p, mmu-miR-199b*, mmu-miR-202-3p, mmu-miR-291a-5p, mmu-miR-294*, mmu-miR-30c-1*, mmu-miR-30e, mmu-miR-327, mmu-miR-339-3p, mmu-miR-342-3p, mmu-miR-375, mmu-miR-466f-3p, mmu-miR-483, mmu-miR-574-5p, mmu-miR-652, mmu-miR-671-5p, mmu-miR-685, mmu-miR-710, mmu-miR-711, mmu-miR-712, mmu-miR-714, mmu-miR-720, mmu-miR-721, mmu-miR-877, mmu-miR-877*, mmu-miR-882, and human orthologs thereof.

In particular embodiments, the at least one differentially expressed microRNA sequence or the at least one specific sequence comprises hsa-miR-122. In more specific embodiments, they comprise hsa-miR-122 and either hsa-miR-486-3p or hsa-miR-486-5p (i.e. the human orthologs to mmu-miR-486). The ratio of the amount of miR-122 to the amount of miR-486 may be greater than 4.0, including greater than 6.0.

When the physiological condition is neurological disease or neurological injury, in some embodiments, the microRNA profile or the specific microRNA sequence may comprise at least one microRNA sequence selected from the group consisting of mmu-let-7g, mmu-miR-298, mmu-miR-1, mmu-miR-101a*, mmu-miR-101b, mmu-miR-1224, mmu-miR-126-5p, mmu-miR-127, mmu-miR-128, mmu-miR-129-3p, mmu-miR-133b, mmu-miR-136, mmu-miR-138, mmu-miR-138*, mmu-miR-139-3p, mmu-miR-140, mmu-miR-140*, mmu-miR-142-3p, mmu-miR-143, mmu-miR-146a, mmu-miR-146b, mmu-miR-148b, mmu-miR-150, mmu-miR-15a*, mmu-miR-15b, mmu-miR-181b, mmu-miR-181d, mmu-miR-183, mmu-miR-185, mmu-miR-186, mmu-miR-191*, mmu-miR-194, mmu-miR-19a, mmu-miR-200a, mmu-miR-200b, mmu-miR-200b*, mmu-miR-202-3p, mmu-miR-206, mmu-miR-208a, mmu-miR-21, mmu-miR-211, mmu-miR-221, mmu-miR-222, mmu-miR-223, mmu-miR-27a, mmu-miR-27b*, mmu-miR-28*, mmu-miR-290-5p, mmu-miR-291a-5p, mmu-miR-297a, mmu-miR-299, mmu-miR-29b, mmu-miR-29c*, mmu-miR-301b, mmu-miR-302c*, mmu-miR-30c, mmu-miR-31, mmu-miR-322, mmu-miR-323-3p, mmu-miR-324-3p, mmu-miR-324-5p, mmu-miR-326, mmu-miR-328, mmu-miR-331-5p, mmu-miR-341, mmu-miR-34b-5p, mmu-miR-34c*, mmu-miR-369-3p, mmu-miR-374, mmu-miR-376b, mmu-miR-379, mmu-miR-380-3p, mmu-miR-382, mmu-miR-384-5p, mmu-miR-409-5p, mmu-miR-411, mmu-miR-411*, mmu-miR-423-5p, mmu-miR-425, mmu-miR-429, mmu-miR-434-5p, mmu-miR-450b-3p, mmu-miR-451, mmu-miR-455, mmu-miR-465c-3p, mmu-miR-466d-5p, mmu-miR-467e*, mmu-miR-484, mmu-miR-486, mmu-miR-487b, mmu-miR-497, mmu-miR-505, mmu-miR-511, mmu-miR-539, mmu-miR-540-3p, mmu-miR-551b, mmu-miR-568, mmu-miR-654-5p, mmu-miR-669a, mmu-miR-686, mmu-miR-688, mmu-miR-699, mmu-miR-701, mmu-miR-706, mmu-miR-708, mmu-miR-720, mmu-miR-721, mmu-miR-744*, mmu-miR-760, mmu-miR-770-5p, mmu-miR-7a, mmu-miR-7b, mmu-miR-881*, mmu-miR-93, mmu-miR-96, mghv-miR-M1-6, mghv-miR-M1-9, and human orthologs thereof.

In other embodiments where the physiological condition is neurological disease or neurological injury, the microRNA profile or the specific microRNA sequence may comprise at least one microRNA sequence selected from the group consisting of mmu-let-7g, mmu-miR-298, mmu-miR-101a*, mmu-miR-101b, mmu-miR-1224, mmu-miR-126-5p, mmu-miR-128, mmu-miR-129-3p, mmu-miR-133b, mmu-miR-138*, mmu-miR-139-3p, mmu-miR-140*, mmu-miR-146a, mmu-miR-148b, mmu-miR-15a*, mmu-miR-15b, mmu-miR-181b, mmu-miR-181d, mmu-miR-185, mmu-miR-186, mmu-miR-191*, mmu-miR-19a, mmu-miR-200b*, mmu-miR-202-3p, mmu-miR-208a, mmu-miR-211, mmu-miR-27b*, mmu-miR-28*, mmu-miR-290-5p, mmu-miR-291a-5p, mmu-miR-297a, mmu-miR-299, mmu-miR-29c*, mmu-miR-301b, mmu-miR-302c*, mmu-miR-322, mmu-miR-323-3p, mmu-miR-324-3p, mmu-miR-324-5p, mmu-miR-326, mmu-miR-328, mmu-miR-331-5p, mmu-miR-341, mmu-miR-34b-5p, mmu-miR-34c*, mmu-miR-369-3p, mmu-miR-374, mmu-miR-376b, mmu-miR-379, mmu-miR-380-3p, mmu-miR-382, mmu-miR-384-5p, mmu-miR-409-5p, mmu-miR-411, mmu-miR-411*, mmu-miR-423-5p, mmu-miR-425, mmu-miR-429, mmu-miR-434-5p, mmu-miR-450b-3p, mmu-miR-465c-3p, mmu-miR-466d-5p, mmu-miR-467e*, mmu-miR-505, mmu-miR-511, mmu-miR-539, mmu-miR-540-3p, mmu-miR-551b, mmu-miR-568, mmu-miR-654-5p, mmu-miR-669a, mmu-miR-686, mmu-miR-688, mmu-miR-699, mmu-miR-701, mmu-miR-706, mmu-miR-720, mmu-miR-721, mmu-miR-744*, mmu-miR-760, mmu-miR-770-5p, mmu-miR-7a, mmu-miR-7b, mmu-miR-881*, mmu-miR-96, mghv-miR-M1-6, mghv-miR-M1-9, and human orthologs thereof.

When the physiological condition is related to lung disease or lung injury, in some embodiments, the microRNA profile or the specific microRNA sequence may comprise at least one microRNA sequence selected from the group consisting of hsa-miR-135a*, hsa-miR-10b, hsa-miR-1224-3p, hsa-miR-1224-5p, hsa-miR-1225-3p, hsa-miR-1225-5p, hsa-miR-1226*, hsa-miR-1227, hsa-miR-1228, hsa-miR-1229, hsa-miR-1234, hsa-miR-1237, hsa-miR-1238, hsa-miR-124, hsa-miR-129*, hsa-miR-129-3p, hsa-miR-136*, hsa-miR-187*, hsa-miR-188-5p, hsa-miR-190b, hsa-miR-198, hsa-miR-22, hsa-miR-220b, hsa-miR-300, hsa-miR-301b, hsa-miR-30e, hsa-miR-338-3p, hsa-miR-33a*, hsa-miR-33b, hsa-miR-33b*, hsa-miR-34c-3p, hsa-miR-34c-5p, hsa-miR-363*, hsa-miR-371-3p, hsa-miR-371-5p, hsa-miR-375, hsa-miR-377*, hsa-miR-423-5p, hsa-miR-424, hsa-miR-424*, hsa-miR-429, hsa-miR-448, hsa-miR-449a, hsa-miR-449b, hsa-miR-450b-3p, hsa-miR-452, hsa-miR-454*, hsa-miR-455-3p, hsa-miR-483-3p, hsa-miR-483-5p, hsa-miR-491-3p, hsa-miR-491-5p, hsa-miR-493, hsa-miR-493*, hsa-miR-494, hsa-miR-497, hsa-miR-498, hsa-miR-500, hsa-miR-503, hsa-miR-505, hsa-miR-507, hsa-miR-513a-3p, hsa-miR-513a-5p, hsa-miR-513b, hsa-miR-513c, hsa-miR-515-5p, hsa-miR-518b, hsa-miR-518c*, hsa-miR-518d-3p, hsa-miR-518d-5p, hsa-miR-518e*, hsa-miR-520d-5p, hsa-miR-520h, hsa-miR-541, hsa-miR-545*, hsa-miR-548d-3p, hsa-miR-548d-5p, hsa-miR-551a, hsa-miR-551b, hsa-miR-552, hsa-miR-554, hsa-miR-556-5p, hsa-miR-557, hsa-miR-559, hsa-miR-561, hsa-miR-564, hsa-miR-572, hsa-miR-575, hsa-miR-576-3p, hsa-miR-578, hsa-miR-583, hsa-miR-586, hsa-miR-589, hsa-miR-589*, hsa-miR-591, hsa-miR-595, hsa-miR-601, hsa-miR-602, hsa-miR-609, hsa-miR-610, hsa-miR-612, hsa-miR-613, hsa-miR-614, hsa-miR-615-3p, hsa-miR-616, hsa-miR-619, hsa-miR-622, hsa-miR-623, hsa-miR-624*, hsa-miR-627, hsa-miR-633, hsa-miR-634, hsa-miR-638, hsa-miR-639, hsa-miR-640, hsa-miR-642, hsa-miR-644, hsa-miR-647, hsa-miR-648, hsa-miR-652, hsa-miR-654-5p, hsa-miR-658, hsa-miR-659, hsa-miR-662, hsa-miR-663, hsa-miR-665, hsa-miR-671-5p, hsa-miR-675, hsa-miR-708, hsa-miR-708*, hsa-miR-744*, hsa-miR-760, hsa-miR-765, hsa-miR-766, hsa-miR-767-3p, hsa-miR-802, hsa-miR-874, hsa-miR-876-3p, hsa-miR-876-5p, hsa-miR-877, hsa-miR-877*, hsa-miR-885-3p, hsa-miR-885-5p, hsa-miR-886-3p, hsa-miR-890, hsa-miR-891b, hsa-miR-892b, hsa-miR-920, hsa-miR-922, hsa-miR-923, hsa-miR-92b, hsa-miR-92b*, hsa-miR-933, hsa-miR-934, hsa-miR-935, hsa-miR-936, hsa-miR-937, hsa-miR-939, hsa-miR-940, hsv1-miR-H1, hsv1-miR-LAT, kshv-miR-K12-12, kshv-miR-K12-3, kshv-miR-K12-3*, kshv-miR-K12-4-5p, kshv-miR-K12-6-5p, kshv-miR-K12-8, kshv-miR-K12-9, kshv-miR-K12-9*, ebv-miR-BART10*, ebv-miR-BART12, ebv-miR-BART13, ebv-miR-BART13*, ebv-miR-BART15, ebv-miR-BART1-5p, ebv-miR-BART16, ebv-miR-BART18-5p, ebv-miR-BART19-3p, ebv-miR-BART19-5p, ebv-miR-BART20-5p, ebv-miR-BART2-5p, ebv-miR-BART3*, ebv-miR-BART5, ebv-miR-BART6-5p, ebv-miR-BART7, ebv-miR-BART7*, ebv-miR-BHRF1-1, ebv-miR-BHRF1-3, hcmv-miR-UL148D, hcmv-miR-UL22A, hcmv-miR-UL22A*, hcmv-miR-UL70-3p, hcmv-miR-UL70-5p, hcmv-miR-US25-1, hcmv-miR-US25-2-3p, hcmv-miR-US25-2-5p, hcmv-miR-US4, hiv1-miR-H1, hiv1-miR-N367, and human orthologs thereof.

In other embodiments where the physiological condition is related to lung disease or lung injury, the microRNA profile or the specific microRNA sequence may comprise at least one microRNA sequence selected from the group consisting of hsa-miR-135a*, hsa-miR-1224-3p, hsa-miR-1224-5p, hsa-miR-1225-3p, hsa-miR-1225-5p, hsa-miR-1226*, hsa-miR-1227, hsa-miR-1228, hsa-miR-1229, hsa-miR-1234, hsa-miR-1237, hsa-miR-1238, hsa-miR-124, hsa-miR-129*, hsa-miR-129-3p, hsa-miR-136*, hsa-miR-187*, hsa-miR-188-5p, hsa-miR-190b, hsa-miR-220b, hsa-miR-300, hsa-miR-301b, hsa-miR-30e, hsa-miR-338-3p, hsa-miR-33a*, hsa-miR-33b, hsa-miR-33b*, hsa-miR-34c-3p, hsa-miR-34c-5p, hsa-miR-363*, hsa-miR-371-3p, hsa-miR-371-5p, hsa-miR-375, hsa-miR-377*, hsa-miR-423-5p, hsa-miR-424*, hsa-miR-429, hsa-miR-448, hsa-miR-449a, hsa-miR-449b, hsa-miR-450b-3p, hsa-miR-452, hsa-miR-454*, hsa-miR-455-3p, hsa-miR-483-3p, hsa-miR-483-5p, hsa-miR-491-3p, hsa-miR-491-5p, hsa-miR-493, hsa-miR-493*, hsa-miR-500, hsa-miR-505, hsa-miR-507, hsa-miR-513a-3p, hsa-miR-513a-5p, hsa-miR-513b, hsa-miR-513c, hsa-miR-515-5p, hsa-miR-518c*, hsa-miR-518d-3p, hsa-miR-518d-5p, hsa-miR-518e*, hsa-miR-520d-5p, hsa-miR-541, hsa-miR-545*, hsa-miR-548d-3p, hsa-miR-548d-5p, hsa-miR-551b, hsa-miR-552, hsa-miR-554, hsa-miR-556-5p, hsa-miR-557, hsa-miR-559, hsa-miR-561, hsa-miR-564, hsa-miR-575, hsa-miR-576-3p, hsa-miR-578, hsa-miR-583, hsa-miR-586, hsa-miR-589, hsa-miR-589*, hsa-miR-591, hsa-miR-595, hsa-miR-602, hsa-miR-609, hsa-miR-610, hsa-miR-612, hsa-miR-613, hsa-miR-614, hsa-miR-615-3p, hsa-miR-616, hsa-miR-619, hsa-miR-623, hsa-miR-624*, hsa-miR-633, hsa-miR-638, hsa-miR-639, hsa-miR-640, hsa-miR-642, hsa-miR-644, hsa-miR-647, hsa-miR-652, hsa-miR-654-5p, hsa-miR-658, hsa-miR-659, hsa-miR-665, hsa-miR-671-5p, hsa-miR-675, hsa-miR-708*, hsa-miR-744*, hsa-miR-760, hsa-miR-765, hsa-miR-766, hsa-miR-767-3p, hsa-miR-768-3p, hsa-miR-768-5p, hsa-miR-801, hsa-miR-802, hsa-miR-874, hsa-miR-876-3p, hsa-miR-876-5p, hsa-miR-877, hsa-miR-877*, hsa-miR-885-3p, hsa-miR-885-5p, hsa-miR-886-3p, hsa-miR-890, hsa-miR-891b, hsa-miR-892b, hsa-miR-920, hsa-miR-922, hsa-miR-923, hsa-miR-92b*, hsv1-miR-H1, hsv1-miR-LAT, kshv-miR-K12-12, kshv-miR-K12-3, kshv-miR-K12-3*, kshv-miR-K12-4-5p, kshv-miR-K12-6-5p, kshv-miR-K12-8, kshv-miR-K12-9, kshv-miR-K12-9*, ebv-miR-BART10*, ebv-miR-BART12, ebv-miR-BART13, ebv-miR-BART13*, ebv-miR-BART15, ebv-miR-BART1-5p, ebv-miR-BART16, ebv-miR-BART18-5p, ebv-miR-BART19-3p, ebv-miR-BART19-5p, ebv-miR-BART20-5p, ebv-miR-BART2-5p, ebv-miR-BART3*, ebv-miR-BART5, ebv-miR-BART6-5p, ebv-miR-BART7, ebv-miR-BART7*, ebv-miR-BHRF1-1, ebv-miR-BHRF1-3, hcmv-miR-UL148D, hcmv-miR-UL22A, hcmv-miR-UL22A*, hcmv-miR-UL70-3p, hcmv-miR-UL70-5p, hcmv-miR-US25-1, hcmv-miR-US25-2-3p, hcmv-miR-US25-2-5p, hcmv-miR-US4, hiv1-miR-H1, hiv1-miR-N367, and human orthologs thereof.

The physiological condition may also be a lung disease or lung injury, such as chronic obstructive pulmonary disease (COPD) and idiopathic pulmonary fibrosis (IPF), also known as interstitial lung disease (ILD).

In embodiments, the at least one differentially expressed microRNA sequence or at least one specific microRNA sequence is selected from the group consisting of hsa-miR-630, hsa-miR-134, hsa-miR-1225-5p, hsa-miR-135a*, hsa-miR-150*, hsa-miR-22, hsa-miR-223, hsa-miR-448, hsa-miR-451, hsa-miR-483-5p, hsa-miR-575, hsa-miR-638, hsa-miR-923, hsa-miR-92a-2*, hsa-miR-939, hsa-miR-940, hsv1-miR-H1, kshv-miR-K12-3, hsv1-miR-LAT, hcmv-miR-UL70-3p, hsv1-miR-H1, hsv1-miR-LAT, kshv-miR-K12-3, hcmv-miR-UL70-3p, and human orthologs thereof.

In other embodiments, the biological sample is plasma and the at least one differentially expressed microRNA sequence or at least one specific microRNA sequence is selected from the group consisting of hsa-miR-630, hsa-miR-134, hsa-miR-1225-5p, hsa-miR-135a*, hsa-miR-150*, hsa-miR-22, hsa-miR-223, hsa-miR-483-5p, hsa-miR-575, hsa-miR-638, hsa-miR-923, hsa-miR-939, hsa-miR-940, hsv1-miR-H1, hsv1-miR-LAT, kshv-miR-K12-3, hcmv-miR-UL70-3p, and human orthologs thereof. In some particular embodiments, the microRNA profile consists of only a selection of at least two of these microRNA sequences, i.e. the microRNA profile does not look at other microRNA sequences.

In yet other embodiments, the biological sample is plasma and the at least one differentially expressed microRNA sequence or at least one specific microRNA sequence is selected from the group consisting of hsa-miR-630, hsa-miR-134, hcmv-miR-UL70-3p, hsa-miR-1225-5p, hsa-miR-135a*, hsa-miR-150*, hsa-miR-483-5p, hsa-miR-575, hsa-miR-638, hsv1-miR-H1, hsv1-miR-LAT, and human orthologs thereof. In some particular embodiments, the microRNA profile consists of only a selection of at least two of these microRNA sequences, i.e. the microRNA profile does not look at other microRNA sequences.

In some alternate embodiments, the biological sample is plasma and at least two differentially expressed microRNA sequences or specific microRNA sequences are identified. At least one of the at least two differentially expressed microRNA sequences or specific microRNA sequences is selected from the group consisting of hsa-miR-630, hcmv-miR-UL70-3p, hsa-miR-1225-5p, hsa-miR-134, hsa-miR-135a*, hsa-miR-150*, hsa-miR-483-5p, hsa-miR-575, hsa-miR-638, hsv1-miR-H1, hsv1-miR-LAT, and human orthologs thereof. The other one of the at least two differentially expressed microRNA sequences or specific microRNA sequences is selected from the group consisting of hsa-miR-451, hsa-miR-448, hsa-miR-92a-2*, and human orthologs thereof. In some particular embodiments, the microRNA profile consists of only a selection of these microRNA sequences, i.e. the microRNA profile does not look at other microRNA sequences.

In yet other embodiments, the biological sample is lung tissue and the at least one differentially expressed microRNA sequence is selected from the group consisting of hsa-miR-451, hsa-miR-923, hsa-miR-1225-5p, hsa-miR-22, hsa-miR-223, hsa-miR-638, kshv-miR-K12-3, and human orthologs thereof. In some particular embodiments, the microRNA profile consists of only a selection of these microRNA sequences.

In still other embodiments, the biological sample is plasma and the at least one differentially expressed microRNA sequence is selected from the group consisting of hsa-miR-940, hsa-miR-134, hsa-miR-135a*, hsa-miR-150*, hsa-miR-483-5p, hsa-miR-575, hsa-miR-939, hsv1-miR-H1, kshv-miR-K12-3, hsv1-miR-LAT, hcmv-miR-UL70-3p, and human orthologs thereof. In some particular embodiments, the microRNA profile consists of only a selection of these microRNA sequences, i.e. the microRNA profile does not look at other microRNA sequences.

Also disclosed are methods of using microRNA sequences to detect a lung condition, comprising: generating a microRNA profile from a biological sample; and detecting the lung condition based on the levels of at least one overexpressed microRNA sequence and at least one underexpressed microRNA sequence. The at least one overexpressed microRNA sequence is selected from the group consisting of hsa-miR-630, hcmv-miR-UL70-3p, hsa-miR-1225-5p, hsa-miR-134, hsa-miR-135a*, hsa-miR-150*, hsa-miR-483-5p, hsa-miR-575, hsa-miR-638, hsv1-miR-H1, hsv1-miR-LAT, and human orthologs thereof. The at least one underexpressed microRNA sequence is selected from the group consisting of hsa-miR-451, hsa-miR-448, and hsa-miR-92a-2*, and human orthologs thereof. In some particular embodiments, the microRNA profile examines only a selection of these listed microRNA sequences.

Also disclosed are methods of detecting or predicting certain physiological conditions in a patient. Those methods comprise generating a microRNA profile from a biological sample provided by the patient; identifying at least one differentially expressed microRNA sequence by comparing the microRNA profile to a reference; and detecting or predicting the physiological condition based on the identity or the amounts of the at least one differentially expressed microRNA sequence. The biological sample comprises (i) serum or plasma; and (ii) an additional body fluid specific to a particular location of the body that is relevant to the particular physiological condition. In a first embodiment, the biological sample further comprises amniotic fluid and the physiological condition is the health status of a fetus being carried by the patient. In a second embodiment, the biological sample further comprises urine and the physiological condition is the health status of a bladder or a kidney of the patient. In a third embodiment, the biological sample further comprises breast milk and the physiological condition is the health status of a breast of the patient. In a fourth embodiment, the biological sample further comprises saliva and the physiological condition is the health status of the head and neck region of the patient. In a fifth embodiment, the biological sample further comprises tears and the physiological condition is the health status of an eye of the patient. In a sixth embodiment, the biological sample further comprises semen and the physiological condition is the health status of a prostate or male reproductive organ of the patient. In a seventh embodiment, the biological sample further comprises synovial fluid and the physiological condition is the health status of a joint of the patient. In an eighth embodiment, the biological sample further comprises sweat and the physiological condition is the health status of the skin of the patient. In a ninth embodiment, the biological sample further comprises cerebrospinal fluid and the physiological condition is the health status of the central nerve system of the patient.

Also disclosed are methods of diagnosing a physiological condition. The methods comprise taking a sample of a body fluid and a sample of a body tissue from a patient. A first microRNA profile is generated from the body fluid sample, and a second microRNA profile is generated from the body tissue sample. At least two differentially expressed microRNA sequences are identified in the first microRNA profile by comparing the first microRNA profile to a first reference. At least two differentially expressed microRNA sequences are identified in the second microRNA profile by comparing the second microRNA profile to a second reference. The physiological condition is then diagnosed based on the differentially expressed microRNA sequences identified. In particular, the differentially expressed microRNA sequences in the first microRNA profile are different from the differentially expressed microRNA sequences in the second microRNA profile. This difference in the differentially expressed microRNA sequences between the body fluid and the body tissue increases the probability of a correct diagnosis.

Also included are assays for detecting the identity and/or levels of the various combinations of microRNA sequences described above.

These and other non-limiting aspects and/or objects of the disclosure are more particularly described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the disclosure set forth herein and not for the purposes of limiting the same.

Figure 2:
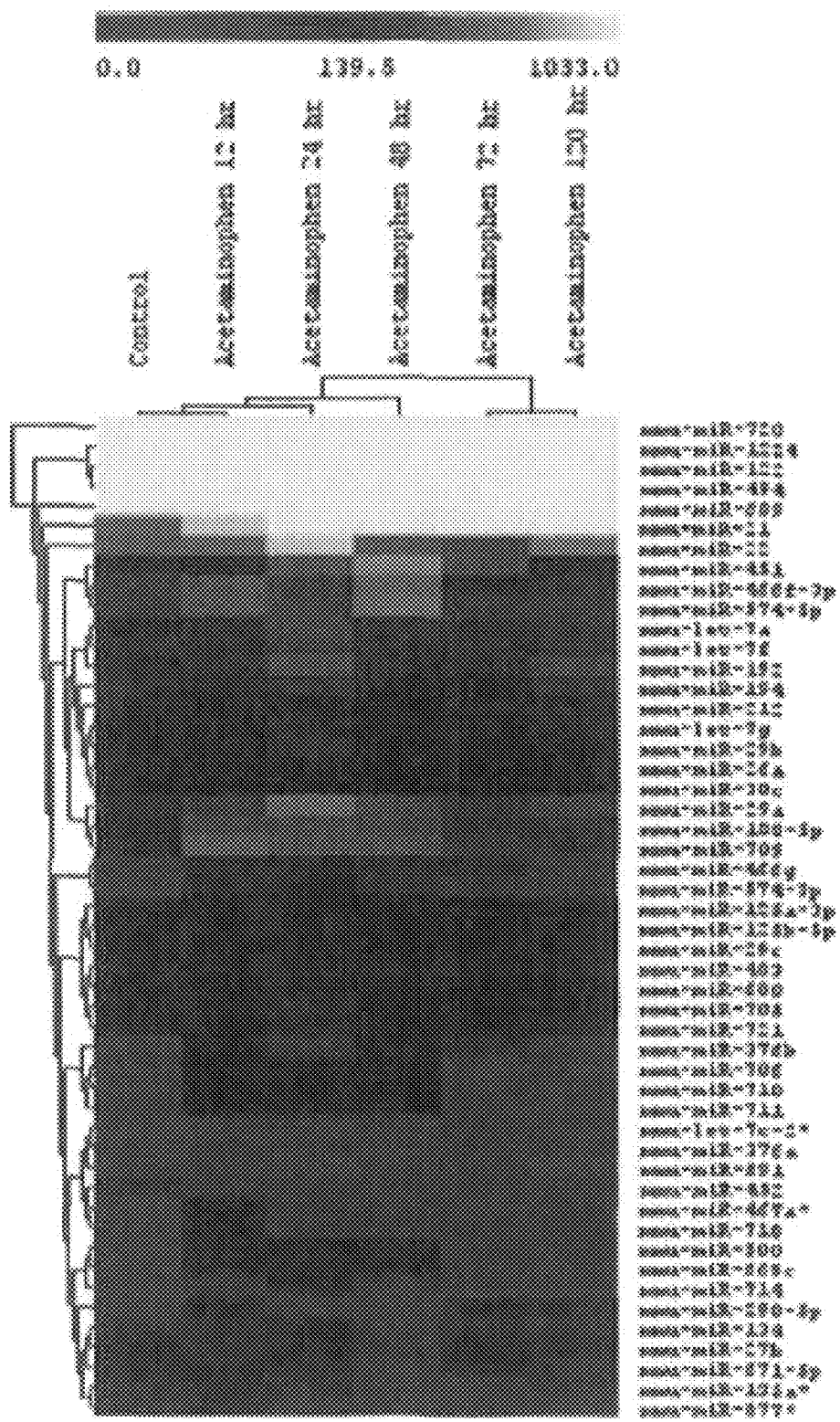
FIG. 2 is a microRNA profile showing changes in specific microRNA expression levels over time in the liver after exposing the animal to a high dose of acetaminophen.

For reference, the text on the right-hand side of FIG. 2 reads, in order from top to bottom: mmu-miR-720, mmu-miR-1224, mmu-miR-122, mmu-miR-494, mmu-miR-609, mmu-miR-21, mmu-miR-22, mmu-miR-451, mmu-miR-466f-3p, mmu-miR-574-5p, mmu-let-7a, mmu-let-7f, mmu-miR-192, mmu-miR-194, mmu-miR-212, mmu-let-7g, mmu-miR-29b, mmu-miR-26a, mmu-miR-30c, mmu-miR- 29a, mmu-miR-188-5p, mmu-miR-709, mmu-miR-466g, mmu-miR-574-3p, mmu-miR-125a-3p, mmu-miR-125b-5p, mmu-miR-29c, mmu-miR-483, mmu-miR-600, mmu-miR-705, mmu-miR-721, mmu-miR-376b, mmu-miR-706, mmu-miR-710, mmu-miR-711, mmu-let-7c-2*, mmu-miR-376a, mmu-miR-891, mmu-miR-452, mmu-miR-467a*, mmu-miR-718, mmu-miR-500, mmu-miR-669c, mmu-miR-714, mmu-miR-290-5p, mmu-miR-134, mmu-miR-27b, mmu-miR-671-5p, mmu-miR-135a*, and mmu-miR-877*.

Figure 3:
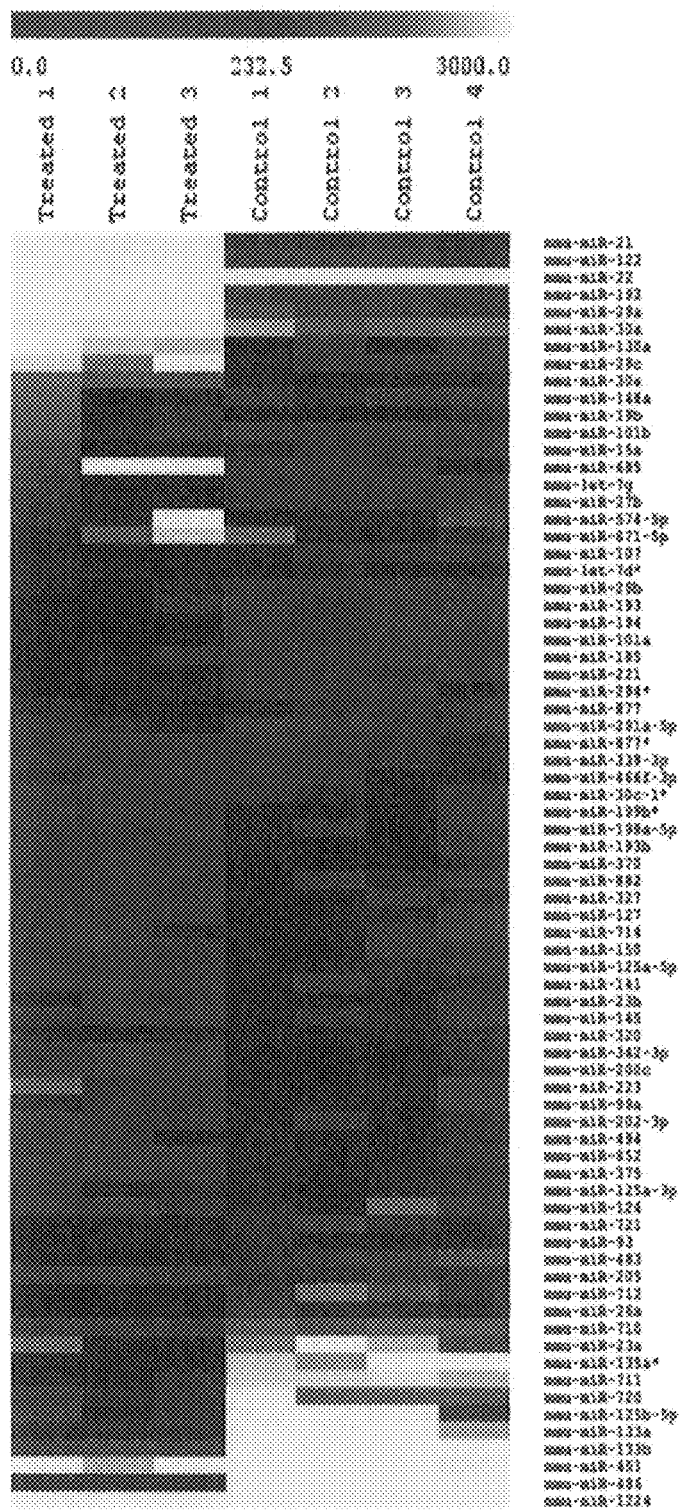

FIG. 3 is a microRNA profile showing differences in specific microRNA levels between plasma samples from a treated group and a control group.

For reference, the text on the right-hand side of FIG. 3 reads, in order from top to bottom: mmu-miR-21, mmu-miR-122, mmu-miR-22, mmu-miR-192, mmu-miR-29a, mmu-miR-30a, mmu-miR-130a, mmu-miR-29c, mmu-miR-30a, mmu-miR-148a, mmu-miR-19b, mmu-miR-101b, mmu-miR-15a, mmu-miR-685, mmu-let-7g, mmu-miR-27b, mmu-miR-574-5p, mmu-miR-671-5p, mmu-miR-107, mmu-let-7d*, mmu-miR-29b, mmu-miR-193, mmu-miR-194, mmu-miR-101a, mmu-miR-185, mmu-miR-221, mmu-miR-294*, mmu-miR-877, mmu-miR-291a-5p, mmu-miR-877*, mmu-miR-339-3p, mmu-miR-466f-3p, mmu-miR-30c-1*, mmu-miR-199b, mmu-miR-199a-5p, mmu-miR-193b, mmu-miR-370, mmu-miR-882, mmu-miR-327, mmu-miR-127, mmu-miR-714, mmu-miR-150, mmu-miR-125a-5p, mmu-miR-141, mmu-miR-23b, mmu-miR-145, mmu-miR-320, mmu-miR-342-3p, mmu-miR-200c, mmu-miR-223, mmu-miR-99a, mmu-miR-202-3p, mmu-miR-494, mmu-miR-652, mmu-miR-375, mmu-miR-125a-3p, mmu-miR-124, mmu-miR-721, mmu-miR-93, mmu-miR-483, mmu-miR-205, mmu-miR-712, mmu-miR-26a, mmu-miR-710, mmu-miR-23a, mmu-miR-135a*, mmu-miR-711, mmu-miR-720, mmu-miR-125b-5p, mmu-miR-133a, mmu-miR-133b, mmu-miR-451, mmu-miR-486, and mmu-miR-1224.

Figure 4:
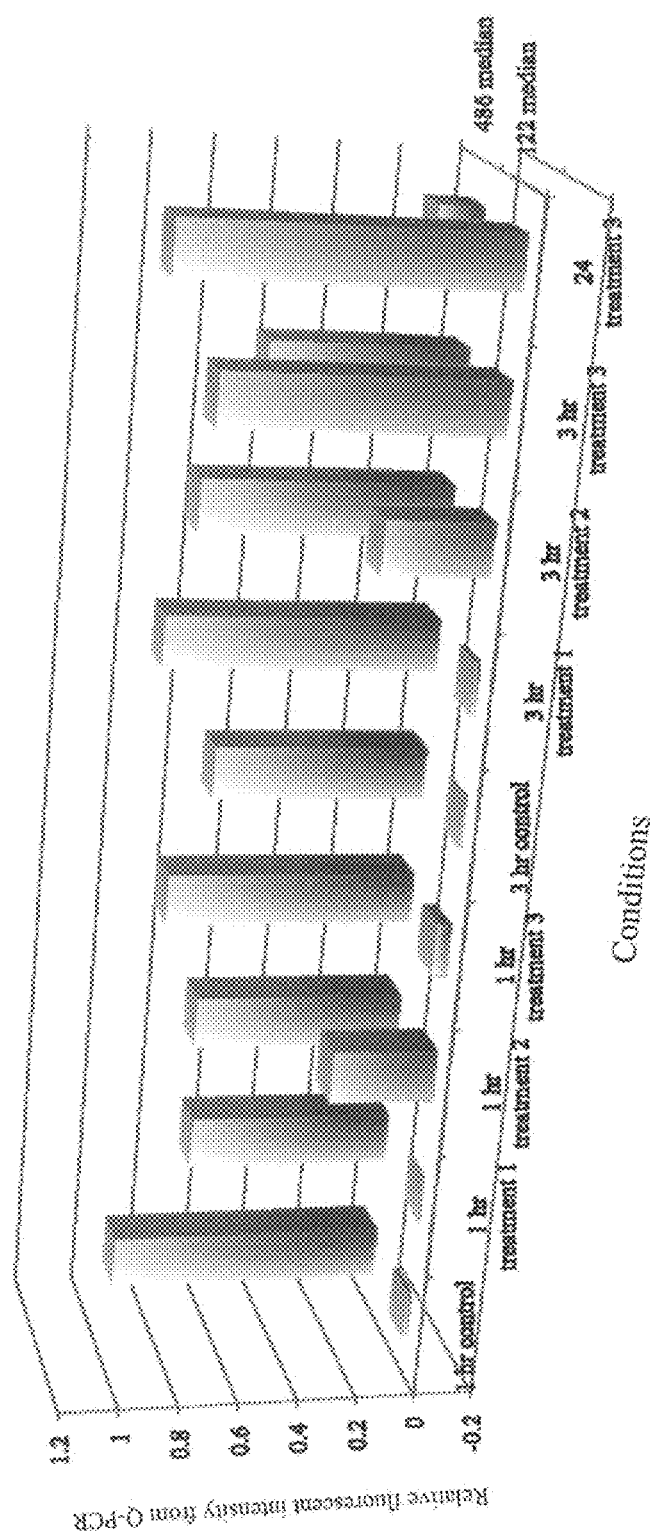

FIG. 4 is a graph of intensities for two selected microRNA sequences, mir-122 and mir-486 in plasma after exposing the animal to different doses of acetaminophen.

Figure 5:
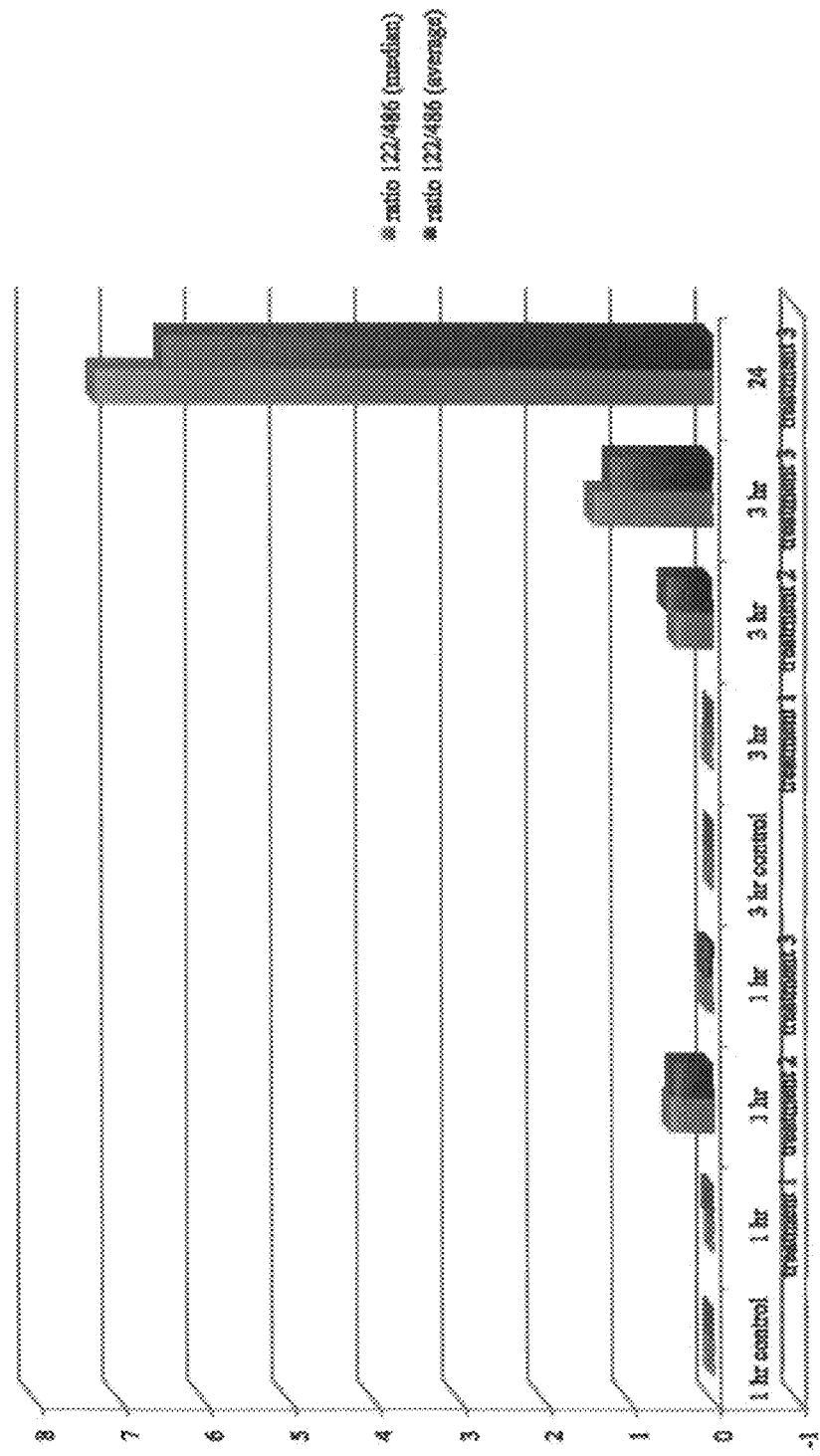

FIG. 5 is a graph of the ratio between mir-122 and mir-486 (either median or average intensities) for the same data as FIG. 4.

Figure 6:
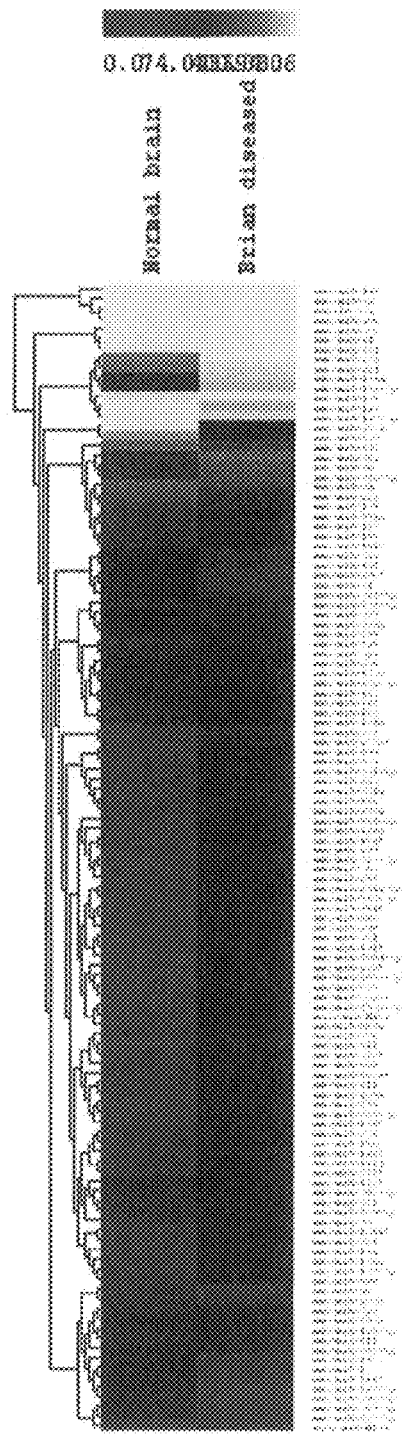

FIG. 6 is a microRNA profile showing differences in microRNA expression levels between normal brain tissue and diseased brain tissue.

Figure 7:
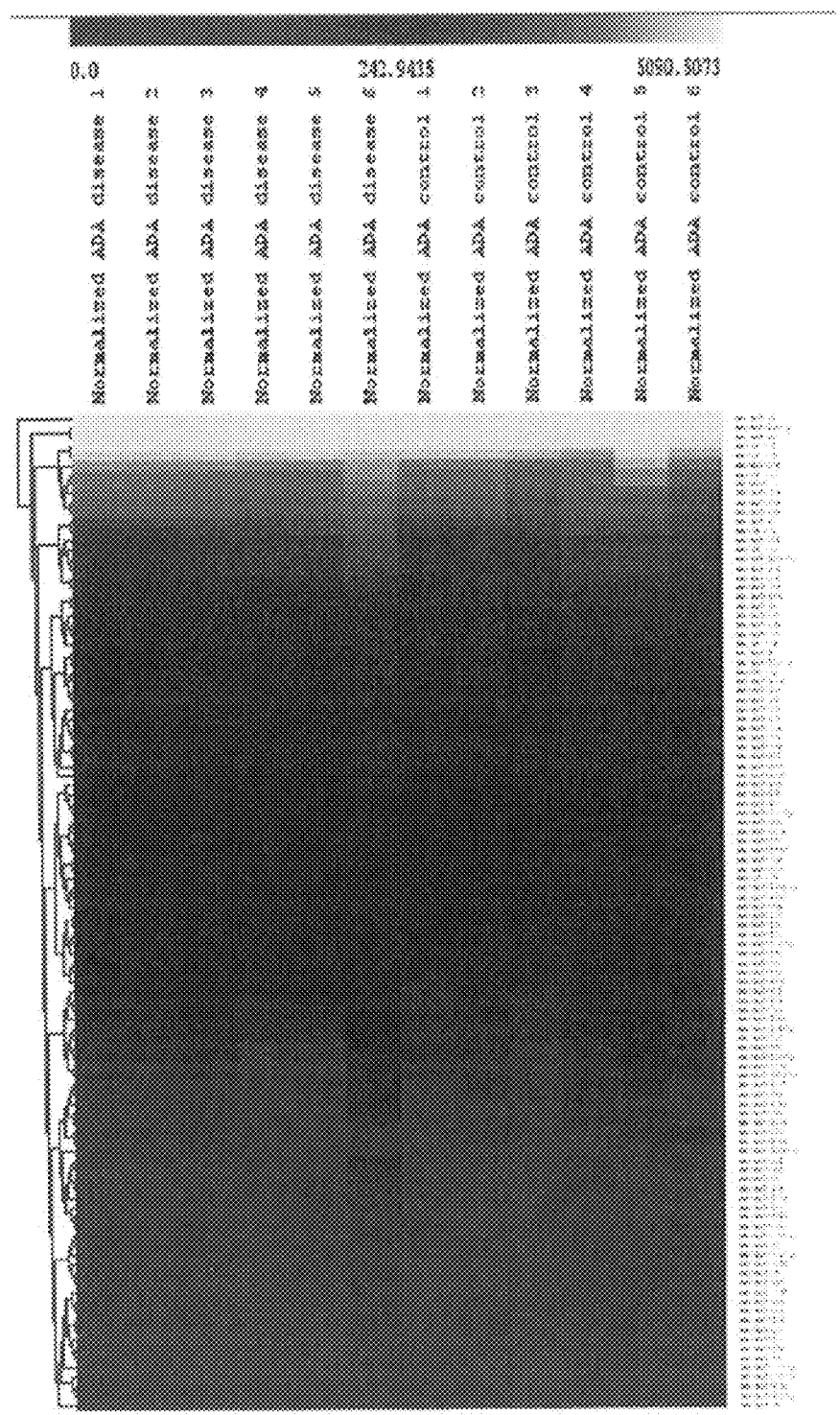

FIG. 7 is a microRNA profile showing differences in microRNA expression levels as a disease progressed in lung tissue.

Figure 8:
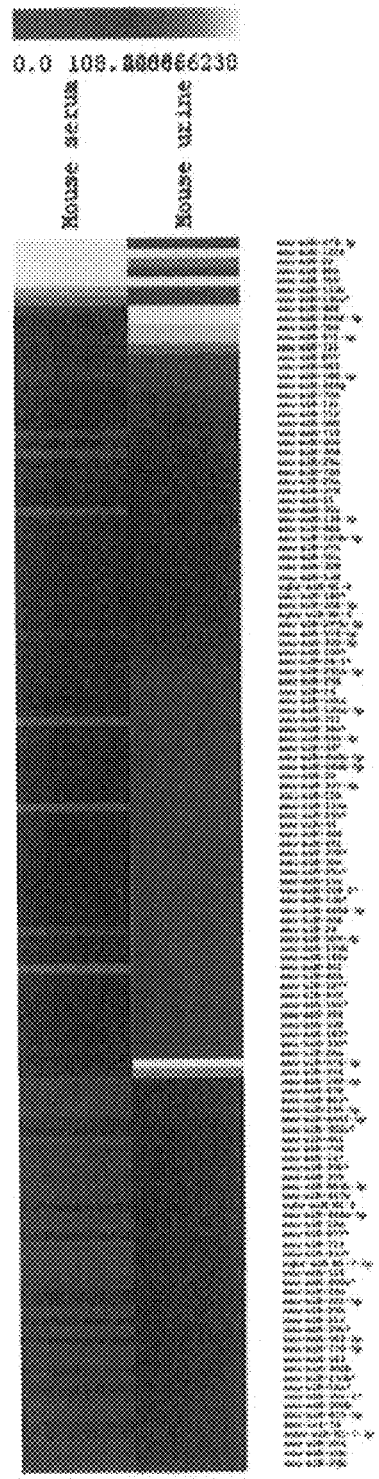

FIG. 8 is a microRNA profile showing differences in microRNA expression levels between serum and urine samples.

Figure 9:
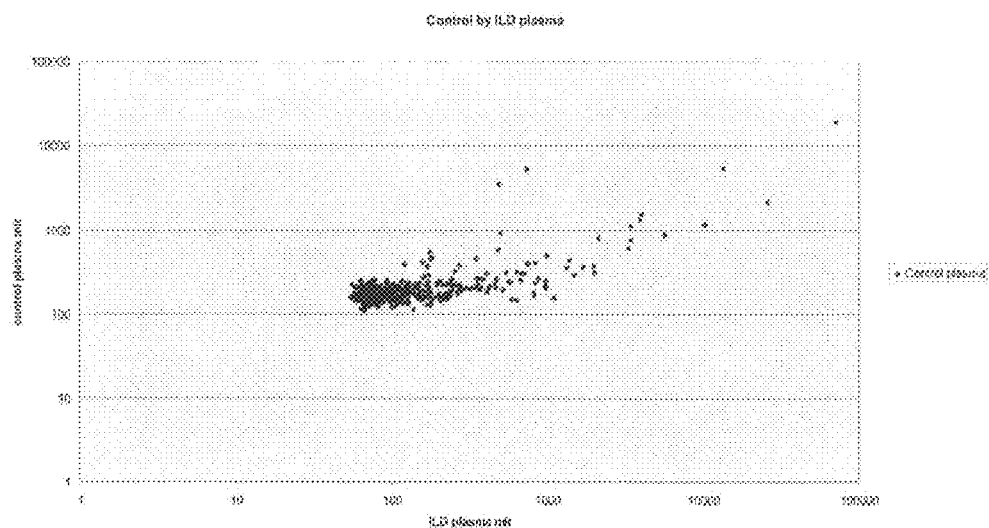

FIG. 9 is a graph comparing miRNA expression levels in control plasma samples with ILD plasma samples.

Figure 10A:
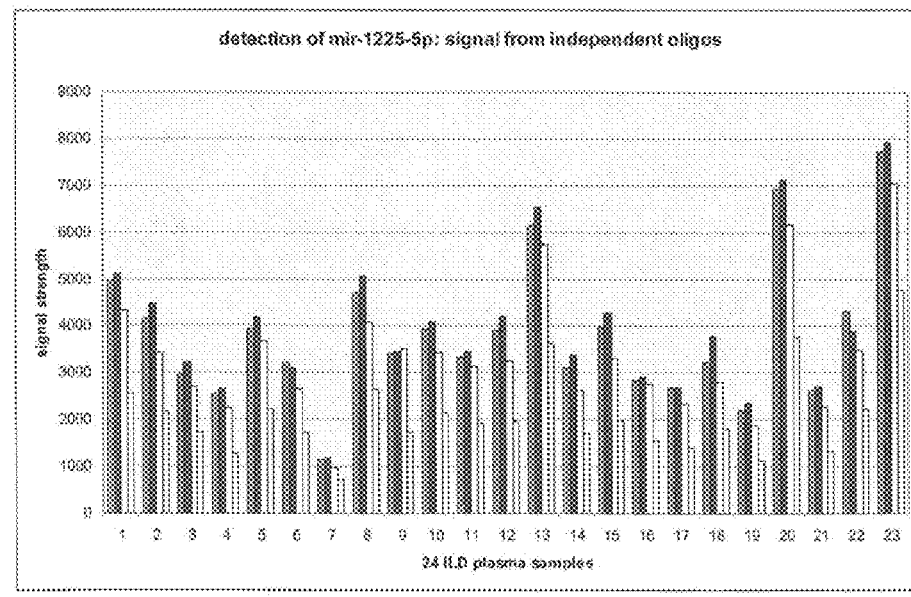
Figure 10B:
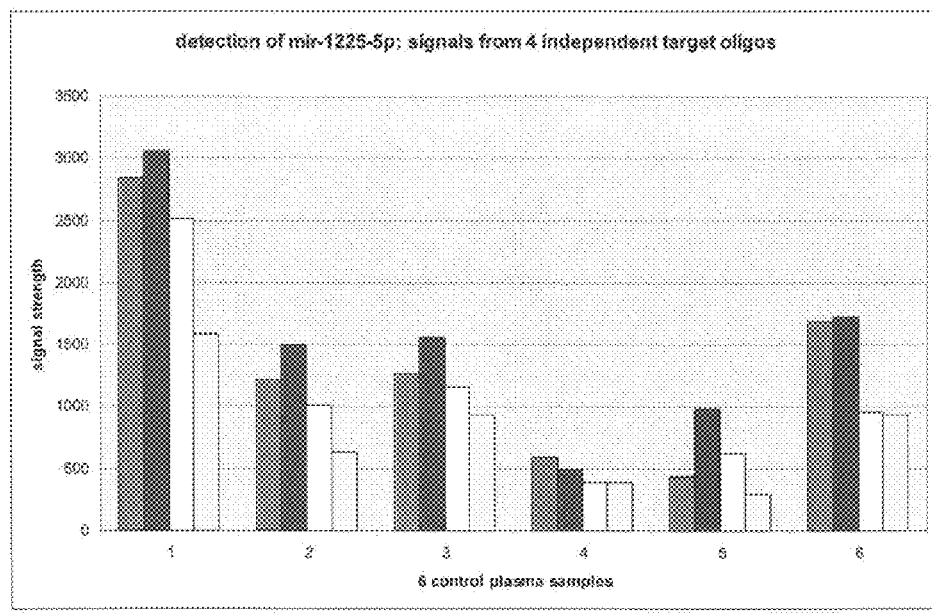

FIGS. 10A-10B are graphs showing the signal strength in the ILD and control plasma samples of FIG. 9.

Figure 11:
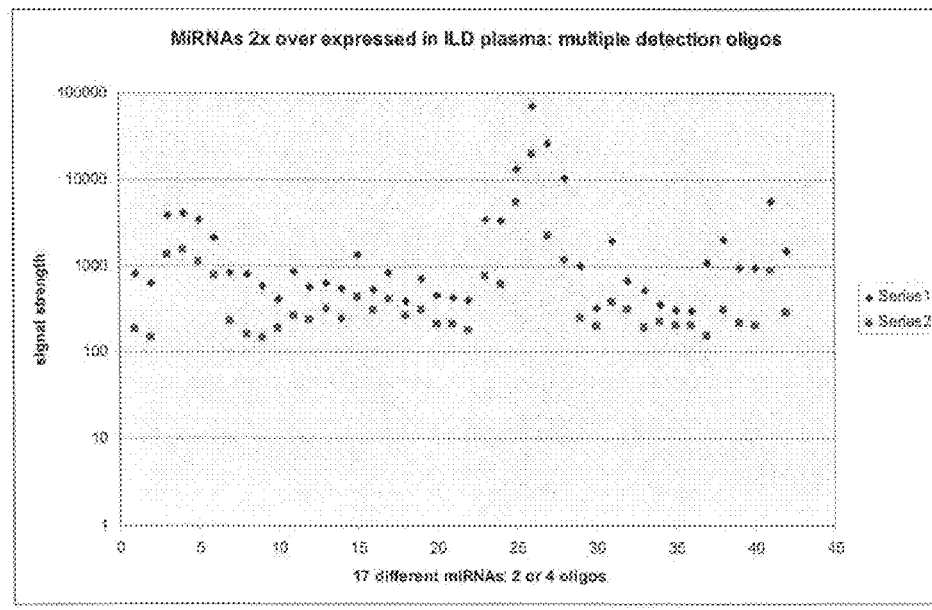

FIG. 11 is a graph showing the signal strength for all oligonucleotide probes used to target certain microRNA sequences.

Figure 12:
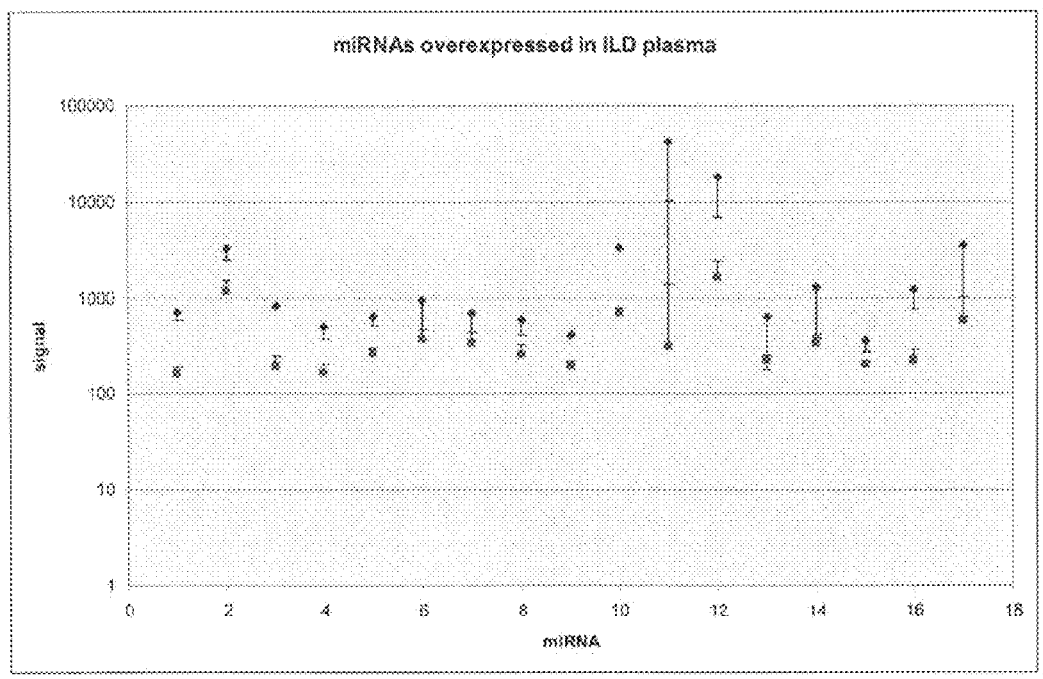

FIG. 12 is a graph showing the difference in the signal strength for certain microRNA sequences in the ILD and control plasma samples of FIG. 9.

Figure 13:
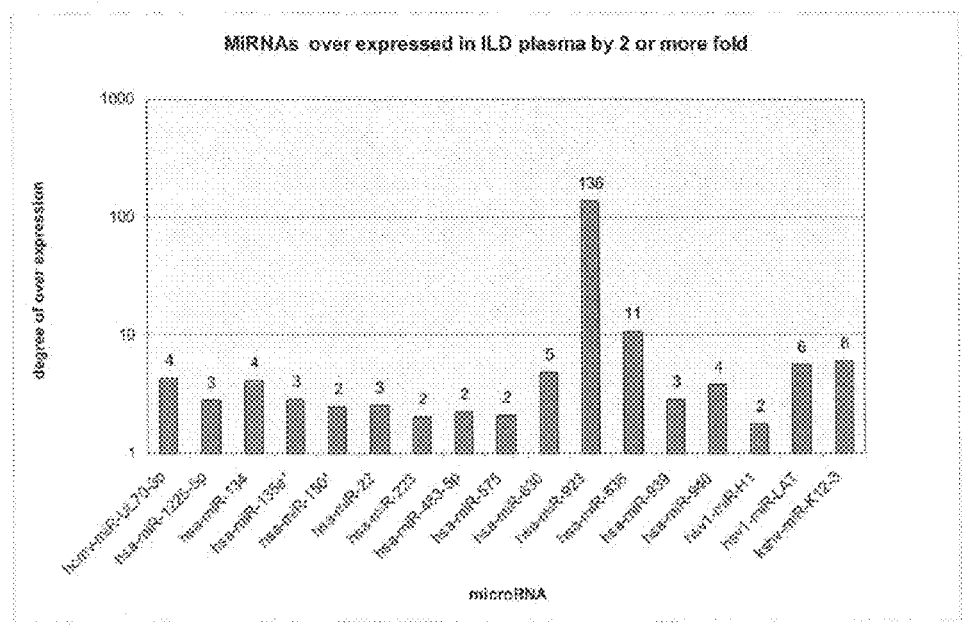

FIG. 13 is a graph showing the degree of overexpression in certain microRNA sequences in the ILD and control plasma samples of FIG. 9.

Figure 14:
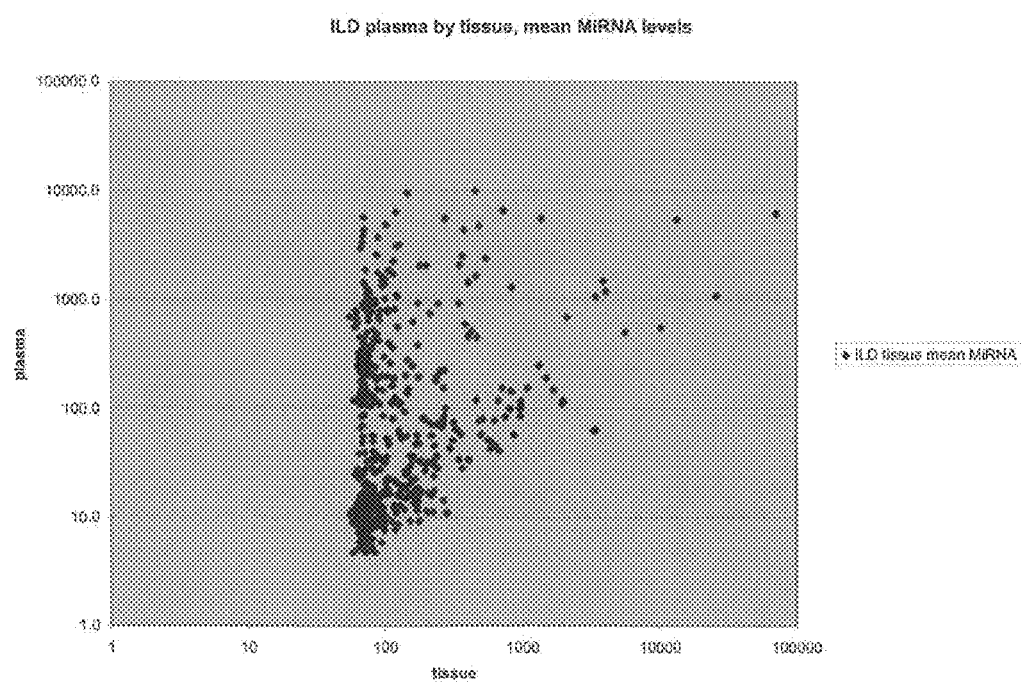

FIG. 14 is a graph comparing miRNA expression levels in ILD tissue samples with ILD plasma samples.

Figure 15:
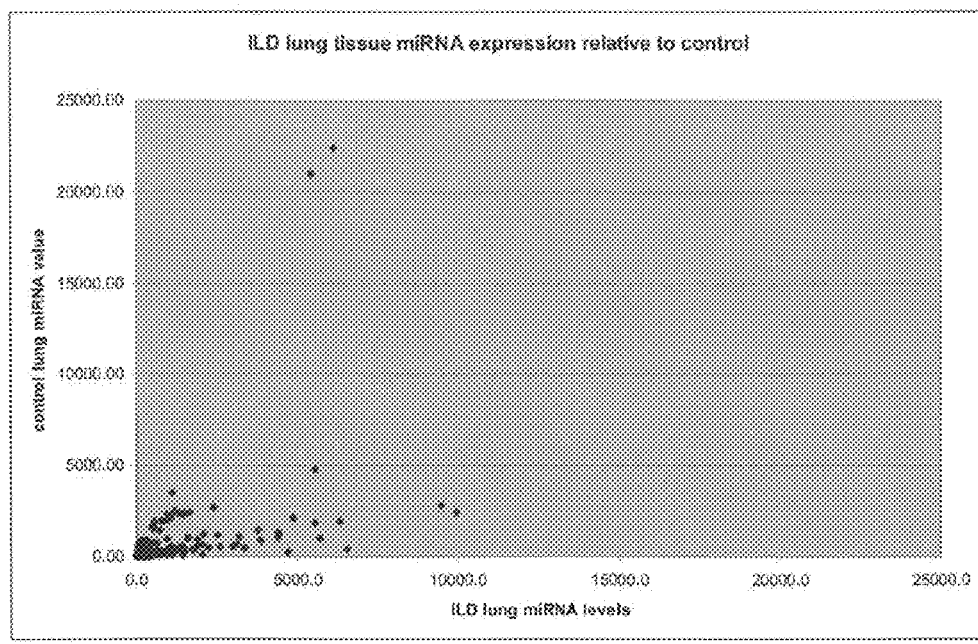

FIG. 15 is a graph comparing miRNA expression levels in control lung tissue samples with ILD lung tissue samples.

Figure 16:
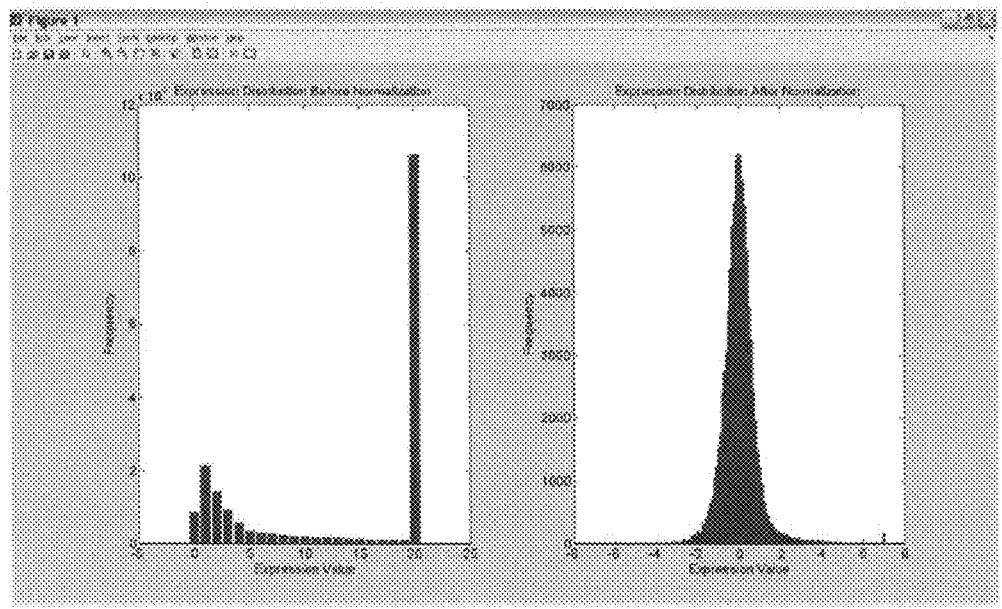

FIG. 16 is a graph showing the effect of normalization on data in a data analysis method.

Figure 17A:
Figure 17B:
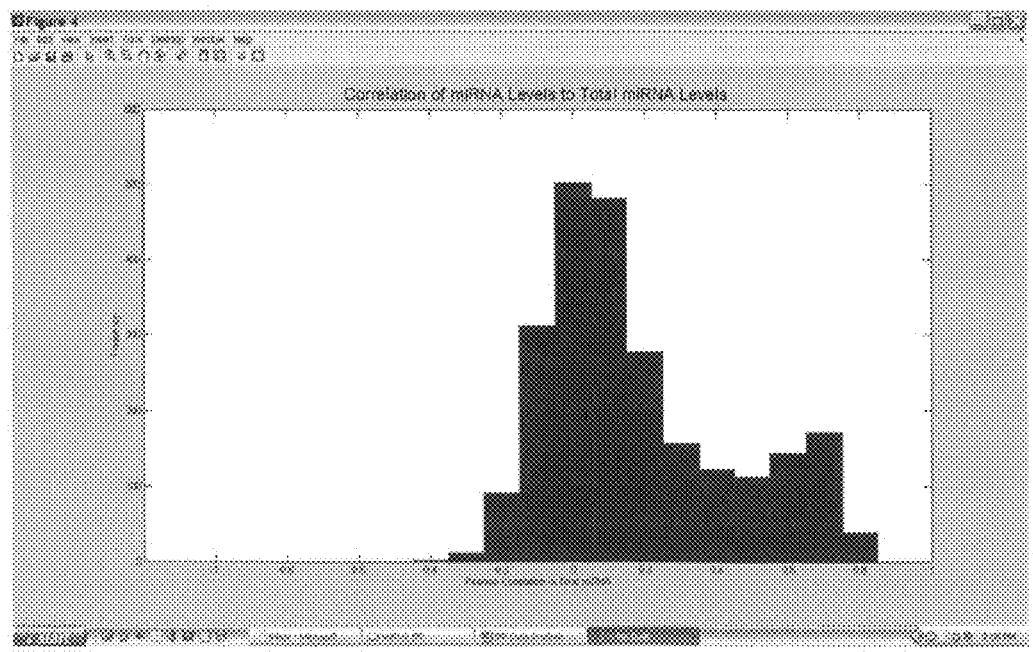

FIGS. 17A-17B are graphs showing the effect of normalization on the quality of data.

Figure 18:
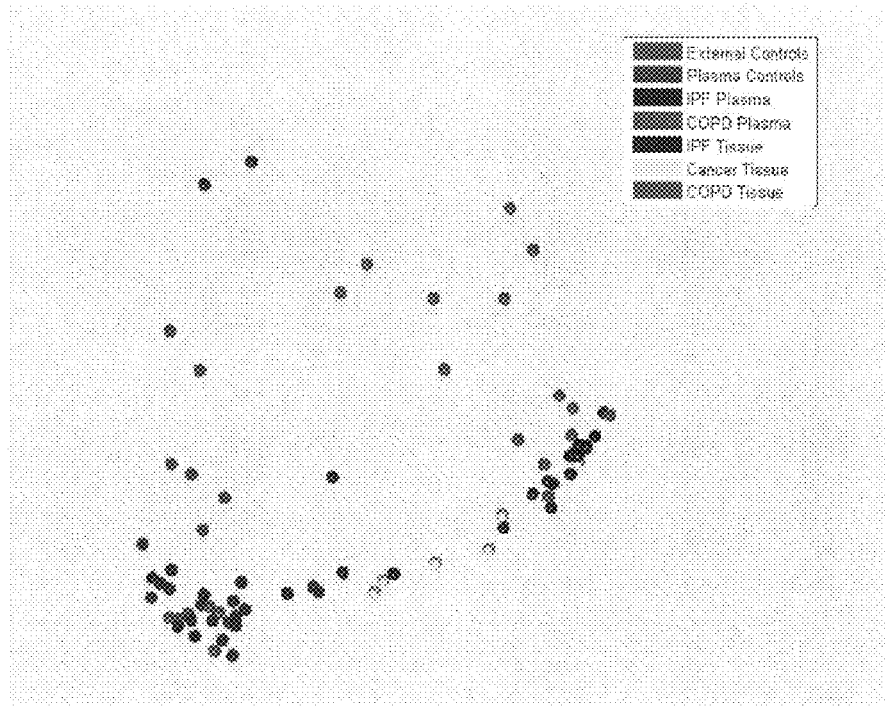

FIG. 18 is a graph clustering normalized miRNA data.

Figure 19:
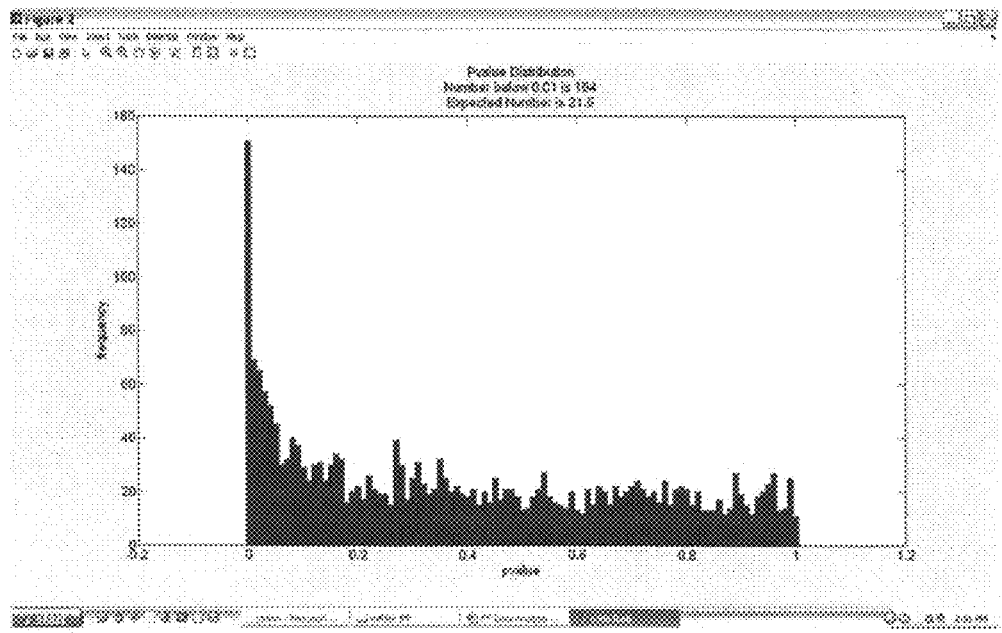

FIG. 19 is a graph showing the p-value distribution of all miRNA in a sample.

Figure 20:
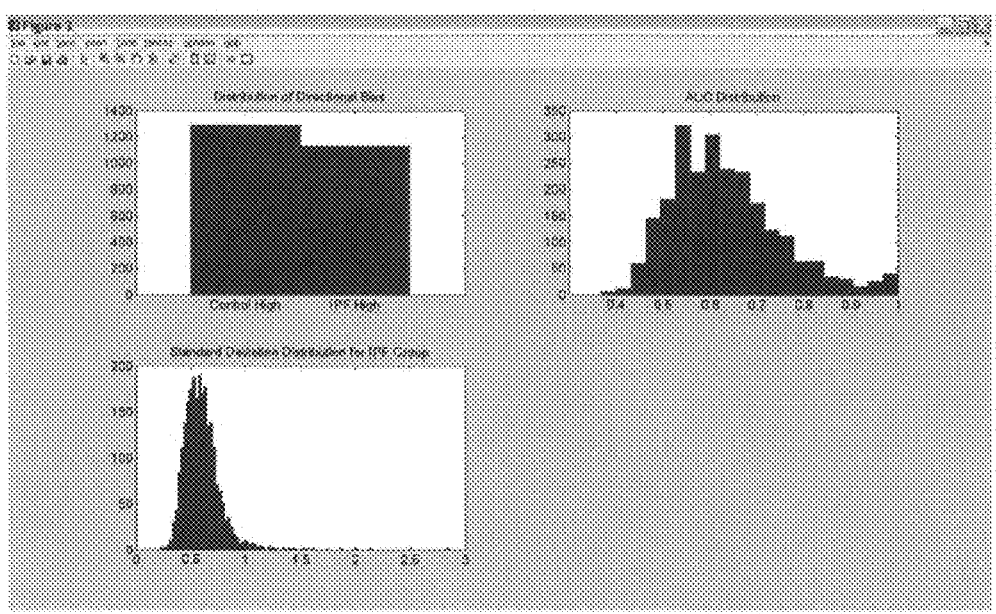

FIG. 20 is a collection of charts showing the selection of panels that separates data.

DETAILED DESCRIPTION

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

MicroRNAs (also known as miRNA) are small but potent regulatory non-coding ribonucleic acid (RNA) sequences first identified in *C. elegans* in 1993. miRNA may be about 21 to about 23 nucleotides in length. Through sequence complementation, microRNA interacts with messenger RNA (mRNA) and affects the stability of mRNA and/or the initiation and progression of protein translation. It has been estimated that over 30% of the mRNAs are regulated by microRNA. Like mRNA, some of the microRNAs also display restricted tissue distribution. The biological function of microRNA is yet to be fully understood; however, it has been shown that microRNA sequences are involved in various physiological and pathological conditions, including differentiation, development, cancer, and neurological disorders. Unlike mRNA and proteins, microRNA is reasonably well conserved across different species. Thus, a specific microRNA sequences which is shown to correlate to a particular condition, such as disease or injury, in one species, should also correlate to that particular condition in other species, particularly humans (i.e. Homo sapiens). This correlation provides useful diagnostic content.

MicroRNAs can also be manipulated with commonly used molecular biology techniques including complementary DNA (cDNA) synthesis, polymerase chain reactions, Northern blotting, and array based hybridization. This makes it possible to easily investigate the function(s) of a given microRNA sequences of interest.

A microRNA is encoded by a gene. When the DNA of the gene is transcribed into RNA, the RNA is not subsequently translated into protein. Instead each primary transcript (a pri-mir) is processed into a short stem-loop structure (a pre-mir) and finally into a mature sequence, designated miR. The primary transcript can form local hairpin structures, which ordinarily are processed such that a single microRNA sequence accumulates from one arm of a hairpin precursor molecule. Sometimes the primary transcript contains multiple hairpins, and different hairpins give rise to different microRNA sequences.

The microRNA sequences discussed herein are named according the miRBase database available at http://microrna.sanger.ac.uk/ and maintained by the Wellcome Trust Sanger Institute (now redirected to http://www.miRBase.org/). Generally speaking, microRNA sequences are assigned sequential numerical identifiers, with the numerical identifier based on sequence similarity. A 3- or 4-letter prefix designates the species from which the microRNA sequence came. For example, the hsa in hsa-miR-101 refers to homo sapiens.

Orthologous sequences, or orthologs, refer to microRNA sequences that are in different species but are similar (i.e. homologous) because they originated from a common ancestor. Generally speaking, orthologs have the same numerical identifier and are believed to serve a similar function. For example, mmu-miR-101 and hsa-miR-101 are in mouse and human, respectively, and are orthologs to each other. In this disclosure, microRNA sequences are referred to without the prefix designating the species, and should be construed as preferentially referring to the human microRNA sequence and the murine sequence. For example, miR-101 should be construed as referring to hsa-miR-101 and mmu-miR-101.

Paralogous sequences, or paralogs, are microRNA sequences that differ from each other in only a few positions. Paralogs occur within a species. Paralogs are designated with letter suffixes. For example, mmu-miR-133a and mmu-miR-133b are paralogs.

Identical microRNA sequences that originate from separate genomic loci are given numerical suffixes, such as hsa-miR-26a-1 and hsa-miR-26a-2.

Sometimes, two different mature microRNA sequences are excised from opposite arms of the same hairpin precursor. The two microRNA sequences can be designated in at least two ways. First, when it is possible to determine which arm gives rise to the predominantly expressed miRNA sequence, an asterisk has been used to denote the less predominant form, such as hsa-let-7b and hsa-let-7b*. Alternatively, they are named to designate whether they come from the 5' or 3' arm, such as hsa-miR-125a-3p and hsa-miR-125a-5p.

Specific microRNA sequences have been identified in the blood that are associated with liver injuries. Thus, the levels of selected microRNA sequences can be used to detect, predict, or diagnose diseases, predict and monitor therapeutic responses, and/or predict disease outcomes.

MicroRNA-based blood markers offer superior properties over existing markers. Such markers are sensitive, in part because microRNA signals can be amplified using standard polymerase chain reactions (PCR) while protein-based markers cannot be easily amplified. Because the sequence and expression profile of microRNAs are largely conserved across species, discoveries made in animal models can be easily translated to and adapted for use in humans. MicroRNA assays can be quickly performed and developed with standard PCR or array based systems; therefore, beside PCR primers, there is no need to develop special detection agents. Finally, since microRNA can be easily accessed in various body fluids, obtaining such diagnostic information can be done non-invasively.

The level of specific microRNA sequences(s) in a cell, tissue, or body fluid(s) can be used to monitor the physiopathological conditions of the body.

Sets of microRNA sequences in the tissue and the serum have been identified that are associated with liver injuries, lung injuries, and lung diseases. The combination of information from multiple microRNA expression level changes can further enhance the sensitivity and specificity of disease/injury detection, including using the ratio of paired microRNA sequences.

MicroRNA profiles, for example a microRNA profile of tissue-specific microRNA sequences, could be used to monitor the health status of that tissue. Those microRNA sequences could also be used as therapeutic targets for diseases associated with the tissue.

MicroRNA sequences from microbes or infectious agents, such as bacteria and viruses, could be used as an indication of infection. Host responses could be monitored by using the combination of microRNA sequences from infectious agents and the host as measured from the host's body fluids.

Biological processes occurring in a number of cell types or tissues could be monitored by the use of microRNA profiles specific to a process or network. These specific microRNA sequences could also be used as therapeutic targets for diseases associated with the biological processes.

The methods of the present disclosure could be used to detect, predict, monitor, or treat a physiological condition such as a disease, injury, or infection. Generally, the methods include: (a) isolating microRNA sequences from a biological sample; (b) generating a microRNA profile from the isolated microRNA sequences, the profile including the levels of expressed microRNA sequences in the biological sample; and (c) comparing the microRNA profile with a reference to identify differentially expressed microRNA sequences. Based on the identity or the levels of the differentially expressed microRNA sequences, the physiological condition could be detected, predicted, or monitored; or a treatment could be indicated, administered, or monitored accordingly.

The biological sample is generally non-invasive, and may be, for example, a biopsy material, tissue, or body fluid. Exemplary body fluids include serum, plasma, lymph, saliva, urine, tears, sweat, semen, synovial fluid, cervical mucus, amniotic fluid, cerebrospinal fluid, and breast milk.

Combinations of different biological samples are also contemplated for providing more specific diagnoses. For example, plasma and serum would provide some general indicators of health, while a specific body fluid could be included for specific information. For example, if one wanted to assess the health status of a fetus being carried by the mother, one might test the amniotic fluid along with the mother's plasma or serum. As another example, one might test the urine to assess the health status of a bladder or a kidney. Testing the breast milk would help assess the health status of a breast of the patient providing the biological sample. Testing the saliva would help assess the health status of the head and neck region. Testing the tears would help assess the health status of an eye of the patient providing the biological sample. Testing semen would help assess the health status of a prostate or male reproductive organ. Testing the synovial fluid would help assess the health status of a joint of the patient providing the biological sample. Testing the sweat would help assess the health status of the skin. Testing the cerebrospinal fluid would help assess the health status of the central nerve system. The term "health status" refers only to the physiological condition of the given body part, and has no specific meaning otherwise.

Isolating microRNA can be done by various methods. For example, the biological sample may be extracted with an organic solvent to obtain an aqueous phase containing the microRNA sequences. The aqueous phase is then purified through a silica membrane to isolate the microRNA sequences.

A microRNA profile can then be generated from the isolated microRNA sequences. Generally speaking, the microRNA profile provides the identity of specific microRNA sequences and/or the expression level (i.e. amount) of each specific microRNA sequence. An exemplary microRNA profile is seen in FIG. 2, which shows the expression levels for several microRNA sequences from several different liver samples that have been exposed to a high dose of acetaminophen. The microRNA profile of FIG. 2 has six columns, but a microRNA profile may be simply one column (along with the identifying microRNA). The expression level can be displayed either as a sliding color scale or simply as numerical values. The microRNA profile can be generated by using hybridization to identify the microRNA sequences and/or using quantitative PCR (qPCR) to identify the levels of one or more particular microRNA sequences. It should be noted that the diagnostic information may be in the identity of the microRNA sequences themselves, or in the absolute or relative levels of the microRNA sequence, either between two microRNA sequences in a given sample or between two samples for a given microRNA sequence. A reference table could be provided, for example from a reference sample taken from the patient or from a table of levels of expressed microRNA sequences in a normal (healthy) person or a table compiled from the expressed microRNA sequences over a large sample of people. Differentially expressed microRNA sequences can then be identified by comparing the microRNA profile of the biological sample with the reference sample or table to obtain diagnostic information. The term "differentially expressed" refers only to the fact that the amount or expression level has changed. The direction of change (i.e. upwards or downwards, overexpressed or underexpressed) is not significant, except as otherwise stated.

In particular embodiments, it is contemplated that identifying at least one specific microRNA sequence as being differentially expressed would be sufficient to identify a particular physiological condition as occurring. In other embodiments, at least two differentially expressed microRNA sequences are identified. This provides for an additional degree of confirmation in the identity of the physiological condition.

In using the terms "generating" and "identifying," it is contemplated that these actions may be performed directly or indirectly. For example, a laboratory technician may perform the actions that directly "generate" a microRNA profile. The physician who ordered the microRNA profile that was directly "generated" by the laboratory technician may be considered to have indirectly "generated" the microRNA profile.

Because microRNA sequences and expression levels are generally conserved across species, it is contemplated that sequences and levels from other species would contain useful diagnostic information. For example, the biological sample may be from a microbe, such as a virus, bacterium, fungus, protozoan, or parasite.

It has been found that microRNA sequences and their expression levels can differ depending on their location in the body. In other words, they can be specific to a biological pathway, cell type, or tissue. This fact can provide powerful diagnostic information as well.

Table 1 lists some microRNA sequences which have been found to be specific to certain tissues in the human body.

TABLE 1

| Tissue | Human tissue specific miRNA | Tissue | Human tissue specific miRNA |
| --- | --- | --- | --- |
| Adipose | hsa-miR-452 | Placenta | hsa-miR-527 |
| Adipose | hsa-miR-196a | Placenta | hsa-miR-377 |
| Adipose | hsa-miR-224 | Placenta | hsa-miR-526c |
| Adipose | hsa-miR-335 | Placenta | hsa-miR-524* |
| Adipose | hsa-miR-452* | Placenta | hsa-miR-517* |
| Adipose | hsa-miR-432* | Placenta | hsa-miR-450 |
| Adrenal | hsa-miR-409-5p | Placenta | hsa-miR-503 |
| Adrenal | hsa-miR-494 | Placenta | hsa-miR-526b* |
| Adrenal | hsa-miR-485-5p | Placenta | hsa-miR-371 |
| Adrenal | hsa-miR-360-5p | Placenta | hsa-miR-519b |
| Adrenal | hsa-miR-154 | Placenta | hsa-miR-516-3p |
| Adrenal | hsa-miR-370 | Placenta | hsa-miR-526a |
| Adrenal | hsa-miR-381 | Placenta | hsa-miR-523 |
| Adrenal | hsa-miR-369 | Placenta | hsa-miR-518a-2* |
| Adrenal | hsa-miR-485-3p | Placenta | hsa-miR-518c* |
| Adrenal | hsa-miR-134 | Placenta | hsa-miR-520b |
| Adrenal | hsa-miR-323 | Placenta | hsa-miR-518d |
| Adrenal | hsa-miR-7N | Placenta | hsa-miR-524 |
| Adrenal | hsa-miR-382 | Placenta | hsa-miR-519a |
| Adrenal | hsa-miR-7 | Placenta | hsa-miR-520a |
| Adrenal | hsa-miR-405 | Placenta | hsa-miR-521 |
| Adrenal | hsa-miR-127 | Placenta | hsa-miR-522 |
| Adrenal | hsa-miR-493 | Placenta | hsa-miR-520d |
| Adrenal | hsa-miR-379 | Placenta | hsa-miR-525 |
| Adrenal | hsa-miR-432 | Placenta | hsa-miR-512-5p |
| Adrenal | hsa-miR-299 | Placenta | hsa-miR-520a* |
| Adrenal | hsa-miR-433 | Placenta | hsa-miR-519a* |
| Adrenal | hsa-miR-376a | Placenta | hsa-miR-517a |
| Adrenal | hsa-miR-202* | Placenta | hsa-miR-517b |
| Adrenal | hsa-miR-137 | Placenta | hsa-miR-515-5p |
| Adrenal | hsa-miR-501 | Placenta | hsa-miR-525* |
| Adrenal | hsa-miR-202 | Placenta | hsa-miR-518 |
| Adrenal | hsa-miR-491 | Placenta | hsa-miR-512-3p |
| Bladder | hsa-miR-451 | Placenta | hsa-miR-517c |
| Brain | hsa-miR-330 | Placenta | hsa-miR-518a |
| Brain | hsa-miR-219 | Placenta | hsa-miR-519d |
| Brain | hsa-miR-124 | Placenta | hsa-miR-518c |
| Brain | hsa-miR-9 | Placenta | hsa-miR-518e |
| Brain | hsa-miR-9* | Placenta | hsa-miR-520g |
| Brain | hsa-miR-124a | Placenta | hsa-miR-519c |
| Brain | hsa-miR-129 | Placenta | hsa-miR-515-3p |
| Brain | hsa-miR-124b | Placenta | hsa-miR-520b |
| Brain | hsa-miR-137 | Placenta | hsa-miR-372 |
| Brain | hsa-miR-383 | Placenta | hsa-miR-520a |
| Brain | hsa-miR-433 | Placenta | hsa-miR-520c |
| Brain | hsa-miR-348 | Placenta | hsa-miR-373 |
| Brain | hsa-miR-323 | Placenta | hsa-miR-520b |
| Brain | hsa-miR-153 | Placenta | hsa-miR-154* |
| Brain | hsa-miR-128b | Placenta | hsa-miR-520c |
| Brain | hsa-miR-128a | Placenta | hsa-miR-493 |
| Brain | hsa-miR-485-5p | Placenta | hsa-miR-381 |
| Brain | hsa-miR-370 | Placenta | hsa-miR-151 |
| Brain | hsa-miR-485-3p | Placenta | hsa-miR-495 |
| Brain | hsa-miR-181b | Placenta | hsa-miR-474 |
| Brain | hsa-miR-338 | Placenta | hsa-miR-369-5p |
| Brain | hsa-miR-154* | Placenta | hsa-miR-184 |
| Brain | hsa-miR-149 | Placenta | hsa-miR-489 |
| Brain | hsa-miR-213 | Placenta | hsa-miR-376a |
| Brain | hsa-miR-340 | Placenta | hsa-miR-500 |
| Brain | hsa-miR-181bN | Placenta | hsa-miR-369 |
| Brain | hsa-miR-181d | Placenta | hsa-miR-135b |
| Brain | hsa-miR-491 | Placenta | hsa-miR-432 |
| Brain | hsa-miR-184 | Placenta | hsa-miR-27aN |
| Brain | hsa-miR-138 | Placenta | hsa-miR-198 |
| Brain | hsa-miR-132 | Placenta | hsa-miR-224 |
| Brain | hsa-miR-181c | Placenta | hsa-miR-452* |
| Brain | hsa-miR-204 | Placenta | hsa-miR-433 |
| Brain | hsa-miR-328 | Placenta | hsa-miR-193b |
| Brain | hsa-miR-181a | Placenta | hsa-miR-494 |
| Brain | hsa-miR-432 | Placenta | hsa-miR-502 |
| Brain | hsa-miR-379 | Placenta | hsa-miR-335 |
| Brain | hsa-miR-324-5p | Placenta | hsa-miR-299 |
| Brain | hsa-miR-122 | Placenta | hsa-miR-149 |
| Brain | hsa-miR-134 | Placenta | hsa-miR-213 |
| Brain | hsa-miR-342 | Placenta | hsa-miR-30d |
| Breast | hsa-miR-452 | Placenta | hsa-miR-141 |
| Breast | hsa-miR-205 | Placenta | hsa-miR-301 |
| Breast | hsa-miR-489 | Placenta | hsa-miR-485-3p |
| Colon | hsa-miR-490 | Placenta | hsa-miR-141N |
| Colon | hsa-miR-363 | Placenta | hsa-miR-379 |
| Colon | hsa-miR-338 | Placenta | hsa-miR-130a |

TABLE 1-continued

| Tissue | Human tissue specific miRNA | Tissue | Human tissue specific miRNA |
|---|---|---|---|
| Colon | hsa-miR-31 | Placenta | hsa-miR-382 |
| Colon | hsa-miR-215 | Placenta | hsa-miR-99b |
| Colon | hsa-miR-200a* | Placenta | hsa-miR-370 |
| Colon | hsa-miR-200a | Placenta | hsa-miR-130b |
| Colon | hsa-miR-196b | Placenta | hsa-miR-27a |
| Colon | hsa-miR-196a | Placenta | hsa-miR-200cN |
| Colon | hsa-miR-194 | Placenta | hsa-miR-24 |
| Colon | hsa-miR-192 | Placenta | hsa-miR-30a-5p |
| Colon | hsa-miR-141N | Placenta | hsa-miR-30bN |
| Colon | hsa-miR-141 | Placenta | hsa-miR-221 |
| Small Intestine | hsa-miR-490 | Placenta | hsa-miR-200c |
| Small Intestine | hsa-miR-451 | Placenta | hsa-miR-320 |
| Small Intestine | hsa-miR-429 | Placenta | hsa-miR-127 |
| Small Intestine | hsa-miR-31 | Placenta | hsa-miR-485-5p |
| Small Intestine | hsa-miR-215 | Placenta | hsa-miR-30b |
| Small Intestine | hsa-miR-200bN | Placenta | hsa-miR-90a-3p |
| Small Intestine | hsa-miR-200b | Placenta | hsa-miR-181a |
| Small Intestine | hsa-miR-200a* | Placenta | hsa-miR-222 |
| Small Intestine | hsa-miR-198 | Placenta | hsa-miR-362 |
| Small Intestine | hsa-miR-194 | Placenta | hsa-miR-125a |
| Small Intestine | hsa-miR-192 | Placenta | hsa-miR-323 |
| Small Intestine | hsa-miR-138 | Placenta | hsa-miR-451 |
| Cervix | hsa-miR-196b | Placenta | hsa-miR-409-5p |
| Cervix | hsa-miR-99a | Placenta | hsa-miR-452 |
| Heart | hsa-miR-1 | Placenta | hsa-miR-518b |
| Heart | hsa-miR-107 | Placenta | hsa-miR-515-5p |
| Heart | hsa-miR-133a | Placenta | hsa-miR-130aN |
| Heart | hsa-miR-189 | Skeletal Muscle | hsa-miR-206 |
| Heart | hsa-miR-221 | Skeletal Muscle | hsa-miR-95 |
| Heart | hsa-miR-23bN | Skeletal Muscle | hsa-miR-133b |
| Heart | hsa-miR-302a | Skeletal Muscle | hsa-miR-133a |
| Heart | hsa-miR-302b | Skeletal Muscle | hsa-miR-128b |
| Heart | hsa-miR-302c | Skeletal Muscle | hsa-miR-1 |
| Heart | hsa-miR-302d | Skeletal Muscle | hsa-miR-489 |
| Heart | hsa-miR-300-3p | Skeletal Muscle | hsa-miR-378 |
| Heart | hsa-miR-367 | Skeletal Muscle | hsa-miR-422a |
| Heart | hsa-miR-378 | Skeletal Muscle | hsa-miR-128a |
| Heart | hsa-miR-422a | Skeletal Muscle | hsa-miR-196a |
| Heart | hsa-miR-422b | Skeletal Muscle | hsa-miR-502 |
| Heart | hsa-miR-452 | Spleen | hsa-miR-223 |
| Heart | hsa-miR-490 | Spleen | hsa-miR-139 |
| Heart | hsa-miR-491 | Lymph Node | hsa-miR-150 |
| Heart | hsa-miR-409 | Lymph Node | hsa-miR-142-3p |
| Heart | hsa-miR-7a | Lymph Node | hsa-miR-146b |
| Pericardium | hsa-miR-188 | Lymph Node | hsa-miR-146 |
| Pericardium | hsa-miR-369 | Lymph Node | hsa-miR-155 |
| Pericardium | hsa-miR-305 | Lymph Node | hsa-miR-363 |
| Pericardium | hsa-miR-452 | PBMC | hsa-miR-128a |
| Pericardium | hsa-miR-224 | PBMC | hsa-miR-124b |
| Pericardium | hsa-miR-511 | PBMC | hsa-miR-124a |
| Pericardium | hsa-miR-199b | PBMC | hsa-miR-137 |
| Kidney | hsa-miR-500 | PBMC | hsa-miR-431 |
| Kidney | hsa-miR-204 | PBMC | hsa-miR-129 |
| Kidney | hsa-miR-480 | PBMC | hsa-miR-128b |
| Kidney | hsa-miR-190 | PBMC | hsa-miR-138 |
| Kidney | hsa-miR-501 | Thymus | hsa-miR-183 |
| Kidney | hsa-miR-196a | Thymus | hsa-miR-96 |
| Kidney | hsa-miR-211 | Thymus | hsa-miR-128b |
| Kidney | hsa-miR-363 | Thymus | hsa-miR-213 |
| Kidney | hsa-miR-502 | Thymus | hsa-miR-205 |
| Kidney | hsa-miR-184 | Thymus | hsa-miR-128a |
| Liver | hsa-miR-122a | Thymus | hsa-miR-181bN |
| Liver | hsa-miR-30a-3p | Thymus | hsa-miR-182 |
| Lung | hsa-miR-223 | Thymus | hsa-miR-181b |
| Esophagus | hsa-miR-203 | Thymus | hsa-miR-181d |
| Esophagus | hsa-miR-205 | Thymus | hsa-miR-181a |
| Esophagus | hsa-miR-145 | Thymus | hsa-miR-181c |
| Esophagus | hsa-miR-210N | Thymus | hsa-miR-20b |
| Esophagus | hsa-miR-143 | Thymus | hsa-miR-383 |
| Esophagus | hsa-miR-31 | Thymus | hsa-miR-17-5p |
| Esophagus | hsa-miR-187 | Thymus | hsa-miR-142-3p |
| Trachea | hsa-miR-34b | Stomach | hsa-miR-211 |
| Trachea | hsa-miR-205 | Stomach | hsa-miR-188 |
| Trachea | hsa-miR-34cN | Stomach | hsa-miR-346 |
| Trachea | hsa-miR-34c | Stomach | hsa-miR-200a* |
| Prostate | hsa-miR-363 | Stomach | hsa-miR-375 |
| Prostate | hsa-miR-205 | Stomach | hsa-miR-148a |
| Prostate | hsa-miR-196b | Stomach | hsa-miR-200a |
| Ovary | hsa-miR-502 | Stomach | hsa-miR-200b |
| Ovary | hsa-miR-383 | Stomach | hsa-miR-200c |
| Fallopian Tube | hsa-miR-34bN | Stomach | hsa-miR-200bN |
| Fallopian Tube | hsa-miR-34b | Stomach | hsa-miR-212 |
| Fallopian Tube | hsa-mi-34cN | Stomach | hsa-miR-31 |
| Fallopian Tube | hsa-miR-449 | Stomach | hsa-miR-7 |
| Fallopian Tube | hsa-miR-34c | Stomach | hsa-miR-153 |
| Fallopian Tube | hsa-miR-135a | Stomach | hsa-miR-429 |
| Pancreas | hsa-miR-217 | Stomach | hsa-miR-107 |
| Pancreas | hsa-miR-216 | Stomach | hsa-miR-200cN |
| Pancreas | hsa-miR-375 | Stomach | hsa-miR-502 |
| Pancreas | hsa-miR-98 | Stomach | hsa-miR-203 |
| Pancreas | hsa-miR-163 | Testicle | hsa-miR-202 |
| Pancreas | hsa-miR-141N | Testicle | hsa-miR-506 |
| Pancreas | hsa-miR-148a | Testicle | hsa-miR-507 |
| Pancreas | hsa-miR-141 | Testicle | hsa-miR-510 |
| Pancreas | hsa-miR-7N | Testicle | hsa-miR-514 |
| Pancreas | hsa-miR-494 | Testicle | hsa-miR-513 |
| Pancreas | hsa-miR-130b | Testicle | hsa-miR-508 |
| Pancreas | hsa-miR-200cN | Testicle | hsa-miR-509 |
| Pancreas | hsa-miR-148b | Testicle | hsa-miR-202* |
| Pancreas | hsa-miR-182 | Testicle | hsa-miR-449 |
| Pancreas | hsa-miR-200a | Testicle | hsa-miR-34c |
| Thyroid | hsa-miR-138 | Testicle | hsa-miR-432* |
| Thyroid | hsa-miR-135a | Testicle | hsa-miR-184 |
| Thyroid | hsa-miR-206 | Testicle | hsa-miR-520c |
| Thyroid | hsa-miR-95 | Testicle | hsa-miR-520I |
| Thyroid | hsa-miR-1 | Testicle | hsa-miR-34cN |
| Thyroid | hsa-miR-7 | Testicle | hsa-miR-34b |
| Uterus | hsa-miR-10b | Testicle | hsa-miR-520b |
| Uterus | hsa-miR-196b | Testicle | hsa-miR-135b |
| Uterus | hsa-miR-502 | Testicle | hsa-miR-383 |
| Testicle | hsa-miR-204 | Testicle | hsa-miR-34bN |

It has been found that microRNA sequences and their expression levels can differ depending on their location in different types of body fluid samples. In other words, they can be specific to a biological pathway, cell type, or tissue. This fact can provide powerful diagnostic information as well.

Table 2 lists some microRNA sequences which have been found to be highly abundant in different body fluids. The sequences in bold font are unique to the listed body fluid.

TABLE 2

| Tears | Urine | Breast Milk | Seminal Fluid | Saliva | Amniotic Fluid |
|---|---|---|---|---|---|
| miR-518e | miR-515-3p | miR-518e | miR-518e | miR-335* | miR-518e |
| miR-335* | miR-335* | miR-26a-2* | miR-590-3p | miR-515-3p | miR-335* |
| miR-137 | miR-892a | miR-335* | miR-588 | miR-545* | miR-302c |
| miR-515-3p | miR-509-5p | miR-490-5p | miR-873 | miR-492 | miR-515-3p |
| miR-509-5p | miR-223* | miR-181d | miR-590-5p | miR-892a | miR-452 |
| miR-873 | miR-302d | miR-26a-1* | miR-137 | miR-518e | miR-892a |
| miR-223* | miR-873 | miR-137 | miR-197 | miR-27a | miR-671-5p |
| miR-892a | miR-923 | miR-524-5p | miR-515-5p | miR-923 | miR-515-5p |
| miR-590-3p | miR-616* | miR-509-5p | miR-515-3p | miR-509-5p | miR-590-3p |
| miR-302d | miR-483-5p | miR-513c | miR-218 | miR-873 | miR-593* |
| miR-616* | miR-134 | miR-595 | miR-20b | miR-483-5p | miR-873 |
| miR-590-5p | miR-589 | miR-515-3p | miR-410 | miR-616* | miR-137 |
| miR-101* | miR-556-3p | miR-515-5p | miR-335* | miR-580 | miR-410 |
| miR-130a | miR-101* | miR-598 | miR-617 | miR-609 | miR-548d-5p |
| miR-410 | miR-138 | miR-130a | miR-671-5p | miR-302d | miR-223* |
| miR-195 | miR-652 | miR-181b | miR-524-5p | miR-25* | miR-590-5p |
| miR-675 | miR-325 | miR-671-5p | miR-892a | miR-134 | miR-616* |
| miR-325 | let-7i | miR-892a | miR-181d | miR-92b | miR-302d |
| miR-134 | miR-377* | miR-578 | miR-545* | miR-598 | miR-509-5p |
| miR-29b | miR-545* | miR-580 | miR-1 | let-7a | miR-210 |

| Bronchial Lavage | CSF | Pleural Fluid | Peritoneal Fluid | Colostrum | Plasma |
|---|---|---|---|---|---|
| miR-515-3p | miR-515-3p | miR-515-3p | miR-892a | miR-509-5p | miR-335* |
| miR-335* | miR-335* | miR-892a | miR-518e | miR-181d | miR-325 |
| miR-509-5p | miR-892a | miR-509-5p | miR-515-3p | miR-335* | miR-377* |
| miR-483-5p | miR-223* | miR-134 | miR-134 | miR-518e | miR-586 |
| miR-892a | miR-873 | miR-590-5p | miR-509-5p | miR-515-5p | miR-518e |
| miR-223* | miR-509-5p | miR-515-5p | miR-223* | miR-223* | let-7i |
| miR-873 | miR-302d | miR-873 | miR-515-5p | miR-671-5p | miR-539 |
| miR-1225-3p | miR-616* | miR-335* | miR-616* | miR-873 | miR-616* |
| miR-302d | miR-134 | miR-920 | miR-137 | miR-483-5p | miR-302d |
| miR-545* | miR-483-5p | miR-616* | miR-873 | miR-186 | miR-589 |
| miR-324-3p | miR-325 | miR-302d | miR-483-5p | miR-515-3p | miR-556-3p |
| miR-616* | miR-151-5p | miR-518e | miR-518c | miR-616* | miR-151-3p |
| miR-92b | miR-589 | miR-923 | miR-92b | miR-134 | miR-548b-3p |
| miR-25* | miR-377* | miR-589 | miR-923 | miR-892a | miR-192 |
| miR-539 | miR-923 | miR-377* | miR-302d | miR-590-5p | miR-151-5p |
| miR-923 | miR-652 | miR-410 | miR-374a | miR-590-3p | miR-598 |
| miR-192 | miR-518e | miR-137 | miR-598 | miR-425 | miR-187 |
| miR-134 | miR-556-3p | miR-671-5p | miR-937 | miR-454 | miR-873 |
| miR-371-3p | miR-767-3p | miR-151-5p | miR-335* | miR-101* | miR-218 |
| miR-580 | miR-505 | miR-223* | miR-885-5p | miR-132 | miR-923 |

With the diagnostic information obtained, a physiological condition could be detected, identified, predicted, treated, and/or monitored. For example, a treatment could be administered based on the identity of the physiological condition. A particular treatment could be monitored by taking a first sample, administering the treatment, taking a second sample, and comparing the microRNA profiles of the two samples to identify and/or track changes resulting from the treatment. Those changes could include the amounts of a particular microRNA sequence, or the identity of the differentially expressed microRNA sequences that have changed between the two samples.

It is also contemplated that manipulating the levels of microRNA sequences might itself be a treatment for a physiological condition. The microRNA level could be altered by constructing a specific DNA or RNA sequence related to the microRNA sequences, then delivering that DNA or RNA sequence to a targeted cell, tissue, or organ expressing the targeted microRNA sequences.

As discussed below, specific microRNA sequences are identified that may be useful in diagnosing and/or treating liver disease or injury, lung disease or injury, and neurological disease or injury. Such conditions include chronic obstructive pulmonary disease (COPD) and idiopathic pulmonary fibrosis (IPF) (also known as interstitial lung disease (ILD)).

Other methods embodied herein include generating a microRNA profile from a biological sample. The microRNA profile comprises the amounts of specific microRNA sequences. The amounts of those specific microRNA sequences are then compared to a reference to provide information for detecting or predicting the lung condition. In this regard, the microRNA profile may include those specific microRNA sequences identified below in the examples, or a subset thereof. Such microRNA profiles would be smaller, faster, and provide the same diagnostic information as larger test kits.

The following examples are provided to illustrate the devices and methods of the present disclosure. The examples are merely illustrative and are not intended to limit the disclosure to the materials, conditions, or process parameters set forth therein.

EXAMPLES

Isolation of microRNA microRNA can be isolated using glass filter based methods to selectively bind RNA in a high salt buffer. The unwanted biomolecules can then be washed off by using high salt buffers containing at least 50% alcohol. The bound pure RNA can then eluted off the glass membrane with low salt buffer or RNAse-free water.

1). Isolating microRNA from Solid Tissues

Briefly, total RNA, including microRNA, was isolated using commercial kits such as miRNeasy mini kit (Qiagen Inc. Valencia, Calif.). Approximately 5 mg to 50 mg tissue samples were excised from flash-frozen tissue. After placing the tissue sample into a Dounce tissue grinder, 700 microliter (μl) QIAzol lysis reagent was added to the grinder and the tissue was homogenized immediately. For every 700 μl QIAzol lysis reagent used, 140 μl chloroform was added to the tissue lysate to extract the water soluble content. After mixing for 15 seconds, the lysate was placed in a centrifuge and spun at 12000×g for 15 minutes at room temperature. The upper aqueous phase (containing the RNA) was then transferred to a new collection tube, and 1.5 volumes of ethanol was added. The sample was then transferred to a cartridge containing a glass filter (i.e. silica membrane) so that RNA could attach to the glass filter. The contaminants were washed off the silica membrane by applying different high salt washing buffers included in the miRNeasy kit. The bound pure RNA was then eluted off the membrane with water or low salt buffer.

2). Isolating microRNA from Liquid Samples

Approximately, 800 μl of QIAzol lysis reagent was added to 200 μl liquid sample. The sample was mixed in a tube followed by adding 200 μl of chloroform. After mixing rigorously for 15 seconds, the sample was then centrifuged at 12,000×g for 15 minutes. The upper aqueous phase was carefully transferred to a new collection tube, and 1.5 total volumes of ethanol was added. The sample was then applied directly to a glass membrane containing column and the RNA was bound and purified by three contiguous washing to remove unwanted contamination. The immobilized RNA was then collected from the membrane with a low salt elution buffer.

The yield of microRNA from different amount of liquid samples used in these protocols was tested. The best ratio was found to be 4 volumes of lysis buffer with 1 volume of liquid sample.

The quality and quantity of RNA isolated was evaluated by RNA by NanoDrop 1000 spectrophotometer (Thermo Fisher Scientific Inc. Waltham, Mass.) and the Agilent 2100 Bioanalyzer (Agilent Inc. Santa Clara, Calif.).

Figure 1A:
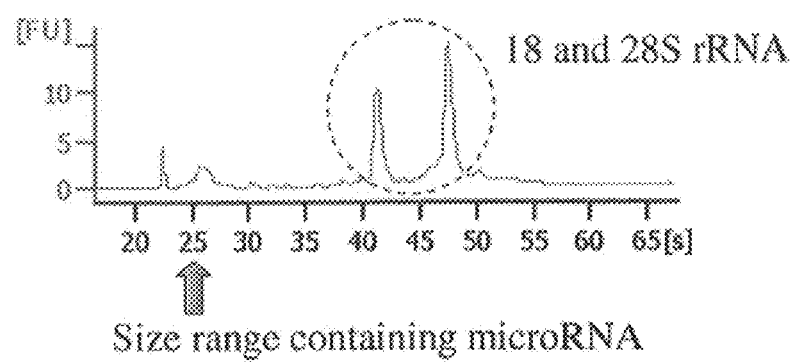
FIGS. 1A-1B are electropherograms of RNA.
Figure 1B:
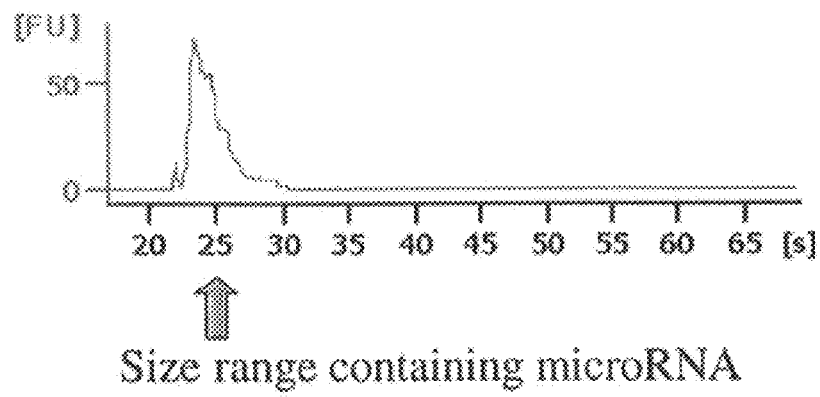

FIG. 1A shows an electropherogram of RNA isolated from solid tissue, while FIG. 1B shows an electropherogram of RNA isolated from a liquid sample. The 18S and 28S peaks are clearly visible and marked. The microRNA are located on the left of both electropherograms. This region also contains all degraded RNA.

Array Hybridization and Quantitative PCR

Agilent's human and mouse microRNA microarray kits (Agilent Inc. Santa Clara, Calif.) were used as the array platform; however, arrays from different companies including Affymetrix and Exiqon have also been used. The human microRNA microarray contained probes for 723 human and 76 human viral microRNAs from the Sanger database v 10.1. The mouse microRNA microarray contained probes for 567 mouse and 10 mouse herpes virus microRNA sequences from the Sanger database v 10.1. Cyanine 3-pCp labeled RNA (i.e. RNA labeled with Cyanine 3-Cytidine bisphosphate) for array hybridization was generated by 100 nanograms (ng) of total RNA using Agilent's microRNA complete labeling and hybridization kit. All the steps, including labeling, hybridization, washing, scanning and feature extraction were performed in accordance with the manufacturer's instructions.

In brief, 100 ng of total RNA was dephosphorylated with calf intestinal alkaline phosphatase, then heat and DMSO treated to yield denatured RNA. Cyanine 3-Cytidine bisphosphate was joined to the microRNA by T4 RNA ligase. MicroBioSpin 6 columns were used to desalt the samples and remove any unincorporated fluorophores. The samples were hybridized to 8×15K Agilent Human microRNA (V2) or Mouse microRNA microarrays in a rotating hybridization oven for 20 hours at 55° C. and 10 rpm. The arrays were washed for 5 minutes in Agilent GE Wash Buffer 1 with Triton X-102 and then for another 5 minutes in Agilent GE Wash Buffer 2 with Triton X-102.

After washing, all slides were immediately scanned using a PerkinElmer ScanArray Express at 5 micron resolution. The resulting images were quantified using Agilent's Feature Extraction software. The differentially expressed microRNA sequences were then identified using a standard protocol developed for gene array data processing. The sample or gene clustering and array hybridization heatmap were generated using MeV4 software package from The Institute for Genomic Research (TIGR) (available at http://www.tigr.org/tdb/microarray/).

Quantitative PCR (QPCR) with microRNA specific primer sets were used to confirm the results from array hybridization. In brief, a SYBR Green based method, miScript real-time PCR (Qiagen Inc. Valencia, Calif., USA), or TaqMan primer set from Apply Biosystems, was used with 50 ng of total RNA from each sample. The first strand cDNA was generated according to the manufacturer's instruction. Approximately 2.5 ng of cDNA was used in the PCR reaction. The yield of 18 to 20 base pair fragments (based on SYBR Green intensity) corresponding to the specific microRNA species was monitored with the 7900HT fast real-time PCR system from Applied Biosystems (Applied Biosystems, Foster City, Calif.). QPCR results were analyzed by SDS 2.2.2, with a manual $C_T$ threshold value of 0.2.

Example 1

This example showed that microRNA sequences could be used as a marker to detect liver injury. Mice were used as the experimental model.

6-month-old male C57/B6 mice were grouped into control and treatment groups with 4 animals in each group. The mice then fasted for 24 hours prior to a single intraperitoneal injection of either (a) 300 mg/kg of acetaminophen in phosphate buffer saline (PBS) (treatment group); (b) or PBS (control group). Mice were sacrificed at different time points post-exposure (12 hr, 24 hr, 48 hr, 72 hr, and 120 hr) and plasma and liver samples were collected. Part of the liver samples were sectioned and examined by a pathologist and the serum alanine transaminase (ALT) levels were also determined to confirm as well as assess the severity of liver injury.

Total RNA was isolated from collected samples to conduct comprehensive microRNA analyses. To assess the level of microRNA in liver tissues, a microRNA array from Agilent was used. The RNA samples were labeled and processed according to the manufacturer's recommended protocols. The data from each array were extracted, normalized and compared following a standard gene expression microarray method.

The expression levels of various microRNA sequences in the liver tissues were used to generate a microRNA profile and used to assess tissue injury. Differentially expressed microRNA sequences were clustered using the Hierarchical clustering method and the result is shown in FIG. 2. The different time points are indicated on the top, while the identity of individual microRNA sequences is listed on the right. (The identifying labels correspond to those in the miRNA Registry maintained at the Sanger Institute.) The hybridization intensity of individual microRNA sequences is represented in different colors as indicated on top of the figure (yellow representing the highest expression and blue representing the lowest expression signal). The microRNA profile clearly indicates that the levels of some microRNA sequences were changed by the exposure to acetaminophen.

Example 2

This example showed that the levels of specific microRNA sequences in the serum or plasma could be used to assess drug-induced liver injury.

The male C57/B6 mice were randomly grouped into two groups, a treatment group (3 animals) and control group (4 animals). They fasted for 24 hours prior to a single intraperitoneal injection of either (a) 300 mg/kg of acetaminophen in PBS (treatment group); or (b) PBS (control group). Mice were sacrificed at 24 hours post exposure, the plasma samples were collected and RNA was isolated.

The expression levels of microRNA sequences in the serum were used to make a microRNA profile. The differentially expressed microRNA sequences between the treatment group and the control group were clustered with the Hierarchical clustering method and is shown in FIG. 3. The result clearly indicated that the levels of certain microRNA sequences in the serum could be used as an indication of the acetaminophen toxicity.

Example 3

This example showed that the levels of specific microRNA sequences in the serum or plasma could be used as an early indication of drug-induced liver injury.

The male C57/B6 mice were randomly grouped into nine different groups with 4 animals in each group. They fasted for 24 hours prior to a single intraperitoneal injection with either (a) 75 mg/Kg of acetaminophen in PBS (treatment 1); (b) 150 mg/Kg of acetaminophen in PBS (treatment 2); (c) 300 mg/Kg of acetaminophen in PBS (treatment 3); or (d) PBS (control group). Mice were sacrificed and plasma samples were collected at 1, 3 and 24 hours post-exposure. The nine groups were: 1) 1 hour control; 2) 1 hour treatment 1; 3) 1 hour treatment 2; 4) 1 hour treatment 3; 5) 3 hour control; 6) 3 hour treatment 1; 7) 3 hour treatment 2; 8) 3 hour treatment 3; and 9) 24 hour treatment 3. The group at 24 hr post-exposure received only the highest dose (300 mg/kg) to serve as a positive control. The expression levels of two different microRNA sequences, mir-486 and mir-122, in the serum were profiled by quantitative polymerase chain reactions (Q-PCR).

The median intensities (Z-axes) from each group (X-axis) at PCR cycle number 19 were plotted. This graph is shown in FIG. 4. Both mir-486 (red bars) and mir-122 (green bars) intensities showed dose-dependent changes at 3 hr post-exposure. The intensity of mir-122 at 300 mg/kg was almost the same between 3 hr and 24 hr post-exposure. Clear changes were observed in the samples obtained at one hour post-acetaminophen injection. The results clearly indicated that the levels of selected microRNA sequences, such as mir-122 and mir-486, in the serum could be used as an early indication of tissue injury.

Next, the ratios of the median intensities (green bars) and average intensities (blue bars) from each group at PCR cycle number 19 were plotted. This graph is shown as FIG. 5. As expected, the ratios of both median and average intensities showed dose-dependent changes at 3 hr post-exposure. The ratio also clearly indicated the difference between 3 hr and 24 hr post-exposure. This result clearly indicated the ratio of selected microRNA sequences, such as mir-122 and mir-486, in the serum could be used as an early indication of tissue injury.

Example 4

This example showed that microRNA could be used in assessing neurological disorders. The microRNA expression patterns in brain tissues obtained from normal and prion infected animals were profiled as described above. The results are shown in FIG. 6. The result clearly indicated differences between normal and diseased samples.

Example 5

This example showed that microRNA could be used in assessing the health status of lungs. The microRNA expression patterns in lung tissues obtained from normal and diseased animals were profiled as described above. The results are shown in FIG. 7. The result clearly indicated there were differences on microRNA expression as the disease progressed (from 1 to 6 where 6 has the most serious disease condition) and a number of microRNA sequences are different between normal and disease samples. Thus, specific microRNA sequences or a panel of microRNA sequences could be used as a tool to assess the health status of lungs.

Example 6

This example showed that different biological pathways or compartments had very different microRNA profiles. The microRNA profiles in serum and urine samples obtained from a normal mouse were profiled as described above, then compared. The result is shown in FIG. 8. The result clearly revealed a significant difference in the microRNA composition in different body fluids. This would allow the development of different biomarkers to be used in different body fluids to assess the health status of tissues. In addition, microRNA sequences in a specific body fluid can be used as a reliable tool to assess the health status of tissues intimately associated with that body fluid, e.g. bladder and kidney tissues to the urine.

Example 7 miRNA profiles from lung tissue and plasma from ILD patients and COPD patients were compared to a control set of miRNA profiles from uninvolved lung tissue obtained from lung cancer resections (controls) and a control set of miRNA profiles from plasma samples obtained from clinically normal donors (collected by the Marsh lab). The miRNA profiles were compared in various pairwise combinations to determine which miRNA sequences were overexpressed and thus useful for diagnostic purposes. The miRNA profiles were obtained using a microarray kit available from Agilent, which generally detected a given miRNA with usually two independent oligonucleotide (oligo) targets and four or more in some cases.

FIG. 9 shows the graph comparing miRNA expression levels in control plasma with ILD plasma. Note the log scale. MiRNA with expression values that differ substantially between the two samples reside away from the diagonal line (i.e. y=x) that would represent equivalent expression in the two samples. This graph indicated that many miRNAs in ILD plasma are expressed at substantially higher levels than in the control plasma. There also appear to be a few miRNAs in the control profile that were expressed at relatively lower levels than in the ILD profile.

Next, in order to reduce the complexity of the data, the similarity of the signals returned by the different oligos that were present on the Agilent array and designed to detect a given miRNA were examined. For example, miRNA 1225-5p (i.e. mir-1225-5p) was about 3-fold over expressed in ILD plasma. For mir-1225-5p, four probe oligos were used in the Agilent array. FIG. 10A shows the signal in the ILD plasma samples (n=24). FIG. 10B shows the signal in the control plasma samples (n=6). As seen, all four probe oligos gave signals in the ILD and control plasma samples. In addition, the signal strengths were within a factor of about two to each other, even though these oligos differ slightly in sequence.

17 miRNA sequences were identified that appeared to be overexpressed in the ILD plasma samples. FIG. 11 shows the signal strength for all of the oligos that targeted these 17 sequences. The ILD plasma signals are shown as blue diamonds and the control plasma signals are shown as pink squares. As seen, the signal strengths for all of the independent oligo probes were reasonably close (i.e. within a factor of 2.5).

Since the signals from the independent probes were close, the data from all probes was combined. Then, the mean expression level for each miRNA was calculated and miRNA sequences which were relatively overexpressed in the ILD plasma samples were identified. (An alternative analysis path could have been to choose the data from one or two of the independent probes and identify overexpressed miRNA sequences based on that data.)

FIG. 12 shows the resulting graph with the mean and one standard deviation identified. Again, the ILD plasma signals are shown as blue diamonds and the control plasma signals are shown as pink squares. The expression of the displayed microRNAs was at least two-fold higher in the ILD plasma samples than in the control plasma samples (2× was an arbitrary value). Table 3 lists the specific data of FIG. 12.

hsa-miR-448 and hiss-miR-92-a-2* were just over the threshold for inclusion and showed low absolute expression. The standard deviation for hsa-miR-451 was rather large when all samples (n=24) were used. However, when one outlier was removed (n=23), the standard deviations improved, as did the ratios. hsa-miR-451 was expressed ten times higher in control plasma relative to ILD plasma.

One of the miRNAs that is overexpressed in control serum relative to ILD serum, in combination with a miRNA that is overexpressed in ILD serum relative to control serum, could be used in a simple "top scoring pair" test for ILD.

Example 8

Using the same data as in Example 7, the expression of miRNA in both ILD plasma and ILD tissue was examined. That graph is shown in FIG. 14. While many miRNAs that were expressed in ILD plasma had little or no expression in ILD tissue, most of those that were expressed in tissue had at

TABLE 3

| microRNA sequence | mean level (ILD) | St. Dev. (ILD) | mean level (control) | St. Dev. (control) | mean ILD/ mean control |
|---|---|---|---|---|---|
| hsv1-miR-H1 | 371 | 100 | 207 | 13.9 | 1.8 |
| hsa-miR-223 | 688 | 317 | 338 | 105 | 2.0 |
| hsa-miR-575 | 416 | 17 | 198 | 21.4 | 2.1 |
| hsa-miR-483-5p | 589 | 179 | 259 | 70.1 | 2.3 |
| hsa-miR-150* | 659 | 142 | 267 | 35.6 | 2.5 |
| hsa-miR-22 | 958 | 589 | 376 | 91 | 2.5 |
| hsa-miR-1225-5p | 3361 | 873 | 1201 | 324.4 | 2.8 |
| hsa-miR-939 | 644 | 463 | 224 | 36.5 | 2.9 |
| hsa-miR-135a* | 499 | 127 | 172 | 33.2 | 2.9 |
| hsa-miR-940 | 1316 | 906 | 341 | 45.6 | 3.9 |
| hsa-miR-134 | 830 | 9 | 201 | 50 | 4.1 |
| hcmv-miR-UL70-3p | 721 | 129 | 166 | 25.2 | 4.3 |
| hsa-miR-630 | 3349 | 65 | 683 | 100.3 | 4.9 |
| hsv1-miR-LAT | 1250 | 490 | 223 | 64.2 | 5.6 |
| kshv-miR-K12-3 | 3542 | 2912 | 588 | 422.3 | 6.0 |
| hsa-miR-638 | 18055 | 11123 | 1670 | 716.2 | 10.8 |
| hsa-miR-923 | 42215 | 40796 | 310 | 9883.1 | 136.2 |

Based on the standard deviations, the 17 miRNAs that met this criterion can be divided into three groups. 11 miRNAs (UL70-3p, 1225-5p, 134, 135a*, 150*, 483-5p, 575, 630, 638, H1, and LAT) were likely to be differentially expressed between ILD and control with high confidence. There was intermediate confidence for 4 miRNAs (mir-22, 223, 939, and 940); and lower confidence for miRNAs 923 and K12-3.

The degree of over expression displayed by these miRNAs varied over 100-fold, as shown in FIG. 13. Note the log scale.

Next, the miRNA that were expressed at a higher level in control plasma than ILD plasma were investigated. An arbitrary expression level of 250 or greater and 3.0 fold or greater relative overexpression as used to screen out marginal miRNA candidates. Three miRNA sequences passed this screen as shown in Table 4.

least some expression in plasma. Those miRNA sequences that had signal strength of at least 1000 in both tissue and plasma (an arbitrarily chosen value) are listed in Table 5. The ratio of the expression for the miRNA sequence was also compared to the average expression of all the miRNAs in the sample and is labeled as "overexpression ratio."

TABLE 5

| microRNA sequence | mean level (plasma) | overexpression ratio | mean level (tissue) | overexpression ratio |
|---|---|---|---|---|
| hsa-miR-1225-5p | 4043 | 9.8 | 1189.0 | 3.1 |
| hsa-miR-21 | 455 | 1.1 | 9938.7 | 26.0 |

TABLE 4

| microRNA sequence | mean level (ILD) | St. Dev. (ILD) | mean level (control) | St. Dev. (control) | mean control/ mean ILD |
|---|---|---|---|---|---|
| hsa-miR-451 oligo 1 | 729 | 1695.917 | 5274 | 5362.923 | 7 |
| hsa-miR-451; oligo 2 | 487 | 1096.762 | 3527.167 | 3421.076 | 7 |
| hsa-miR-451; oligo 1 w/o outlier | 390 | 375 | 5274 | | 13.5 |
| hsa-miR-451; oligo 2 w/o outlier | 268 | 243 | 3527 | | 13.1 |
| hsa-miR-448 | 64 | 38.3 | 253 | 93 | 4 |
| hsa-miR-92a-2* | 78 | 46.94568 | 253.6667 | 109.7154 | 3 |

TABLE 5-continued

| microRNA sequence | mean level (plasma) | overexpression ratio | mean level (tissue) | overexpression ratio |
|---|---|---|---|---|
| hsa-miR-22 | 1374 | 3.3 | 5555.8 | 14.5 |
| hsa-miR-223 | 835 | 2.0 | 1303.4 | 3.4 |
| hsa-miR-451 | 729 | 1.8 | 6564.4 | 17.2 |
| hsa-miR-638 | 25920 | 62.6 | 1084.6 | 2.8 |
| hsa-miR-923 | 71062 | 171.7 | 6114.7 | 16.0 |
| kshv-miR-K12-3 | 5602 | 13.5 | 498.0 | 1.3 | hsa-miR-21 was present here, but not in Tables 3 or 4, while the other seven were also listed in either Table 3 or 4.

Example 9

Using the same data as in Example 7, the expression of miRNA in both ILD lung tissue and control lung tissue was examined. That graph is shown in FIG. 15. The expression levels for certain miRNA sequences, as well as those overexpressed in ILD lung tissue, are listed below in Table 6.

TABLE 6

| microRNA sequence | mean level (ILD) | mean level (control) | mean ILD/ mean control |
|---|---|---|---|
| hsa-miR-923 | 6114.7 | 22421.33 | 0.3 |
| hsa-miR-22 | 5555.8 | 4771.83 | 1.2 |
| hsa-miR-29a | 4881.6 | 2183.67 | 2.2 |
| hsa-miR-145 | 3759.9 | 1449.50 | 2.6 |
| hsa-miR-26a | 3187.3 | 1123.33 | 2.8 |
| hsa-let-7c | 4405.5 | 1336.33 | 3.3 |
| hsa-miR-23a | 4396.1 | 1144.83 | 3.8 |
| hsa-miR-21 | 9938.7 | 2450.83 | 4.1 |
| hsa-miR-125b | 3843.2 | 939.17 | 4.1 |
| hsa-miR-27a | 3090.2 | 720.50 | 4.3 |
| hsa-let-7a | 5709.2 | 1039.33 | 5.5 |
| hsa-let-7f | 3352.5 | 504.83 | 6.6 |
| hsa-miR-451 | 6564.4 | 383.33 | 17.1 | miRNA hsa-miR-923 was over 130-fold over-expressed in ILD plasma relative to control plasma (Table 3), but it is under-expressed in ILD lung tissue relative to control lung tissue (Table 6). This suggests the tissue or cell of origin for this miRNA may be within the blood itself, or at least not the ILD lung. Similarly, miRNA hsa-miR-22 is expressed three times higher in ILD plasma compared to control plasma (Table 3), but is expressed at nearly the same level in ILD lung and control lung tissue (Table 6). Other miRNAs that are characteristic of ILD, such as miRNA-451, were elevated in ILD lung tissue (17× in Table 6) but not in ILD plasma (see Table 4).

In total 17 miRNA sequences were identified as containing diagnostic information related to ILD. Those 17 sequences are listed in Table 3.

Example 10

The plasma sample data (control, COPD, and ILD) was separately analyzed using the Panorama suite of tools and consisted of the following steps: (A) Normalization; (B) Quality Control; (C) Cluster Analysis; (D) Panel Selection; and (E) Comparison. Each step is explained in more detail below.

In Normalization, the following steps occurred. First, missing values were left unchanged instead of imputing a value. Second, each sample was normalized independently of other samples. Third, the natural log was applied to the values for each sample; then the values were adjusted by the median and standard deviation. FIG. 16 shows the results of normalization.

In Quality Control, the quality of the data was assessed before and after normalization. FIG. 17A shows the Pearson correlation distribution before normalization. This figure correlated the score for each miRNA across the samples to the total miRNA expression level across the samples. This figure showed that the vast majority of miRNA sequences had the same expression profile across the samples, and furthermore, this expression profile is the total miRNA level per sample—this is the dominant feature of the dataset. FIG. 17B shows the Pearson correlation distribution after normalization. Normalization improved the quality of the dataset. The distribution in FIG. 17B was much less skewed than that of FIG. 17A.

In Cluster Analysis, the normalized miRNA data was clustered using multi-dimensional scaling (MDS); the results are presented in FIG. 18. This was an unsupervised analysis without samples being identified by group or miRNA selected that differentiated the groups. There were several notable features of this plot. First, the samples within each group clustered together showing uniformity in miRNA expression. The exception was IPF tissue where a few outliers occurred, likely due to sample handling. Second, the tissue groups cluster away from the plasma groups. Third, within the plasma groups, the COPD and ILD plasma samples overlapped and were clustered away from the plasma control samples.

Performing a T-test at significance level 0.01, 194 miRNA were found to separate the plasma control samples from the ILD plasma samples. Performing 50 permutation tests revealed that the expected number of miRNA, by chance alone, was 21.5, yielding a false discovery rate of 11%. The p-value distribution of all miRNA is shown in FIG. 19. There was a uniform distribution over most p-values, except an increase below 0.05. This was consistent with the hypothesis that there are miRNA that segregate the two sample groups.

In Panel Selection, panels that segregated the control plasma samples from the ILD plasma samples were selected using Area Under the Curve (AUC). AUC is a measure of diagnostic segregation. It ranges from 0 to 1 where 1 indicates perfect segregation. The AUC of individual miRNA can be determined independently of each other allowing for straightforward selection of the best segregating miRNA. In addition, the combined AUC of panels of miRNA can be calculated to assess how well groups of miRNA work together to segregate control plasma samples from ILD plasma samples.

To calculate the combined AUC, a combination rule must be established. The combination rule used here was majority consensus: if the strict majority of miRNA classified a sample as diseased (i.e. ILD or IPF) then the sample was classified diseased, otherwise, the sample was classified as normal.

FIG. 20 is three charts showing the distribution of directional bias (upper left), the AUC distribution (upper right), and the standard deviation for the ILD group (lower left). The number of miRNA higher in the control samples than the ILD samples was essentially the same as the opposite direction. The distribution of AUC scores for all miRNA was centered about 0.6 which is expected. A small rise around 0.95 indicated the presence of miRNA that distinguish the control and ILD samples. The distribution of miRNA expression standard deviations showed that overall, variability was similar across miRNA (note that normalization is done by sample, not by miRNA).

In Comparison, the data was analyzed. Using an AUC threshold of 0.95, 57 out of 2421 (2.4%) miRNA probes were selected. Table 7 contains the oligo probe used for the miRNA, the corresponding miRNA, p-value, AUC, and number of panels of 3 miRNA above combined AUC 0.99 that each miRNA participated in. If the miRNA was expressed higher in the control sample than the ILD sample, the column "Control>ILD" was marked with a Y.

11 of the 17 miRNA sequences listed in Table 3 of Example 7 also appear in Table 7. They are shown in bold text in Table 7.

The claims refer to identifying "at least one" or "at least two" differentially expressed microRNA sequences in a

TABLE 7

| Probe | miRNA | Control > ILD | P-value | AUC | St. Dev. | # Panels |
|---|---|---|---|---|---|---|
| A_25_P00010804 | hsa-miR-518d-3p | Y | 9.96E−06 | 1.00 | 0.42 | 945 |
| A_25_P00013406 | hsa-miR-135a* | N | 1.56E−09 | 1.00 | 0.55 | 681 |
| A_25_P00013825 | hiv1-miR-H1 | N | 4.98E−06 | 1.00 | 0.66 | 656 |
| A_25_P00011724 | hcmv-miR-UL70-3p | N | 1.23E−13 | 1.00 | 0.62 | 621 |
| A_25_P00013407 | hsa-miR-135a* | N | 1.41E−12 | 1.00 | 0.62 | 615 |
| A_25_P00013090 | hsa-miR-940 | N | 8.13E−09 | 1.00 | 0.88 | 581 |
| A_25_P00012074 | hsa-miR-139-3p | N | 3.27E−07 | 1.00 | 0.63 | 572 |
| A_25_P00013689 | kshv-miR-K12-3 | N | 1.09E−11 | 1.00 | 0.60 | 572 |
| A_25_P00012231 | hsa-miR-134 | N | 9.11E−11 | 1.00 | 0.64 | 548 |
| A_25_P00012230 | hsa-miR-134 | N | 6.22E−13 | 1.00 | 0.65 | 539 |
| A_25_P00010345 | hsa-miR-557 | N | 2.47E−06 | 1.00 | 0.55 | 534 |
| A_25_P00013829 | hsv1-miR-LAT | N | 1.52E−11 | 1.00 | 0.77 | 500 |
| A_25_P00011725 | hcmv-miR-UL70-3p | N | 6.62E−13 | 1.00 | 0.65 | 463 |
| A_25_P00013830 | hsv1-miR-LAT | N | 1.42E−12 | 1.00 | 0.65 | 449 |
| A_25_P00013831 | hsv1-miR-LAT | N | 2.62E−09 | 1.00 | 0.84 | 449 |
| A_25_P00013087 | hsa-miR-939 | N | 3.19E−13 | 1.00 | 0.53 | 362 |
| A_25_P00013453 | hsa-miR-150* | N | 1.67E−08 | 1.00 | 0.58 | 362 |
| A_25_P00014907 | hsa-miR-1224-5p | N | 6.43E−07 | 1.00 | 0.47 | 344 |
| A_25_P00013326 | hsa-miR-187* | N | 1.24E−06 | 1.00 | 0.70 | 324 |
| A_25_P00013828 | hsv1-miR-LAT | N | 1.33E−12 | 1.00 | 0.80 | 299 |
| A_25_P00011853 | ebv-miR-BART13 | N | 4.09E−08 | 0.99 | 0.47 | 435 |
| A_25_P00015004 | hsa-miR-1226* | N | 2.14E−06 | 0.99 | 0.66 | 362 |
| A_25_P00010687 | hsa-miR-498 | N | 7.82E−08 | 0.99 | 0.46 | 498 |
| A_25_P00011096 | hsa-miR-572 | N | 3.25E−08 | 0.99 | 0.81 | 420 |
| A_25_P00010808 | hsa-miR-575 | N | 2.42E−07 | 0.99 | 0.85 | 415 |
| A_25_P00014908 | hsa-miR-1224-5p | N | 4.81E−07 | 0.99 | 0.60 | 344 |
| A_25_P00014896 | hsa-miR-575 | N | 4.23E−07 | 0.99 | 0.82 | 316 |
| A_25_P00010641 | hsa-miR-601 | N | 2.63E−08 | 0.99 | 0.49 | 218 |
| A_25_P00013086 | hsa-miR-939 | N | 1.09E−07 | 0.99 | 0.49 | 179 |
| A_25_P00013450 | hsa-miR-150* | N | 2.91E−08 | 0.99 | 0.67 | 178 |
| A_25_P00010344 | hsa-miR-557 | N | 5.45E−06 | 0.98 | 0.65 | 684 |
| A_25_P00013327 | hsa-miR-187* | N | 1.06E−05 | 0.98 | 0.65 | 347 |
| A_25_P00015003 | hsa-miR-1226* | N | 2.15E−06 | 0.98 | 0.61 | 179 |
| A_25_P00013451 | hsa-miR-150* | N | 1.39E−06 | 0.98 | 0.67 | 178 |
| A_25_P00014906 | hsa-miR-1224-5p | N | 2.03E−07 | 0.97 | 0.55 | 330 |
| A_25_P00012059 | hsa-miR-198 | N | 1.13E−05 | 0.97 | 0.67 | 296 |
| A_25_P00011799 | hsv1-miR-H1 | N | 6.61E−07 | 0.97 | 0.98 | 268 |
| A_25_P00011097 | hsa-miR-572 | N | 6E−05 | 0.97 | 0.60 | 203 |
| A_25_P00013452 | hsa-miR-150* | N | 8.41E−07 | 0.97 | 0.62 | 179 |
| A_25_P00010669 | hsa-miR-326 | N | 7.84E−05 | 0.97 | 0.83 | 177 |
| A_25_P00014892 | hsa-miR-539 | N | 0.000543 | 0.97 | 0.59 | 722 |
| A_25_P00010444 | hsa-miR-448 | N | 6.72E−05 | 0.97 | 0.58 | 581 |
| A_25_P00012030 | hsa-miR-92a | N | 1.18E−05 | 0.97 | 0.86 | 343 |
| A_25_P00013448 | hsa-miR-149* | N | 1.95E−05 | 0.97 | 0.58 | 260 |
| A_25_P00014861 | hsa-miR-483-5p | N | 2.9E−07 | 0.97 | 0.62 | 144 |
| A_25_P00010228 | hsa-miR-623 | N | 5.7E−05 | 0.96 | 0.79 | 356 |
| A_25_P00012419 | hsa-miR-423-5p | N | 0.000569 | 0.96 | 0.87 | 336 |
| A_25_P00011796 | hsv1-miR-H1 | N | 2.96E−06 | 0.96 | 0.69 | 268 |
| A_25_P00011854 | ebv-miR-BART13 | N | 0.000141 | 0.96 | 0.73 | 268 |
| A_25_P00011719 | ebv-miR-BART7 | N | 7.87E−05 | 0.96 | 0.57 | 224 |
| A_25_P00012459 | hsa-miR-483-5p | N | 2.03E−07 | 0.96 | 0.66 | 178 |
| A_25_P00013449 | hsa-miR-149* | N | 1.55E−06 | 0.96 | 0.66 | 164 |
| A_25_P00012262 | hsa-miR-320 | N | 5.41E−05 | 0.96 | 0.73 | 84 |
| A_25_P00011342 | hsa-miR-765 | N | 5.08E−06 | 0.96 | 0.38 | 57 |
| A_25_P00013324 | hsa-miR-187* | N | 5.29E−05 | 0.95 | 0.68 | 477 |
| A_25_P00010227 | hsa-miR-623 | N | 4.89E−05 | 0.95 | 0.97 | 362 |
| A_25_P00012031 | hsa-miR-92a | N | 2.59E−05 | 0.95 | 1.07 | 343 |

Interestingly, only 3 of the 57 miRNA were higher in the control samples than the ILD samples, despite the near equivalence of miRNA higher in control samples over ILD samples, as compared to the opposite among all miRNA (see FIG. 20). 20 of the 57 miRNA had a perfect AUG score of 1.00. Not shown here is the fact that there were also many panels of three miRNA that had a perfect AUG score of 1.00.

There were also unique miRNA among the 57 miRNA probes, which illustrated a strong redundancy among probes. This redundancy could be used as a selection criterion.

microRNA profile, wherein the differentially expressed microRNA sequences are selected from a list. This language should be construed as meaning that the microRNA sequence selected from the list is identified as a differentially expressed microRNA sequence in the microRNA profile.

It is contemplated that assays or microRNA profiles would test for only specific microRNA sequences, such as those identified above.

In some embodiments, an assay or microRNA profile tests for at least two microRNA sequences selected from the group consisting of miR-630, miR-134, hcmv-miR-UL70-3p, miR- 1225-5p, miR-135a*, miR-150*, miR-22, miR-223, miR-483-5p, miR-575, miR-638, miR-923, miR-939, miR-940, hsv1-miR-H1, hsv1-miR-LAT, kshv-miR-K12-3, and human orthologs thereof. In other embodiments, at least three of these sequences is tested for. In particular embodiments, all 17 of these sequences are tested for. Specific pairs of these 17 microRNA sequences include those listed in Table 8:

TABLE 8

| | |
|---|---|
| miR-630, miR-134 | miR-630, hcmv-miR-UL70-3p |
| miR-630, miR-1225-5p | miR-630, miR-135a* |
| miR-630, miR-150* | miR-630, miR-22 |
| miR-630, miR-223 | miR-630, miR-483-5p |
| miR-630, miR-575 | miR-630, miR-638 |
| miR-630, miR-923 | miR-630, miR-939 |
| miR-630, miR-940 | miR-630, hsv1-miR-H1 |
| miR-630, hsv1-miR-LAT | miR-630, kshv-miR-K12-3 |
| miR-134, hcmv-miR-UL70-3p | miR-134, miR-1225-5p |
| miR-134, miR-135a* | miR-134, miR-150* |
| miR-134, miR-22 | miR-134, miR-223 |
| miR-134, miR-483-5p | miR-134, miR-575 |
| miR-134, miR-638 | miR-134, miR-923 |
| miR-134, miR-939 | miR-134, miR-940 |
| miR-134, hsv1-miR-H1 | miR-134, hsv1-miR-LAT |
| miR-134, kshv-miR-K12-3 | hcmv-miR-UL70-3p, miR-1225-5p |
| hcmv-miR-UL70-3p, miR-135a* | hcmv-miR-UL70-3p, miR-150* |
| hcmv-miR-UL70-3p, miR-22 | hcmv-miR-UL70-3p, miR-223 |
| hcmv-miR-UL70-3p, miR-483-5p | hcmv-miR-UL70-3p, miR-575 |
| hcmv-miR-UL70-3p, miR-638 | hcmv-miR-UL70-3p, miR-923 |
| hcmv-miR-UL70-3p, miR-939 | hcmv-miR-UL70-3p, miR-940 |
| hcmv-miR-UL70-3p, hsv1-miR-H1 | hcmv-miR-UL70-3p, hsv1-miR-LAT |
| hcmv-miR-UL70-3p, kshv-miR-K12-3 | miR-1225-5p, miR-135a* |
| miR-1225-5p, miR-150* | miR-1225-5p, miR-22 |
| miR-1225-5p, miR-223 | miR-1225-5p, miR-483-5p |
| miR-1225-5p, miR-575 | miR-1225-5p, miR-638 |
| miR-1225-5p, miR-923 | miR-1225-5p, miR-939 |
| miR-1225-5p, miR-940 | miR-1225-5p, hsv1-miR-H1 |
| miR-1225-5p, hsv1-miR-LAT | miR-1225-5p, kshv-miR-K12-3 |
| miR-135a*, miR-150* | miR-135a*, miR-22 |
| miR-135a*, miR-223 | miR-135a*, miR-483-5p |
| miR-135a*, miR-575 | miR-135a*, miR-638 |
| miR-135a*, miR-923 | miR-135a*, miR-939 |
| miR-135a*, miR-940 | miR-135a*, hsv1-miR-H1 |
| miR-135a*, hsv1-miR-LAT | miR-135a*, kshv-miR-K12-3 |
| miR-150*, miR-22 | miR-150*, miR-223 |
| miR-150*, miR-483-5p | miR-150*, miR-575 |
| miR-150*, miR-638 | miR-150*, miR-923 |
| miR-150*, miR-939 | miR-150*, miR-940 |
| miR-150*, hsv1-miR-H1 | miR-150*, hsv1-miR-LAT |
| miR-150*, kshv-miR-K12-3 | miR-22, miR-223 |
| miR-22, miR-483-5p | miR-22, miR-575 |
| miR-22, miR-638 | miR-22, miR-923 |
| miR-22, miR-939 | miR-22, miR-940 |
| miR-22, hsv1-miR-H1 | miR-22, hsv1-miR-LAT |
| miR-22, kshv-miR-K12-3 | miR-223, miR-483-5p |
| miR-223, miR-575 | miR-223, miR-638 |
| miR-223, miR-923 | miR-223, miR-939 |
| miR-223, miR-940 | miR-223, hsv1-miR-H1 |
| miR-223, hsv1-miR-LAT | miR-223, kshv-miR-K12-3 |
| miR-483-5p, miR-575 | miR-483-5p, miR-638 |
| miR-483-5p, miR-923 | miR-483-5p, miR-939 |
| miR-483-5p, miR-940 | miR-483-5p, hsv1-miR-H1 |
| miR-483-5p, hsv1-miR-LAT | miR-483-5p, kshv-miR-K12-3 |
| miR-575, miR-638 | miR-575, miR-923 |
| miR-575, miR-939 | miR-575, miR-940 |
| miR-575, hsv1-miR-H1 | miR-575, hsv1-miR-LAT |
| miR-575, kshv-miR-K12-3 | miR-638, miR-923 |
| miR-638, miR-939 | miR-638, miR-940 |
| miR-638, hsv1-miR-H1 | miR-638, hsv1-miR-LAT |
| miR-638, kshv-miR-K12-3 | miR-923, miR-939 |
| miR-923, miR-940 | miR-923, hsv1-miR-H1 |
| miR-923, hsv1-miR-LAT | miR-923, kshv-miR-K12-3 |
| miR-939, miR-940 | miR-939, hsv1-miR-H1 |
| miR-939, hsv1-miR-LAT | miR-939, kshv-miR-K12-3 |
| miR-940, hsv1-miR-H1 | miR-940, hsv1-miR-LAT |
| miR-940, kshv-miR-K12-3 | hsv1-miR-H1, hsv1-miR-LAT |
| hsv1-miR-H1, kshv-miR-K12-3 | hsv1-miR-LAT, kshv-miR-K12-3 |

In other embodiments, an assay or microRNA profile tests for at least two microRNA sequences selected from the group consisting of miR-630, miR-134, hcmv-miR-UL70-3p, miR-1225-5p, miR-135a*, miR-150*, miR-483-5p, miR-575, miR-638, hsv1-miR-H1, hsv1-miR-LAT, and human orthologs thereof. In other embodiments, at least three of these sequences is tested for. In particular embodiments, all 11 of these sequences are tested for. Specific pairs of these 11 microRNA sequences include those listed in Table 9:

TABLE 9

| | |
|---|---|
| miR-630, miR-134 | miR-630, hcmv-miR-UL70-3p |
| miR-630, miR-1225-5p | miR-630, miR-135a* |
| miR-630, miR-150* | miR-630, miR-483-5p |
| miR-630, miR-575 | miR-630, miR-638 |
| miR-630, hsv1-miR-H1 | miR-630, hsv1-miR-LAT |
| miR-134, hcmv-miR-UL70-3p | miR-134, miR-1225-5p |
| miR-134, miR-135a* | miR-134, miR-150* |
| miR-134, miR-483-5p | miR-134, miR-575 |
| miR-134, miR-638 | miR-134, hsv1-miR-H1 |
| miR-134, hsv1-miR-LAT | hcmv-miR-UL70-3p, miR-1225-5p |
| hcmv-miR-UL70-3p, miR-135a* | hcmv-miR-UL70-3p, miR-150* |
| hcmv-miR-UL70-3p, miR-483-5p | hcmv-miR-UL70-3p, miR-575 |
| hcmv-miR-UL70-3p, miR-638 | hcmv-miR-UL70-3p, hsv1-miR-H1 |
| hcmv-miR-UL70-3p, hsv1-miR-LAT | miR-1225-5p, miR-135a* |
| miR-1225-5p, miR-150* | miR-1225-5p, miR-483-5p |
| miR-1225-5p, miR-575 | miR-1225-5p, miR-638 |
| miR-1225-5p, hsv1-miR-H1 | miR-1225-5p, hsv1-miR-LAT |
| miR-135a*, miR-150* | miR-135a*, miR-483-5p |
| miR-135a*, miR-575 | miR-135a*, miR-638 |
| miR-135a*, hsv1-miR-H1 | miR-135a*, hsv1-miR-LAT |
| miR-150*, miR-483-5p | miR-150* miR-575 |
| miR-150*, miR-638 | miR-150*, hsv1-miR-H1 |
| miR-150*, hsv1-miR-LAT | miR-483-5p, miR-575 |
| miR-483-5p, miR-638 | miR-483-5p, hsv1-miR-H1 |
| miR-483-5p, hsv1-miR-LAT | miR-575, miR-638 |
| miR-575, hsv1-miR-H1 | miR-575, hsv1-miR-LAT |
| miR-638, hsv1-miR-H1 | miR-638, hsv1-miR-LAT |
| hsv1-miR-H1, hsv1-miR-LAT | |

In some embodiments, an assay or microRNA profile tests for two or more microRNA sequences. At least one of the microRNA sequences tested for is selected from the group consisting of miR-630, hcmv-miR-UL70-3p, miR-1225-5p, miR-134, miR-135a*, miR-150*, miR-483-5p, miR-575, miR-638, hsv1-miR-H1, hsv1-miR-LAT, and human orthologs thereof. At least one of the microRNA sequences tested for is selected from the group consisting of miR-451, miR-448, and miR-92a-2*. In particular embodiments, miR-451 is one of the microRNA sequences tested for. Specific pairs of these microRNA sequences include those listed in Table 10:

TABLE 10

| | |
|---|---|
| miR-630, miR-451 | miR-630, miR-448 |
| miR-630, miR-92a-2* | hcmv-miR-UL70-3p, miR-451 |
| hcmv-miR-UL70-3p, miR-448 | hcmv-miR-UL70-3p, miR-92a-2* |
| miR-1225-5p, miR-451 | miR-1225-5p, miR-448 |
| miR-1225-5p, miR-92a-2* | miR-134, miR-451 |
| miR-134, miR-448 | miR-134, miR-92a-2* |
| miR-135a*, miR-451 | miR-135a*, miR-448 |
| miR-135a*, miR-92a-2* | miR-150*, miR-451 |
| miR-150*, miR-448 | miR-150*, miR-92a-2* |
| miR-483-5p, miR-451 | miR-483-5p, miR-448 |
| miR-483-5p, miR-92a-2* | miR-575, miR-451 |
| miR-575, miR-448 | miR-575, miR-92a-2* |
| miR-638, miR-451 | miR-638, miR-448 |
| miR-638, miR-92a-2* | hsv1-miR-H1, miR-451 |
| hsv1-miR-H1, miR-448 | hsv1-miR-H1, miR-92a-2* |
| hsv1-miR-LAT, miR-451 | hsv1-miR-LAT, miR-448 |
| hsv1-miR-LAT, miR-92a-2* | |

In some embodiments, an assay or microRNA profile tests for at least two microRNA sequences selected from the group consisting of miR-451, miR-923, miR-1225-5p, miR-22, miR-223, miR-638, kshv-miR-K12-3, and human orthologs thereof. In other embodiments, at least three of these sequences is tested for. In particular embodiments, all seven of these sequences are tested for. Specific pairs of these seven microRNA sequences include those listed in Table 11:

TABLE 11

| | |
|---|---|
| miR-451, miR-923 | miR-451, miR-1225-5p |
| miR-451, miR-22 | miR-451, miR-223 |
| miR-451, miR-638 | miR-451, kshv-miR-K12-3 |
| miR-923, miR-1225-5p | miR-923, miR-22 |
| miR-923, miR-223 | miR-923, miR-638 |
| miR-923, kshv-miR-K12-3 | miR-1225-5p, miR-22 |
| miR-1225-5p, miR-223 | miR-1225-5p, miR-638 |
| miR-1225-5p, kshv-miR-K12-3 | miR-22, miR-223 |
| miR-22, miR-638 | miR-22, kshv-miR-K12-3 |
| miR-223, miR-638 | miR-223, kshv-miR-K12-3 |
| miR-638, kshv-miR-K12-3 | |

In some embodiments, an assay or microRNA profile tests for at least two microRNA sequences selected from the group consisting of miR-940, miR-134, miR-135a*, miR-150*, miR-483-5p, miR-575, miR-939, hsv1-miR-H1, kshv-miR-K12-3, hsv1-miR-LAT, hcmv-miR-UL70-3p, and human orthologs thereof. In other embodiments, at least three of these sequences is tested for. In particular embodiments, all 11 of these sequences are tested for. Specific pairs of these 11 microRNA sequences include those listed in Table 12:

TABLE 12

| | |
|---|---|
| miR-940, miR-134 | miR-940, miR-135a* |
| miR-940, miR-150* | miR-940, miR-483-5p |
| miR-940, miR-575 | miR-940, miR-939 |
| miR-940, hsv1-miR-H1 | miR-940, kshv-miR-K12-3 |
| miR-940, hsv1-miR-LAT | miR-940, hcmv-miR-UL70-3p |
| miR-134, miR-135a* | miR-134, miR-150* |
| miR-134, miR-483-5p | miR-134, miR-575 |
| miR-134, miR-939 | miR-134, hsv1-miR-H1 |
| miR-134, kshv-miR-K12-3 | miR-134, hsv1-miR-LAT |
| miR-134, hcmv-miR-UL70-3p | miR-135a*, miR-150* |
| miR-135a*, miR-483-5p | miR-135a*, miR-575 |
| miR-135a*, miR-939 | miR-135a*, hsv1-miR-H1 |
| miR-135a*, kshv-miR-K12-3 | miR-135a*, hsv1-miR-LAT |
| miR-135a*, hcmv-miR-UL70-3p | miR-150*, miR-483-5 |
| miR-150*, miR-575 | miR-150*, miR-939 |
| miR-150*, hsv1-miR-H1 | miR-150*, kshv-miR-K12-3 |
| miR-150*, hsv1-miR-LAT | miR-150*, hcmv-miR-UL70-3p |
| miR-483-5p, miR-575 | miR-483-5p, miR-939 |
| miR-483-5p, hsv1-miR-H1 | miR-483-5p, kshv-miR-K12-3 |
| miR-483-5p, hsv1-miR-LAT | miR-483-5p, hcmv-miR-UL70-3p |
| miR-575, miR-939 | miR-575, hsv1-miR-H1 |
| miR-575, kshv-miR-K12-3 | miR-575, hsv1-miR-LAT |
| miR-575, hcmv-miR-UL70-3p | miR-939, hsv1-miR-H1 |
| miR-939, kshv-miR-K12-3 | miR-939, hsv1-miR-LAT |
| miR-939, hcmv-miR-UL70-3p | hsv1-miR-H1, kshv-miR-K12-3 |
| hsv1-miR-H1, hsv1-miR-LAT | hsv1-miR-H1, hcmv-miR-UL70-3p |
| kshv-miR-K12-3, hsv1-miR-LAT | kshv-miR-K12-3, hcmv-miR-UL70-3p |
| hsv1-miR-LAT, hcmv-miR-UL70-3p | |

Appendix A provides a listing of the RNA sequences for all of the microRNA discussed herein, including human orthologs thereof.

Appendix A

| miRNA name | Accession Number | RNA Sequence | SEQ ID No: |
|---|---|---|---|
| ebv-miR-BART10* | MIMAT0004817 | gccaccucuuuggvucuguaca | 1 |
| ebv-miR-BART12 | MIMAT0003423 | uccuguggvguuuggugugguu | 2 |
| ebv-miR-BART13 | MIMAT0003424 | uguaacuugccagggacggcuga | 3 |
| ebv-miR-BART13* | MIMAT0004818 | aaccggcucguggcucguacag | 4 |
| ebv-miR-BART15 | MIMAT0003713 | gucaguggvuuuguuuccuuga | 5 |
| ebv-miR-BART15p | MIMAT0000999 | ucuuagggaagugacgugcugug | 6 |
| ebv-miR-BART16 | MIMAT0003714 | uuagauagaguggguguguggcucu | 7 |
| ebv-miR-BART18-5p | MIMAT0003717 | ucaaguucgcacuuccuauaca | 8 |
| ebv-miR-BART19-3p | MIMAT0003718 | uuuuguuugcuugggaaugcu | 9 |
| ebv-miR-BART19-5p | MIMAT0004836 | acauccccgcaaacaugacaug | 10 |
| ebv-miR-BART20-5p | MIMAT0003719 | uagcaggcaugucuucauucc | 11 |
| ebv-miR-BART2-5p | MIMAT0001000 | uauuuucugcauucgcccuugc | 12 |
| ebv-miR-BART3* | MIMAT0003410 | accvaguguuaguguugugcu | 13 |
| ebv-miR-BART5 | MIMAT0003413 | caaggugaauauagcugcccaucg | 14 |
| ebv-miR-BART6-5p | MIMAT0003414 | uaaggvuggvccaauccauagg | 15 |
| ebv-miR-BART7 | MIMAT0003416 | caucauaguccaguguccaggg | 16 |
| ebv-miR-BART7* | MIMAT0004815 | ccuggaccuugacuaugaaaca | 17 |

-continued

Appendix A

| miRNA name | Accession Number | RNA Sequence | SEQ ID No: |
|---|---|---|---|
| ebv-miR-BHRF1-1 | MIMAT0000995 | uaaccugaucagccccggaguu | 18 |
| ebv-miR-BHRF1-3 | MIMAT0000998 | uaacgggaaguguguaagcaca | 19 |
| hcmv-miR-UL148D | MIMAT0001578 | ucguccuccccuucuucaccg | 20 |
| hcmv-miR-UL22A | MIMAT0001574 | uaacuagccuucccgugaga | 21 |
| hcmv-miR-UL22A* | MIMAT0001575 | ucaccagaaugcuaguuuguag | 22 |
| hcmv-miR-UL70-3p | MIMAT0003343 | ggggaugggcuggcgcgcgg | 23 |
| hcmv-miR-UL70-5p | MIMAT0003342 | ugcgucucggccucguccaga | 24 |
| hcmv-miR-US25-1 | MIMAT0001581 | aaccgcucaguggcucggacc | 25 |
| hcmv-miR-US25-2-3p | MIMAT0001583 | auccacuuggagagcucccgcgg | 26 |
| hcmv-miR-US25-2-5p | MIMAT0001582 | agcggucuguucagguggauga | 27 |
| hcmv-miR-US4 | MIMAT0003341 | cgacauggacgugcaggggau | 28 |
| hiv1-miR-H1 | MIMAT0004480 | ccagggaggcgugccugggc | 29 |
| hiv1-miR-N367 | MIMAT0004478 | acugaccuuuggauggugcuucaa | 30 |
| hsa-miR-1 | MIMAT0000416 | ggaauguaaagaaguauguau | 31 |
| hsa-miR-10b | MIMAT0000254 | uacccuguagaaccgaauuugug | 32 |
| hsa-miR-122 | MIMAT0000421 | uggagugugacaauggugutug | 33 |
| hsa-miR-1224-3p | MIMAT0005459 | ccccaccuccucucuccucag | 34 |
| hsa-miR-1224-5p | MIMAT0005458 | gugaggacucgggaggugg | 35 |
| hsa-miR-1225-3p | MIMAT0005573 | ugagccccugugccgcccag | 36 |
| hsa-miR-1225-5p | MIMAT0005572 | gugggacggcccagugggggg | 37 |
| hsa-miR-1226* | MIMAT0005576 | gugagggcaugcaggccuggauggg | 38 |
| hsa-miR-1227 | MIMAT0005580 | cgugccacccuuuucccag | 39 |
| hsa-miR-1228 | MIMAT0005583 | ucacaccugccucgcccccc | 40 |
| hsa-miR-1229 | MIMAT0005584 | cucucaccacugcccuccacag | 41 |
| hsa-miR-1234 | MIMAT0005589 | ucggccugaccacccaccccac | 42 |
| hsa-miR-1237 | MIMAT0005592 | uccuucugcuccgucccccag | 43 |
| hsa-miR-1238 | MIMAT0005593 | cuuccucgucugucugcccc | 44 |
| hsa-miR-124 | MIMAT0000422 | uaaggcacgcggugaaugcc | 45 |
| hsa-miR-125a-3p | MIMAT0004602 | acaggugagguucuugggagcc | 46 |
| hsa-miR-125a-5p | MIMAT0000443 | ucccugagacccuuuaaccuguga | 47 |
| hsa-miR-127-3p | MIMAT0000446 | ucggauccgucugagcuuggcu | 48 |
| hsa-miR-127-5p | MIMAT0004604 | cugaagcucagagggcucugau | 49 |
| hsa-miR-128 | MIMAT0000424 | ucacagugaaccggucucuuu | 50 |
| hsa-miR-129* | MIMAT0004548 | aagccuuacccaaaaguau | 51 |
| hsa-miR-129-3p | MIMAT0004605 | aagcccuuaccccaaaagcau | 52 |
| hsa-miR-130a | MIMAT0000425 | cagugcaauguuaaagggcau | 53 |
| hsa-miR-133a | MIMAT0000427 | uuuggucccccuucaaccagcug | 54 |

-continued

Appendix A

| miRNA name | Accession Number | RNA Sequence | SEQ ID No: |
|---|---|---|---|
| hsa-miR-133b | MIMAT0000770 | uuugguccccuucaaccagcua | 55 |
| hsa-miR-134 | MIMAT0000447 | ugugacugguugaccagagggg | 56 |
| hsa-miR-135a* | MIMAT0004595 | uauagggauuggagccguggcg | 57 |
| hsa-miR-136 | MIMAT0000448 | acuccauuuguuuugaugaugga | 58 |
| hsa-miR-136* | MIMAT0004606 | caucaucgucucaaaugagucu | 59 |
| hsa-miR-138 | MIMAT0000430 | agcuggugugugaaucaggccg | 60 |
| hsa-miR-139-3p | MIMAT0004552 | ggagacgcggcccuguuggagu | 61 |
| hsa-miR-140-3p | MIMAT0004597 | uaccacaggguagaaccacgg | 62 |
| hsa-miR-140-5p | MIMAT0000431 | cagugguuuuacccuaugguag | 63 |
| hsa-miR-141 | MIMAT0000432 | uaacacugucugguaaagaugg | 64 |
| hsa-miR-142-3p | MIMAT0000434 | uguaguguuuccuacuuuaugga | 65 |
| hsa-miR-143 | MIMAT0000435 | ugagaugaagcacuguagcuc | 66 |
| hsa-miR-146a | MIMAT0000449 | ugagaacugaauuccaugdgguu | 67 |
| hsa-miR-146b-3p | MIMAT0004766 | ugcccuguggacucaguucgg | 68 |
| hsa-miR-146b-5p | MIMAT0002809 | ugagaacugaauuccauaggcu | 69 |
| hsa-miR-148b | MIMAT0000759 | ucagugcaucacagaacuuugu | 70 |
| hsa-miR-150 | MIMAT0000451 | ucucccaacccuuguaccagug | 71 |
| hsa-miR-150* | MIMAT0004610 | cugguacaggccuggggggacag | 72 |
| hsa-miR-15a* | MIMAT0004488 | caggccauauugugcugccuca | 73 |
| hsa-miR-15b | MIMAT0000417 | uagcagcacaucauggguuuaca | 74 |
| hsa-miR-181b | MIMAT0000257 | aacauucauugcugucgguggu | 75 |
| hsa-miR-181d | MIMAT0002821 | aacauucauuguugucgguggu | 76 |
| hsa-miR-183 | MIMAT0000261 | uauggcacugguagaauucacu | 77 |
| hsa-miR-185 | MIMAT0000455 | uggagagaaaggcaguuccuga | 78 |
| hsa-miR-186 | MIMAT0000456 | caaagaauucuccuuuugggcu | 79 |
| hsa-miR-187* | MIMAT0004561 | ggcuacaacacaggacccgggc | 80 |
| hsa-miR-188-5p | MIMAT0000457 | caucccuugcaugguggaggg | 81 |
| hsa-miR-190b | MIMAT0004929 | ugauauguuugauauugdgguu | 82 |
| hsa-miR-191* | MIMAT0001618 | gcugcgcuuggauuucgucccc | 83 |
| hsa-miR-193b | MIMAT0002819 | aacuggcccucaaagucccgcu | 84 |
| hsa-miR-194 | MIMAT0000460 | uguaacagcaacuccaugugga | 85 |
| hsa-miR-198 | MIMAT0000228 | gguccagaggggagauagguuc | 86 |
| hsa-miR-199a-5p | MIMAT0000231 | cccaguguucagacuaccuguuc | 87 |
| hsa-miR-19a | MIMAT0000073 | ugugcaaaucuaugcaaaacuga | 88 |
| hsa-miR-200a | MIMAT0000682 | uaacacugucugguaacgaugu | 89 |
| hsa-miR-200b | MIMAT0000318 | uaauacugccugguaaugauga | 90 |
| hsa-miR-200b* | MIMAT0004571 | caucuuacugggcagcauugga | 91 |
| hsa-miR-200c | MIMAT0000617 | uaauacugccggguaaugaugga | 92 |

-continued

Appendix A

| miRNA name | Accession Number | RNA Sequence | SEQ ID No: |
|---|---|---|---|
| hsa-miR-205 | MIMAT0000266 | uccuucauuccaccggagucug | 93 |
| hsa-miR-206 | MIMAT0000462 | uggaauguaaggaagugugugg | 94 |
| hsa-miR-208a | MIMAT0000241 | auaagacgagcaaaaagcuugu | 95 |
| hsa-miR-21 | MIMAT0000076 | uagcuuaucagacugauguuga | 96 |
| hsa-miR-211 | MIMAT0000268 | uucccuuugucauccuucgccu | 97 |
| hsa-miR-22 | MIMAT0000077 | aagcugccaguugaagaacugu | 98 |
| hsa-miR-220b | MIMAT0004908 | ccaccaccgugucugacacuu | 99 |
| hsa-miR-221 | MIMAT0000278 | agcuacauugucugcugggunuc | 100 |
| hsa-miR-222 | MIMAT0000279 | agcuacaucuggcuacugggu | 101 |
| hsa-miR-223 | MIMAT0000280 | ugucaguuugucaaauaccca | 102 |
| hsa-miR-23b | MIMAT0000418 | aucacauugccagggauuacc | 103 |
| hsa-miR-26a | MIMAT0000082 | uucaaguaauccaggauaggcu | 104 |
| hsa-miR-27a | MIMAT0000084 | uucacaguggcuaaguuccgc | 105 |
| hsa-miR-27b | MIMAT0000419 | uucacaguggcuaaguucugc | 106 |
| hsa-miR-27b* | MIMAT0004588 | agagcuuagcugauuggugaac | 107 |
| hsa-miR-299-3p | MIMAT0000687 | uaugugggaugguaaaccgcuu | 108 |
| hsa-miR-299-5p | MIMAT0002890 | ugguuuaccgucccacauacau | 109 |
| hsa-miR-29b | MIMAT0000100 | uagcaccauuugaaaucaguguu | 110 |
| hsa-miR-29c* | MIMAT0004673 | ugaccgauuucuccugguguuc | 111 |
| hsa-miR-300 | MIMAT0004903 | uauacaagggcagacucucucu | 112 |
| hsa-miR-301b | MIMAT0004958 | cagugcaaugauauugucaaagc | 113 |
| hsa-miR-302c* | MIMAT0000716 | uuuaacauggggguaccugcug | 114 |
| hsa-miR-30a | MIMAT0000087 | uguaaacauccucgacuggaag | 115 |
| hsa-miR-30c | MIMAT0000244 | uguaaacauccuacacucucagc | 116 |
| hsa-miR-30c-1* | MIMAT0004674 | cugggagagggunuguuuacucc | 117 |
| hsa-miR-30e | MIMAT0000692 | uguaaacauccuugacuggaag | 118 |
| hsa-miR-31 | MIMAT0000089 | aggcaagaugcuggcauagcu | 119 |
| hsa-miR-323-3p | MIMAT0000755 | cacauuacacggucgaccucu | 120 |
| hsa-miR-324-3p | MIMAT0000762 | acugccccaggugcugcugg | 121 |
| hsa-miR-324-5p | MIMAT0000761 | cgcaucccuagggcauuggugu | 122 |
| hsa-miR-326 | MIMAT0000756 | ccucugggcccuuccuccag | 123 |
| hsa-miR-328 | MIMAT0000752 | cuggcccucucugcccuuccgu | 124 |
| hsa-miR-331-5p | MIMAT0004700 | cuagguaugguccccagggaucc | 125 |
| hsa-miR-338-3p | MIMAT0000763 | uccagcaucagugauuuuguug | 126 |
| hsa-miR-339-3p | MIMAT0004702 | ugagcgccucgacgacagagccg | 127 |
| hsa-miR-33a* | MIMAT0004506 | caauguuuccacagugcaucac | 128 |
| hsa-miR-33b | MIMAT0003301 | gugcauugcuguugcauugc | 129 |
| hsa-miR-33b* | MIMAT0004811 | cagugccucggcagugcagccc | 130 |

-continued

| Appendix A | | | |
|---|---|---|---|
| miRNA name | Accession Number | RNA Sequence | SEQ ID No: |
| hsa-miR-342-3p | MIMAT0000753 | ucucacacagaaaucgcacccgu | 131 |
| hsa-miR-34c-3p | MIMAT0004677 | aaucacuaaccacacggccagg | 132 |
| hsa-miR-34c-5p | MIMAT0000686 | aggcaguguaguuagcugauugc | 133 |
| hsa-miR-363* | MIMAT0003385 | cggguggaucacgaugcaauuu | 134 |
| hsa-miR-369-3p | MIMAT0000721 | aauaauacaugguugaucuuu | 135 |
| hsa-miR-370 | MIMAT0000722 | gccugcugggguggaaccuggu | 136 |
| hsa-miR-371-3p | MIMAT0000723 | aagugccgccaucuuuugagugu | 137 |
| hsa-miR-371-5p | MIMAT0004687 | acucaaacugugggggcacu | 138 |
| hsa-miR-375 | MIMAT0000728 | uuuguucguucggcucgcguga | 139 |
| hsa-miR-376b | MIMAT0002172 | aucauagaggaaaauccauguu | 140 |
| hsa-miR-377* | MIMAT0000730 | aucacacaaaggcaacuuuugu | 141 |
| hsa-miR-379 | MIMAT0000733 | ugguagacuauggaacguagg | 142 |
| hsa-miR-382 | MIMAT0000737 | gaaguuguucgugguggauucg | 143 |
| hsa-miR-409-5p | MIMAT0001638 | agguuacccgagcaacuuugcau | 144 |
| hsa-miR-411 | MIMAT0003329 | uaguagaccguauagcguacg | 145 |
| hsa-miR-411* | MIMAT0004813 | uauguaacacgguccacuaacc | 146 |
| hsa-miR-423-5p | MIMAT0004748 | ugaggggcagagagcgagacuuu | 147 |
| hsa-miR-424 | MIMAT0001341 | cagcagcaauucauguuuugaa | 148 |
| hsa-miR-424* | MIMAT0004749 | caaaacgugaggcgcugcuau | 149 |
| hsa-miR-425 | MIMAT0003393 | aaugacacgaucacucccguuga | 150 |
| hsa-miR-429 | MIMAT0001536 | uaauacugucugguaaaaccgu | 151 |
| hsa-miR-448 | MIMAT0001532 | uugcauauguaggaugucccau | 152 |
| hsa-miR-449a | MIMAT0001541 | uggcaguguauuguuagcuggu | 153 |
| hsa-miR-449b | MIMAT0003327 | aggcaguguauuguuagcuggc | 154 |
| hsa-miR-450b-3p | MIMAT0004910 | uugggaucauuuugcauccaua | 155 |
| hsa-miR-451 | MIMAT0001631 | aaaccguuaccauuacugaguu | 156 |
| hsa-miR-452 | MIMAT0001635 | aacguuugcagaggaaacuga | 157 |
| hsa-miR-454* | MIMAT0003884 | acccuaucaauauugucucugc | 158 |
| hsa-miR-455-3p | MIMAT0004784 | gcaguccaugggcauauacac | 159 |
| hsa-miR-455-5p | MIMAT0003150 | uaugugccuuuggacuacaucg | 160 |
| hsa-miR-483-3p | MIMAT0002173 | ucacuccucuccucccgucuu | 161 |
| hsa-miR-483-5p | MIMAT0004761 | aagacgggaggaaagaagggag | 162 |
| hsa-miR-484 | MIMAT0002174 | ucaggcucaguccccucccgau | 163 |
| hsa-miR-486-3p | MIMAT0004762 | cggggcagcucaguacaggau | 164 |
| hsa-miR-486-5p | MIMAT0002177 | uccuacugagcugcccgag | 165 |
| hsa-miR-487b | MIMAT0003180 | aaucguacaggguccaccacuu | 166 |
| hsa-miR-491-3p | MIMAT0004765 | cuuaugcaagauucccuucuac | 167 |
| hsa-miR-491-5p | MIMAT0002807 | aguggggaacccuuccaugagg | 168 |

-continued

Appendix A

| miRNA name | Accession Number | RNA Sequence | SEQ ID No: |
|---|---|---|---|
| hsa-miR-493 | MIMAT0003161 | ugaaggucuacugugugccagg | 169 |
| hsa-miR-493* | MIMAT0002813 | uuguacauguuaggcuuucauu | 170 |
| hsa-miR-494 | MIMAT0002816 | ugaaacauacacgggaaaccuc | 171 |
| hsa-miR-497 | MIMAT0002820 | cagcagcacacugugguuugu | 172 |
| hsa-miR-498 | MIMAT0002824 | uuucaagccaggggggcguuuuuc | 173 |
| hsa-miR-500 | MIMAT0004773 | uaauccuugcuaccugggugaga | 174 |
| hsa-miR-503 | MIMAT0002874 | uagcagcgggaacaguucugcag | 175 |
| hsa-miR-505 | MIMAT0002876 | cgucaacacuugcugguuuccu | 176 |
| hsa-miR-507 | MIMAT0002879 | uuuugcaccuuuuggagugaa | 177 |
| hsa-miR-511 | MIMAT0002808 | gugucuuuugcucugcaguca | 178 |
| hsa-miR-513a-3p | MIMAT0004777 | uaaauuucaccuuucugagaagg | 179 |
| hsa-miR-513a-5p | MIMAT0002877 | uucacagggaggugucau | 180 |
| hsa-miR-513b | MIMAT0005788 | uucacaaggaggugucauuuau | 181 |
| hsa-miR-513c | MIMAT0005789 | uucucaaggaggugucguuuau | 182 |
| hsa-miR-515-5p | MIMAT0002826 | uucuccaaaagaaagcacuuucug | 183 |
| hsa-miR-518b | MIMAT0002844 | caaagcgcuccccuuuagaggu | 184 |
| hsa-miR-518c* | MIMAT0002847 | ucucuggagggaagcacuuucug | 185 |
| hsa-miR-518d-3p | MIMAT0002864 | caaagcgcuucccuuuggagc | 186 |
| hsa-miR-518d-5p | MIMAT0005456 | cucuagagggaagcacuuucug | 187 |
| hsa-miR-518e* | MIMAT0005450 | cucuagagggaagcgcuuucug | 188 |
| hsa-miR-520d-5p | MIMAT0002855 | cuacaaagggaagcccuuuc | 189 |
| hsa-miR-520h | MIMAT0002867 | acaaagugcuucccuuuagagu | 190 |
| hsa-miR-539 | MIMAT0003163 | ggagaaauuauccuuggugugu | 191 |
| hsa-miR-541 | MIMAT0004920 | uggugggcacagaaucuggacu | 192 |
| hsa-miR-545* | MIMAT0004785 | ucaguaaauguuuauuagauga | 193 |
| hsa-miR-548d-3p | MIMAT0003323 | caaaaaccacaguuucuuuugc | 194 |
| hsa-miR-548d-5p | MIMAT0004812 | aaaaguaauugugguuuuugcc | 195 |
| hsa-miR-551a | MIMAT0003214 | gcgacccacucuugguuucca | 196 |
| hsa-miR-551b | MIMAT0003233 | gcgacccauacuugguuucag | 197 |
| hsa-miR-552 | MIMAT0003215 | aacaggugacugguuagacaa | 198 |
| hsa-miR-554 | MIMAT0003217 | gcuaguccugacucagccagu | 199 |
| hsa-miR-556-5p | MIMAT0003220 | gaugagcucauuguaauaugag | 200 |
| hsa-miR-557 | MIMAT0003221 | guuugcacgggugggccuugucu | 201 |
| hsa-miR-559 | MIMAT0003223 | uaaaguaaauaugcaccaaaa | 202 |
| hsa-miR-561 | MIMAT0003225 | caaaguuuaagauccuugaagu | 203 |
| hsa-miR-564 | MIMAT0003228 | aggcacggugucagcaggc | 204 |
| hsa-miR-568 | MIMAT0003232 | auguauaaauguauacacac | 205 |
| hsa-miR-572 | MIMAT0003237 | guccgcucggcgguggccca | 206 |

Appendix A -continued

| miRNA name | Accession Number | RNA Sequence | SEQ ID No: |
|---|---|---|---|
| hsa-miR-574-5p | MIMAT0004795 | ugagugugugugugagugugu | 207 |
| hsa-miR-575 | MIMAT0003240 | gagccaguuggacaggagc | 208 |
| hsa-miR-576-3p | MIMAT0004796 | aagauguggaaaaauuggaauc | 209 |
| hsa-miR-578 | MIMAT0003243 | cuucuugugcucuaggauugu | 210 |
| hsa-miR-583 | MIMAT0003248 | caaagaggaaggucccauuac | 211 |
| hsa-miR-586 | MIMAT0003252 | uaugcauuguauuuuaggucc | 212 |
| hsa-miR-589 | MIMAT0004799 | ugagaaccacgucugcucugag | 213 |
| hsa-miR-589* | MIMAT0003256 | ucagaacaaaugccgguucccaga | 214 |
| hsa-miR-591 | MIMAT0003259 | agaccaugggtuucucauugu | 215 |
| hsa-miR-595 | MIMAT0003263 | gaagugugccguggugugucu | 216 |
| hsa-miR-601 | MIMAT0003269 | uggucuaggauuguuggaggag | 217 |
| hsa-miR-602 | MIMAT0003270 | gacacgggcgacagcugcggccc | 218 |
| hsa-miR-609 | MIMAT0003277 | aggguguuucucucaucucu | 219 |
| hsa-miR-610 | MIMAT0003278 | ugagcuaaaugugugcuggga | 220 |
| hsa-miR-612 | MIMAT0003280 | gcugggcagggcuucugagcuccuu | 221 |
| hsa-miR-613 | MIMAT0003281 | aggaauguuccuucuuugcc | 222 |
| hsa-miR-614 | MIMAT0003282 | gaacgccuguucuugccaggugg | 223 |
| hsa-miR-615-3p | MIMAT0003283 | uccgagccugggucucccucuu | 224 |
| hsa-miR-616 | MIMAT0004805 | agucauuggaggguuugagcag | 225 |
| hsa-miR-619 | MIMAT0003288 | gaccuggacauguuugugcccagu | 226 |
| hsa-miR-622 | MIMAT0003291 | acagucugcugagguuggagc | 227 |
| hsa-miR-623 | MIMAT0003292 | aucccuugcaggggcuguugggu | 228 |
| hsa-miR-624* | MIMAT0003293 | uaguaccaguaccuuguguuca | 229 |
| hsa-miR-627 | MIMAT0003296 | gugagucucuaagaaaagagga | 230 |
| hsa-miR-630 | MIMAT0003299 | aguauucuguaccagggaaggu | 231 |
| hsa-miR-633 | MIMAT0003303 | cuaauaguaucuaccacaauaaa | 232 |
| hsa-miR-634 | MIMAT0003304 | aaccagcaccccaacuuuggac | 233 |
| hsa-miR-638 | MIMAT0003308 | agggaucgcgggcggguggcggccu | 234 |
| hsa-miR-639 | MIMAT0003309 | aucgcugcgguugcgagcgcugu | 235 |
| hsa-miR-640 | MIMAT0003310 | augaccaggaaccugcccucu | 236 |
| hsa-miR-642 | MIMAT0003312 | gucccucuccaaaugugucuug | 237 |
| hsa-miR-644 | MIMAT0003314 | aguugggcuuucuuagagc | 238 |
| hsa-miR-647 | MIMAT0003317 | guggcugcacucacuuccuuc | 239 |
| hsa-miR-648 | MIMAT0003318 | aagugugcagggcacuggu | 240 |
| hsa-miR-652 | MIMAT0003322 | aauggcgccacuagggguugug | 241 |
| hsa-miR-654-5p | MIMAT0003330 | uggugggccgcagaacaugugc | 242 |
| hsa-miR-658 | MIMAT0003336 | ggcggagggaaguagguccguuggu | 243 |
| hsa-miR-659 | MIMAT0003337 | cuuggtuucagggagggucccca | 244 |

-continued

Appendix A

| miRNA name | Accession Number | RNA Sequence | SEQ ID No: |
|---|---|---|---|
| hsa-miR-662 | MIMAT0003325 | ucccacguuguggcccagcag | 245 |
| hsa-miR-663 | MIMAT0003326 | aggcggggcgccgcgggaccgc | 246 |
| hsa-miR-665 | MIMAT0004952 | accaggaggcugaggccccu | 247 |
| hsa-miR-671-5p | MIMAT0003880 | aggaagcccuggaggggcuggag | 248 |
| hsa-miR-675 | MIMAT0004284 | uggugcggagagggcccacagug | 249 |
| hsa-miR-708 | MIMAT0004926 | aaggagcuuacaaucuagcuggg | 250 |
| hsa-miR-708* | MIMAT0004927 | caacuagacugugagcuucag | 251 |
| hsa-miR-711 | MIMAT0012734 | gggacccagggagagacguaag | 252 |
| hsa-miR-720 | MIMAT0005954 | ucucgcuggggccucca | 253 |
| hsa-miR-744* | MIMAT0004946 | cuguugccacuaaccucaaccu | 254 |
| hsa-miR-760 | MIMAT0004957 | cggcucugggucuguggga | 255 |
| hsa-miR-765 | MIMAT0003945 | uggaggagaaggaaggugaug | 256 |
| hsa-miR-766 | MIMAT0003888 | acuccagccccacagccucagc | 257 |
| hsa-miR-767-3p | MIMAT0003883 | ucugcucauaccccaugguuucu | 258 |
| hsa-miR-770-5p | MIMAT0003948 | uccaguaccacgugucagggcca | 259 |
| hsa-miR-802 | MIMAT0004185 | caguaacaaagauucauccuugu | 260 |
| hsa-miR-874 | MIMAT0004911 | cugcccuggcccgagggaccga | 261 |
| hsa-miR-876-3p | MIMAT0004925 | uggugguuuacaaaguaauuca | 262 |
| hsa-miR-876-5p | MIMAT0004924 | uggauuucuuugugaaucacca | 263 |
| hsa-miR-877 | MIMAT0004949 | guagaggagauggcgcaggg | 264 |
| hsa-miR-877* | MIMAT0004950 | uccucuucucccuccucccag | 265 |
| hsa-miR-885-3p | MIMAT0004948 | aggcagcggggguguaguggaua | 266 |
| hsa-miR-885-5p | MIMAT0004947 | uccauuacacuacccugccucu | 267 |
| hsa-miR-886-3p | MIMAT0004906 | cgcgggugcuuacugacccuu | 268 |
| hsa-miR-890 | MIMAT0004912 | uacuuggaaaggcaucaguug | 269 |
| hsa-miR-891b | MIMAT0004913 | ugcaacuuaccugagucauuga | 270 |
| hsa-miR-892b | MIMAT0004918 | cacuggcuccuuucugguaga | 271 |
| hsa-miR-920 | MIMAT0004970 | ggggagcuguggaagcagua | 272 |
| hsa-miR-922 | MIMAT0004972 | gcagcagagaauaggacuacguc | 273 |
| hsa-miR-923 | none | GUCAGCGGAGGAAAAGAAACU | 274 |
| hsa-miR-92a-2* | MIMAT0004508 | gguguggggauuuguugcauuac | 275 |
| hsa-miR-92b | MIMAT0003218 | uauugcacucgucccggccucc | 276 |
| hsa-miR-92b* | MIMAT0004792 | agggacgggacgcggugcagug | 277 |
| hsa-miR-93 | MIMAT0000093 | caaagugcuguucgugcagguag | 278 |
| hsa-miR-933 | MIMAT0004976 | ugugcgcagggagaccucuccc | 279 |
| hsa-miR-934 | MIMAT0004977 | ugucuacuacuggagacacugg | 280 |
| hsa-miR-935 | MIMAT0004978 | ccaguuaccgcuuccgcuaccgc | 281 |
| hsa-miR-936 | MIMAT0004979 | acaguagagggaggaaucgcag | 282 |

-continued

Appendix A

| miRNA name | Accession Number | RNA Sequence | SEQ ID No: |
|---|---|---|---|
| hsa-miR-937 | MIMAT0004980 | auccgcgcucugacucucugcc | 283 |
| hsa-miR-939 | MIMAT0004982 | uggggagcugaggcucuggggug | 284 |
| hsa-miR-940 | MIMAT0004983 | aaggcagggccccgcucccc | 285 |
| hsa-miR-96 | MIMAT0000095 | uuuggcacuagcacauuuugcu | 286 |
| hsa-miR-99a | MIMAT0000097 | aacccguagauccgaucuugug | 287 |
| hsv1-miR-H1 | MIMAT0003744 | uggaaggacgggaaguggaag | 288 |
| hsv1-miR-LAT | none | uggcggcccggcccggggcc | 289 |
| kshv-miR-K12-12 | IMAT0003712 | accaggccaccauuccucuccg | 290 |
| kshv-miR-K12-3 | MIMAT0002193 | ucacauucugaggacggcagcga | 291 |
| kshv-miR-K12-3* | MIMAT0002194 | ucgcggucacagaaugugaca | 292 |
| kshv-miR-K12-4-5p | MIMAT0002191 | agcuaaaccgcaguacucuagg | 293 |
| kshv-miR-K12-6-5p | MIMAT0002188 | ccagcagcaccuaauccaucgg | 294 |
| kshv-miR-K12-8 | MIMAT0002186 | uaggcgcgacugagagagcacg | 295 |
| kshv-miR-K12-9 | MIMAT0002185 | cugggauacgcagcugcguaa | 296 |
| kshv-miR-K12-9* | MIMAT0002184 | acccagcugcguaaaccccgcu | 297 |
| mghv-miR-M1-6 | MIMAT0001569 | ugaaacugugugaggugguuuu | 298 |
| mghv-miR-M1-9 | MIMAT0001573 | ucacauugccuggaccuuuuu | 299 |
| mmu-let-7d* | MIMAT0000384 | cuauacgaccugcugccuuucu | 300 |
| mmu-let-7g | MIMAT0000121 | ugagguaguaguuuguacaguu | 301 |
| mmu-miR-298 | MIMAT0000376 | ggcagagggggcuguucuuccc | 302 |
| mmu-miR-1 | MIMAT0000123 | uggaauguaaagaaguauguau | 303 |
| mmu-miR-101a | MIMAT0000133 | uacaguacugugauaacugaa | 304 |
| mmu-miR-101a* | MIMAT0004526 | ucaguuaucacagugcugaugc | 305 |
| mmu-miR-101b | MIMAT0000616 | uacaguacugugauagcugaa | 306 |
| mmu-miR-122 | MIMAT0000246 | uggagugugacaaugguguuug | 307 |
| mmu-miR-1224 | MIMAT0005460 | gugaggacuggggaggugag | 308 |
| mmu-miR-124 | MIMAT0000134 | uaaggcacgcggugaaugcc | 309 |
| mmu-miR-125a-3p | MIMAT0004528 | acaggugagguucuugggagcc | 310 |
| mmu-miR-125a-5p | MIMAT0000135 | ucccugagacccuuuaaccuguga | 311 |
| mmu-miR-125b-5p | MIMAT0000136 | ucccugagacccuaacuuguga | 312 |
| mmu-miR-126-5p | MIMAT0000137 | auuauuacuuuugguacgcg | 313 |
| mmu-miR-127 | MIMAT0000139 | ucggauccgucugagcuuggcu | 314 |
| mmu-miR-128 | MIMAT0000140 | ucacagugaaccggucucuuu | 315 |
| mmu-miR-129-3p | MIMAT0000544 | aagcccuuaccccaaaaagcau | 316 |
| mmu-miR-130a | MIMAT0000141 | cagugcaauguuaaagggcau | 317 |
| mmu-miR-133a | MIMAT0000145 | uuggucccuucaaccagcug | 318 |
| mmu-miR-133b | MIMAT0000769 | uuggucccuucaaccagcua | 319 |
| mmu-miR-135a* | MIMAT0004531 | uauagggauuggagccguggcg | 320 |

-continued

Appendix A

| miRNA name | Accession Number | RNA Sequence | SEQ ID No: |
|---|---|---|---|
| mmu-miR-136 | MIMAT0000148 | acuccauuuguuuugaugaugg | 321 |
| mmu-miR-138 | MIMAT0000150 | agcugguguugugaaucaggccg | 322 |
| mmu-miR-138* | MIMAT0004668 | ggcuacuucacaacaccaggg | 323 |
| mmu-miR-139-3p | MIMAT0004662 | uggagacgcggcccuguuggag | 324 |
| mmu-miR-140 | MIMAT0000151 | cagugguuuuacccuaugguag | 325 |
| mmu-miR-140* | MIMAT0000152 | uaccacaggguagaaccacgg | 326 |
| mmu-miR-141 | MIMAT0000153 | uaacacugucugguaaagaugg | 327 |
| mmu-miR-142-3p | MIMAT0000155 | uguaguguuuccuacuuuaugga | 328 |
| mmu-miR-143 | MIMAT0000247 | ugagaugaagcacuguagcuc | 329 |
| mmu-miR-146a | MIMAT0000158 | ugagaacugaauuccauggguu | 330 |
| mmu-miR-146b | MIMAT0003475 | ugagaacugaauuccauaggcu | 331 |
| mmu-miR-148b | MIMAT0000580 | ucagugcaucacagaacuuugu | 332 |
| mmu-miR-150 | MIMAT0000160 | ucucccaacccuuguaccagug | 333 |
| mmu-miR-15a* | MIMAT0004624 | caggccauacugugcugccuca | 334 |
| mmu-miR-15b | MIMAT0000124 | uagcagcacaucaugguuuaca | 335 |
| mmu-miR-181b | MIMAT0000673 | aacauucauugcugucgguggu | 336 |
| mmu-miR-181d | MIMAT0004324 | aacauucauuguugucgguggu | 337 |
| mmu-miR-183 | MIMAT0000212 | uauggcacugguagaauucacu | 338 |
| mmu-miR-185 | MIMAT0000214 | uggagagaaaggcaguuccuga | 339 |
| mmu-miR-186 | MIMAT0000215 | caaagaauucuccuuuugggcu | 340 |
| mmu-miR-191* | MIMAT0004542 | gcugcacuuggauuucguuccc | 341 |
| mmu-miR-193 | MIMAT0000223 | aacuggccuacaaagucccagu | 342 |
| mmu-miR-193b | MIMAT0004859 | aacuggcccacaaagucccgcu | 343 |
| mmu-miR-194 | MIMAT0000224 | uguaacagcaacuccaugugga | 344 |
| mmu-miR-199a-5p | MIMAT0000229 | cccaguguucagacuaccuguuc | 345 |
| mmu-miR-199b* | MIMAT0000672 | cccaguguuuagacuaccuguuc | 346 |
| mmu-miR-19a | MIMAT0000651 | ugugcaaaucuaugcaaaacuga | 347 |
| mmu-miR-200a | MIMAT0000519 | uaacacugucugguaacgaugu | 348 |
| mmu-miR-200b | MIMAT0000233 | uaauacugccugguaaugauga | 349 |
| mmu-miR-200b* | MIMAT0004545 | caucuuacugggcagcauugga | 350 |
| mmu-miR-200c | MIMAT0000657 | uaauacugccggguaaugaugga | 351 |
| mmu-miR-202-3p | MIMAT0000235 | agagguauagcgcaugggaaga | 352 |
| mmu-miR-205 | MIMAT0000238 | uccuucauuccaccggagucug | 353 |
| mmu-miR-206 | MIMAT0000239 | uggaauguaaggaaguguggg | 354 |
| mmu-miR-208a | MIMAT0000520 | auaagacgagcaaaaagcuugu | 355 |
| mmu-miR-21 | MIMAT0000530 | uagcuuaucagacugauguuga | 356 |
| mmu-miR-211 | MIMAT0000668 | uucccuuugucauccuuugccu | 357 |
| mmu-miR-22 | MIMAT0000531 | aagcugccaguugaagaacugu | 358 |

-continued

Appendix A

| miRNA name | Accession Number | RNA Sequence | SEQ ID No: |
|---|---|---|---|
| mmu-miR-221 | MIMAT0000669 | agcuacauugucugcuggguuuc | 359 |
| mmu-miR-222 | MIMAT0000670 | agcuacaucuggcuacugggu | 360 |
| mmu-miR-223 | MIMAT0000665 | ugucaguuugucaaauacccca | 361 |
| mmu-miR-23b | MIMAT0000125 | aucacauugccagggauuacc | 362 |
| mmu-miR-26a | MIMAT0000533 | uucaaguaauccaggauaggcu | 363 |
| mmu-miR-27a | MIMAT0000537 | uucacaguggcuaaguuccgc | 364 |
| mmu-miR-27b | MIMAT0000126 | uucacaguggcuaaguucugc | 365 |
| mmu-miR-27b* | MIMAT0004522 | agagcuuagcugauuggugaac | 366 |
| mmu-miR-28* | MIMAT0004661 | cacuagauugugagcugcugga | 367 |
| mmu-miR-290-5p | MIMAT0000366 | acucaaacuauggggcacuuu | 368 |
| mmu-miR-291a-5p | MIMAT0000367 | caucaaaguggaggcccucucu | 369 |
| mmu-miR-294* | MIMAT0004574 | acucaaaauggaggcccuaucu | 370 |
| mmu-miR-297a | MIMAT0000375 | auguaugugugcaugugcaugu | 371 |
| mmu-miR-299 | MIMAT0004577 | uauguggggacgguaaaccgcuu | 372 |
| mmu-miR-29b | MIMAT0000127 | uagcaccauuugaaaucaguguu | 373 |
| mmu-miR-29c* | MIMAT0004632 | ugaccgauuucuccugguguuc | 374 |
| mmu-miR-301b | MIMAT0004186 | cagugcaaugguauugucaaagc | 375 |
| mmu-miR-302c* | MIMAT0003375 | gcuuuaacauggggguuaccuge | 376 |
| mmu-miR-30a | MIMAT0000128 | uguaaacauccucgacuggaag | 377 |
| mmu-miR-30c | MIMAT0000514 | uguaaacauccuacacucucagc | 378 |
| mmu-miR-30c-1* | MIMAT0004616 | cugggagaggguuguuuacucc | 379 |
| mmu-miR-30e | MIMAT0000248 | uguaaacauccuugacuggaag | 380 |
| mmu-miR-31 | MIMAT0000538 | aggcaagaugcuggcauagcug | 381 |
| mmu-miR-320 | MIMAT0000666 | aaaagcuggguugagagggcga | 382 |
| mmu-miR-322 | MIMAT0000548 | cagcagcaauucauguuuugga | 383 |
| mmu-miR-323-3p | MIMAT0000551 | cacauuacacggucgaccucu | 384 |
| mmu-miR-324-3p | MIMAT0000556 | ccacugccccaggugcugcu | 385 |
| mmu-miR-324-5p | MIMAT0000555 | cgcaucccuagggcauuggugu | 386 |
| mmu-miR-326 | MIMAT0000559 | ccucugggcccuuccuccagu | 387 |
| mmu-miR-327 | MIMAT0004867 | acuugaggggcaugaggau | 388 |
| mmu-miR-328 | MIMAT0000565 | cuggcccucucugcccuuccgu | 389 |
| mmu-miR-331-5p | MIMAT0004643 | cuagguauggucccagggaucc | 390 |
| mmu-miR-339-3p | MIMAT0004649 | ugagcgccucggcgacagagccg | 391 |
| mmu-miR-341 | MIMAT0000588 | ucggucgaucggucggucggu | 392 |
| mmu-miR-342-3p | MIMAT0000590 | ucucacacagaaaucgcacccgu | 393 |
| mmu-miR-34b-5p | MIMAT0000382 | aggcaguguaauuagcugauugu | 394 |
| mmu-miR-34c* | MIMAT0004580 | aaucacuaaccacacagccagg | 395 |
| mmu-miR-369-3p | MIMAT0003186 | aauaauacaugguugaucuuu | 396 |

-continued

Appendix A

| miRNA name | Accession Number | RNA Sequence | SEQ ID No: |
|---|---|---|---|
| mmu-miR-370 | MIMAT0001095 | gccugcugggguggaaccuggu | 397 |
| mmu-miR-374 | MIMAT0003727 | auauaauacaaccugcuaagug | 398 |
| mmu-miR-375 | MIMAT0000739 | uuuguucguucggcucgcguga | 399 |
| mmu-miR-376b | MIMAT0001092 | aucauagaggaacauccacuu | 400 |
| mmu-miR-379 | MIMAT0000743 | ugguagacuauggaacguagg | 401 |
| mmu-miR-380-3p | MIMAT0000745 | uauguaguaugguccacaucuu | 402 |
| mmu-miR-382 | MIMAT0000747 | gaaguuguucguggugauucg | 403 |
| mmu-miR-384-5p | MIMAT0004745 | uguaaacaauuccuaggcaaugu | 404 |
| mmu-miR-409-5p | MIMAT0004746 | agguuacccgagcaacuuugcau | 405 |
| mmu-miR-411 | MIMAT0004747 | uaguagaccguauagcguacg | 406 |
| mmu-miR-411* | MIMAT0001093 | uauguaacacgguccacuaacc | 407 |
| mmu-miR-423-5p | MIMAT0004825 | ugaggggcagagagcgagacuuu | 408 |
| mmu-miR-425 | MIMAT0004750 | aaugacacgaucacucccguuga | 409 |
| mmu-miR-429 | MIMAT0001537 | uaauacugucugguaaugccgu | 410 |
| mmu-miR-434-5p | MIMAT0001421 | gcucgacucaugguuugaacca | 411 |
| mmu-miR-450b-3p | MIMAT0003512 | auugggaacauuuugcaugcau | 412 |
| mmu-miR-451 | MIMAT0001632 | aaaccguuaccauuacugaguu | 413 |
| mmu-miR-455 | MIMAT0003742 | gcaguccacgggcauauacac | 414 |
| mmu-miR-465c-3p | MIMAT0004874 | gaucagggccuuucuaaguaga | 415 |
| mmu-miR-466d-5p | MIMAT0004930 | ugugugugcguacauguacaug | 416 |
| mmu-miR-466f-3p | MIMAT0004882 | cauacacacacauacacac | 417 |
| mmu-miR-467e* | MIMAT0005294 | auauacauacacacaccuauau | 418 |
| mmu-miR-483 | MIMAT0004782 | aagacgggagaagagaagggag | 419 |
| mmu-miR-484 | MIMAT0003127 | ucaggcucaguccccucccgau | 420 |
| mmu-miR-486 | MIMAT0003130 | uccuguacugagcugccccgag | 421 |
| mmu-miR-487b | MIMAT0003184 | aaucgacagggucauccacuu | 422 |
| mmu-miR-494 | MIMAT0003182 | ugaaacauacacgggaaaccuc | 423 |
| mmu-miR-497 | MIMAT0003453 | cagcagcacacugugguuugua | 424 |
| mmu-miR-505 | IMAT0003513 | cgucaacacuugcugguuuucu | 425 |
| mmu-miR-511 | MIMAT0004940 | augccuuuugcucugcacuca | 426 |
| mmu-miR-539 | MIMAT0003169 | ggagaaauuauccuuggugugu | 427 |
| mmu-miR-540-3p | MIMAT0004786 | caagggucacccucugacucugu | 428 |
| mmu-miR-551b | MIMAT0003890 | gcgacccauacuuggguuucag | 429 |
| mmu-miR-568 | MIMAT0004892 | auguauaaauguauacacac | 430 |
| mmu-miR-574-5p | MIMAT0004893 | ugagugugugugugagugugu | 431 |
| mmu-miR-652 | MIMAT0003711 | aauggcgccacuagggguugug | 432 |
| mmu-miR-654-5p | MIMAT0004897 | ugguaagcugcagaacauguguu | 433 |
| mmu-miR-669a | MIMAT0003477 | aguugugugugcauguucaugu | 434 |

-continued

Appendix A

| miRNA name | Accession Number | RNA Sequence | SEQ ID No: |
|---|---|---|---|
| mmu-miR-671-5p | MIMAT0003731 | aggaagcccuggaggggcuggag | 435 |
| mmu-miR-685 | MIMAT0003463 | ucaauggcugaggugaggcac | 436 |
| mmu-miR-686 | MIMAT0003464 | auugcuucccagacggugaaga | 437 |
| mmu-miR-688 | MIMAT0003467 | ucgcaggcgacuacuuauuc | 438 |
| mmu-miR-701 | MIMAT0003491 | uuagccgcugaaauagaugga | 439 |
| mmu-miR-706 | MIMAT0003496 | agagaaacccugucucaaaaaa | 440 |
| mmu-miR-708 | MIMAT0004828 | aaggagcuuacaaucuagcuggg | 441 |
| mmu-miR-710 | MIMAT0003500 | ccaagucuuggggagaguugag | 442 |
| mmu-miR-711 | MIMAT0003501 | gggacccggggagagauguaag | 443 |
| mmu-miR-712 | MIMAT0003502 | cuccuucacccgggcgguacc | 444 |
| mmu-miR-714 | MIMAT0003505 | cgacgagggccggucggucgc | 445 |
| mmu-miR-720 | MIMAT0003484 | aucucgcuggggccucca | 446 |
| mmu-miR-721 | MIMAT0003515 | cagugcaauuaaaagggggaa | 447 |
| mmu-miR-744* | MIMAT0004820 | cuguugccacuaaccucaaccu | 448 |
| mmu-miR-760 | MIMAT0003898 | cggcucugggucuguggga | 449 |
| mmu-miR-770-5p | MIMAT0004822 | agcaccacgugucugggccacg | 450 |
| mmu-miR-7a | MIMAT0000677 | uggaagacuagugauuuuguugu | 451 |
| mmu-miR-7b | MIMAT0000678 | uggaagacuugugauuuuguugu | 452 |
| mmu-miR-877 | MIMAT0004861 | guagaggagauggcgcaggg | 453 |
| mmu-miR-877* | MIMAT0004862 | uguccucuucucccuccuccca | 454 |
| mmu-miR-881* | MIMAT0004845 | cagagagauaacagucacaucu | 455 |
| mmu-miR-882 | MIMAT0004847 | aggagagaguuagcgcauuagu | 456 |
| mmu-miR-93 | MIMAT0000540 | caaagugcuguucgugcagguag | 457 |
| mmu-miR-96 | MIMAT0000541 | uuuggcacuagcacauuuugcu | 458 |
| mmu-miR-99a | MIMAT0000131 | aacccguagauccgaucuugug | 459 |

The devices and methods of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

What is claimed is:

1. A method of detecting or predicting a liver condition, comprising:
    generating a microRNA profile from a biological sample, wherein the microRNA profile comprises the amounts of at least two specific microRNA sequences, by:
        receiving the biological sample, the sample being a tissue, serum, or plasma; and
        isolating microRNA from the biological sample by extracting the microRNA with an organic solvent and obtaining an aqueous phase containing the microRNA, then purifying the aqueous phase through a silica membrane to isolate the microRNA;
    using hybridization to identify the microRNA sequences; and
    measuring the amount of at least two specific microRNA sequences; and
    comparing the amounts of the at least two specific microRNA sequences to a reference to provide information for detecting or predicting the liver condition;
    wherein the at least two specific microRNA sequences are hsa-miR-122 and hsa-miR-486-3p.

2. The method of claim 1, wherein the ratio of the amount of hsa-miR-122 to the amount of hsa-miR-486-3p is greater than 4.0.

3. The method of claim 1, wherein the ratio of the amount of hsa-miR-122 to the amount of hsa-miR-486-3p is greater than 6.0.

4. A method as in any of claim 1, 2, or 3, further comprising recording the output/result of the diagnostic method on a data storage medium.

5. The method of claim 1, wherein the microRNA profile further comprises the amount of at least one additional microRNA sequence selected from the group consisting of miR-486, miR-125b-5p, let-7d*, miR-101a, miR-101b, miR-1224, miR-124, miR-125a-3p, miR-125a-5p, miR-127, miR-130a, miR-133a, miR-133b, miR-135a*, miR-141, miR-193, miR-193b, miR-199a-5p, miR-199b*, miR-200c, miR-202-3p, miR-205, miR-22, miR-23b, miR-26a, miR-27b, miR-291a-5p, miR-294*, miR-29b, miR-30a, miR-30c-1*, miR-30e, miR-320, miR-327, miR-339-3p, miR-342-3p, miR-370, miR-375, miR-451, miR-466f-3p, miR-483, miR-486-5p, miR-494, miR-574-5p, miR-652, miR-671-5p, miR-685, miR-710, miR-711, miR-712, miR-714, miR-720, miR-721, miR-877, miR-877*, miR-882, miR-93, miR-99a, and human orthologs thereof.

6. The method of claim 1, wherein the amount of at least two specific microRNA sequences is measured using quantitative polymerase chain reaction (qPCR).

7. The method of claim 1, further comprising administering a treatment to a patient providing the biological sample based on the identity or amounts of the at least two specific microRNA sequences.

* * * * *